(12) United States Patent
Mirkov et al.

(10) Patent No.: US 11,418,000 B2
(45) Date of Patent: Aug. 16, 2022

(54) Q-SWITCHED CAVITY DUMPED SUB-NANOSECOND LASER

(71) Applicant: Cynosure, LLC, Westford, MA (US)

(72) Inventors: Mirko Mirkov, Chelmsford, MA (US); Henry Zenzie, Dover, MA (US)

(73) Assignee: Cynosure, LLC, Westford, MA (US)

( * ) Notice: Subject to any disclaimer, the term of this patent is extended or adjusted under 35 U.S.C. 154(b) by 0 days.

(21) Appl. No.: 16/975,540

(22) PCT Filed: Feb. 26, 2019

(86) PCT No.: PCT/US2019/019583
§ 371 (c)(1),
(2) Date: Aug. 25, 2020

(87) PCT Pub. No.: WO2019/165426
PCT Pub. Date: Aug. 29, 2019

(65) Prior Publication Data
US 2020/0412082 A1 Dec. 31, 2020

Related U.S. Application Data

(60) Provisional application No. 62/653,767, filed on Apr. 6, 2018, provisional application No. 62/635,174, filed on Feb. 26, 2018.

(51) Int. Cl.
*H01S 3/11* (2006.01)
*G02F 1/03* (2006.01)
(Continued)

(52) U.S. Cl.
CPC .............. *H01S 3/1127* (2013.01); *G02F 1/03* (2013.01); *H01S 3/115* (2013.01); *H01S 3/1312* (2013.01);
(Continued)

(58) Field of Classification Search
CPC .................. H01S 3/1127; H01S 3/115; A61B 2017/00756; A61B 2017/00769
See application file for complete search history.

(56) References Cited

U.S. PATENT DOCUMENTS 853,033 A 5/1907 Roberts
1,590,283 A 6/1926 Catlin
(Continued)

FOREIGN PATENT DOCUMENTS

AT 400305 B 12/1995
AU 1851583 A 3/1984
(Continued)

OTHER PUBLICATIONS

May 7, 2019—International Search Report & Written Opinion for PCT/US2019/019583.
(Continued)

*Primary Examiner* — Michael Carter
(74) *Attorney, Agent, or Firm* — Banner & Witcoff, Ltd.

(57) ABSTRACT

Apparatuses and methods are disclosed for applying laser energy having desired pulse characteristics, including a sufficiently short duration and/or a sufficiently high energy for the photomechanical treatment of skin pigmentations and pigmented lesions, both naturally-occurring (e.g., birthmarks), as well as artificial (e.g., tattoos). The laser energy may be generated with an apparatus having a resonator with a sub-nanosecond round trip time.

29 Claims, 20 Drawing Sheets
(3 of 20 Drawing Sheet(s) Filed in Color)

(51) Int. Cl.
*H01S 3/115* (2006.01)
*H01S 3/131* (2006.01)
*H01S 3/16* (2006.01)
*A61B 17/00* (2006.01)

(52) U.S. Cl.
CPC .. *H01S 3/1643* (2013.01); *A61B 2017/00756* (2013.01); *A61B 2017/00769* (2013.01)

(56) References Cited

U.S. PATENT DOCUMENTS

| | | |
|---|---|---|
| 1,676,183 A | 7/1928 | Garfunkle |
| 1,706,161 A | 3/1929 | Hollnagel |
| 2,068,721 A | 1/1937 | Wappler et al. |
| 2,472,385 A | 6/1949 | Rollman |
| 2,669,771 A | 2/1954 | Burge et al. |
| 3,243,650 A | 3/1966 | Hawkins et al. |
| 3,261,978 A | 7/1966 | Brenman |
| 3,284,665 A | 11/1966 | Goncz |
| 3,327,712 A | 6/1967 | Kaufman et al. |
| 3,465,203 A | 9/1969 | Galster et al. |
| 3,486,070 A | 12/1969 | Engel |
| 3,524,144 A | 8/1970 | Buser et al. |
| 3,527,932 A | 9/1970 | Thomas |
| 3,538,919 A | 11/1970 | Meyer |
| 3,597,652 A | 8/1971 | Gates, Jr. |
| 3,622,743 A | 11/1971 | Muncheryan |
| 3,651,425 A | 3/1972 | McKnight |
| 3,653,778 A | 4/1972 | Freiling |
| 3,667,454 A | 6/1972 | Prince |
| 3,693,623 A | 9/1972 | Harte et al. |
| 3,699,967 A | 10/1972 | Anderson |
| 3,725,733 A | 4/1973 | Mack et al. |
| 3,766,393 A | 10/1973 | Herzog et al. |
| 3,766,488 A | 10/1973 | Kohn |
| 3,769,963 A | 11/1973 | Goldman et al. |
| 3,793,723 A | 2/1974 | Kuris et al. |
| 3,794,028 A | 2/1974 | Mueller et al. |
| 3,815,046 A | 6/1974 | Johnson et al. |
| 3,818,373 A | 6/1974 | Chun et al. |
| 3,818,914 A | 6/1974 | Bender |
| 3,821,510 A | 6/1974 | Muncheryan |
| 3,834,391 A | 9/1974 | Block |
| 3,843,865 A | 10/1974 | Nath |
| 3,846,811 A | 11/1974 | Nakamura et al. |
| 3,857,015 A | 12/1974 | Clark et al. |
| 3,858,577 A | 1/1975 | Bass et al. |
| 3,861,921 A | 1/1975 | Hoffmann et al. |
| 3,885,569 A | 5/1975 | Judson |
| 3,890,537 A | 6/1975 | Park et al. |
| 3,900,034 A | 8/1975 | Katz et al. |
| 3,909,649 A | 9/1975 | Arsena |
| 3,914,709 A | 10/1975 | Pike et al. |
| 3,939,560 A | 2/1976 | Lyall |
| 3,977,083 A | 8/1976 | Leslie et al. |
| 3,980,861 A | 9/1976 | Fukunaga |
| 4,019,156 A * | 4/1977 | Fountain ............... H01S 3/1115 372/18 |
| 4,037,136 A | 7/1977 | Hoene |
| 4,038,984 A | 8/1977 | Sittner |
| 4,047,106 A | 9/1977 | Robinson |
| 4,065,370 A | 12/1977 | Noble et al. |
| 4,122,853 A | 10/1978 | Smith |
| 4,133,503 A | 1/1979 | Bliss |
| 4,139,342 A | 2/1979 | Sheldrake et al. |
| 4,154,240 A | 5/1979 | Ikuno et al. |
| 4,176,324 A | 11/1979 | Aldag et al. |
| 4,176,327 A | 11/1979 | Wayne et al. |
| 4,188,927 A | 2/1980 | Harris |
| 4,213,462 A | 7/1980 | Sato |
| 4,228,800 A | 10/1980 | Degler, Jr. et al. |
| 4,233,493 A | 11/1980 | Nath |
| 4,254,333 A | 3/1981 | Bergstrom |
| 4,259,123 A | 3/1981 | Tymkewicz |
| 4,269,067 A | 5/1981 | Tynan et al. |
| 4,273,109 A | 6/1981 | Enderby |
| 4,275,335 A | 6/1981 | Ishida |
| 4,291,281 A | 9/1981 | Pinard et al. |
| 4,292,601 A | 9/1981 | Aldag et al. |
| 4,293,827 A | 10/1981 | McAllister et al. |
| 4,298,005 A | 11/1981 | Mutzhas |
| 4,299,912 A | 11/1981 | Shiba et al. |
| 4,302,730 A | 11/1981 | Jernigan |
| 4,313,431 A | 2/1982 | Frank |
| 4,316,467 A | 2/1982 | Muckerheide |
| 4,333,197 A | 6/1982 | Kuris |
| 4,335,726 A | 6/1982 | Kolstedt |
| 4,336,809 A | 6/1982 | Clark |
| 4,364,015 A | 12/1982 | Drake et al. |
| 4,375,684 A * | 3/1983 | Everett .................. H01S 3/115 372/18 |
| 4,388,924 A | 6/1983 | Weissman et al. |
| 4,409,479 A | 10/1983 | Sprague et al. |
| 4,428,368 A | 1/1984 | Torii |
| 4,435,808 A | 3/1984 | Javan |
| 4,445,217 A | 4/1984 | Acharekar et al. |
| 4,452,081 A | 6/1984 | Seppi |
| 4,456,872 A | 6/1984 | Froeschle |
| 4,461,294 A | 7/1984 | Baron |
| 4,488,104 A | 12/1984 | Suzuki |
| 4,489,415 A | 12/1984 | Jones, Jr. |
| 4,492,601 A | 1/1985 | Nakasone et al. |
| 4,503,854 A | 3/1985 | Jako |
| 4,504,727 A | 3/1985 | Melcher et al. |
| 4,512,197 A | 4/1985 | von Gutfeld et al. |
| 4,524,289 A | 6/1985 | Hammond et al. |
| 4,539,987 A | 9/1985 | Nath et al. |
| 4,553,546 A | 11/1985 | Javelle |
| 4,555,786 A | 11/1985 | Byer |
| 4,556,979 A | 12/1985 | Scott et al. |
| 4,559,943 A | 12/1985 | Bowers |
| 4,561,440 A | 12/1985 | Kubo et al. |
| 4,566,271 A | 1/1986 | French et al. |
| 4,566,438 A | 1/1986 | Liese et al. |
| 4,569,345 A | 2/1986 | Manes |
| 4,576,177 A | 3/1986 | Webster, Jr. |
| 4,587,968 A | 5/1986 | Price |
| 4,591,762 A | 5/1986 | Nakamura |
| 4,592,353 A | 6/1986 | Daikuzono |
| 4,601,037 A | 7/1986 | McDonald |
| 4,601,753 A | 7/1986 | Soileau et al. |
| 4,608,978 A | 9/1986 | Rohr |
| 4,608,979 A | 9/1986 | Breidenthal et al. |
| 4,617,926 A | 10/1986 | Sutton |
| 4,623,929 A | 11/1986 | Johnson et al. |
| 4,629,884 A | 12/1986 | Bergstrom |
| 4,638,800 A | 1/1987 | Michel |
| 4,653,495 A | 3/1987 | Nanaumi |
| 4,656,641 A | 4/1987 | Scifres et al. |
| 4,662,368 A | 5/1987 | Hussein et al. |
| 4,677,347 A | 6/1987 | Nakamura |
| 4,686,986 A | 8/1987 | Fenyo et al. |
| 4,693,244 A | 9/1987 | Daikuzono |
| 4,693,556 A | 9/1987 | McCaughan, Jr. |
| 4,695,697 A | 9/1987 | Kosa |
| 4,710,677 A | 12/1987 | Halberstadt et al. |
| 4,718,416 A | 1/1988 | Nanaumi |
| 4,724,835 A | 2/1988 | Liss et al. |
| 4,733,660 A | 3/1988 | Itzkan |
| 4,735,201 A | 4/1988 | O'Reilly |
| 4,736,743 A | 4/1988 | Daikuzono |
| 4,736,745 A | 4/1988 | Gluckman |
| 4,740,047 A | 4/1988 | Abe et al. |
| 4,741,338 A | 5/1988 | Miyamae |
| 4,745,909 A | 5/1988 | Pelton et al. |
| 4,747,660 A | 5/1988 | Nishioka et al. |
| 4,749,913 A | 6/1988 | Stuermer et al. |
| 4,759,349 A | 7/1988 | Betz et al. |
| 4,773,413 A | 9/1988 | Hussein et al. |
| 4,775,361 A | 10/1988 | Jacques et al. |
| 4,779,173 A | 10/1988 | Carr et al. |
| 4,784,135 A | 11/1988 | Blum et al. |
| 4,799,479 A | 1/1989 | Spears |
| 4,813,412 A | 3/1989 | Yamazaki et al. |

(56) References Cited

U.S. PATENT DOCUMENTS

| | | |
|---|---|---|
| 4,813,762 A | 3/1989 | Leger et al. |
| 4,819,669 A | 4/1989 | Politzer |
| 4,826,431 A | 5/1989 | Fujimura et al. |
| 4,829,262 A | 5/1989 | Furumoto |
| 4,832,024 A | 5/1989 | Boussignac et al. |
| 4,840,174 A | 6/1989 | Gluckman |
| 4,840,563 A | 6/1989 | Altendorf |
| 4,845,608 A | 7/1989 | Gdula |
| 4,848,339 A | 7/1989 | Rink et al. |
| 4,852,107 A | 7/1989 | Hamal et al. |
| 4,852,549 A | 8/1989 | Mori |
| 4,860,172 A | 8/1989 | Schlager et al. |
| 4,860,303 A | 8/1989 | Russell |
| 4,860,743 A | 8/1989 | Abela |
| 4,860,744 A | 8/1989 | Johnson et al. |
| 4,862,886 A | 9/1989 | Clarke et al. |
| 4,862,888 A | 9/1989 | Yessik |
| 4,862,903 A | 9/1989 | Campbell |
| 4,871,479 A | 10/1989 | Bachelard et al. |
| 4,878,224 A | 10/1989 | Kuder et al. |
| 4,884,560 A | 12/1989 | Kuracina |
| 4,887,600 A | 12/1989 | Watson et al. |
| 4,889,525 A | 12/1989 | Yuhas et al. |
| 4,890,898 A | 1/1990 | Bentley et al. |
| 4,891,817 A | 1/1990 | Duarte |
| 4,894,837 A | 1/1990 | DiFonzo et al. |
| 4,896,329 A | 1/1990 | Knaak |
| 4,898,438 A | 2/1990 | Mori |
| 4,898,439 A | 2/1990 | Mori |
| 4,901,323 A | 2/1990 | Hawkins et al. |
| 4,905,690 A | 3/1990 | Ohshiro et al. |
| 4,910,438 A | 3/1990 | Farnsworth |
| 4,913,142 A | 4/1990 | Kittrell et al. |
| 4,914,298 A | 4/1990 | Quad et al. |
| 4,917,084 A | 4/1990 | Sinofsky |
| 4,926,227 A | 5/1990 | Jensen |
| 4,928,038 A | 5/1990 | Nerone |
| 4,930,504 A | 6/1990 | Diamantopoulos et al. |
| 4,931,053 A | 6/1990 | L'Esperance, Jr. |
| 4,932,954 A | 6/1990 | Wondrazek et al. |
| 4,945,239 A | 7/1990 | Wist et al. |
| 4,950,266 A | 8/1990 | Sinofsky |
| 4,955,882 A | 9/1990 | Hakky |
| 4,968,314 A | 11/1990 | Michaels |
| 4,972,427 A | 11/1990 | Streifer et al. |
| 4,973,848 A | 11/1990 | Kolobanov et al. |
| 4,976,308 A | 12/1990 | Faghri |
| 4,976,709 A | 12/1990 | Sand |
| 4,977,571 A | 12/1990 | Furumoto et al. |
| 4,978,186 A | 12/1990 | Mori |
| 4,979,180 A | 12/1990 | Muncheryan |
| 4,992,256 A | 2/1991 | Skaggs et al. |
| 4,994,060 A | 2/1991 | Rink et al. |
| 5,000,752 A | 3/1991 | Hoskin et al. |
| 5,006,293 A | 4/1991 | Hartman et al. |
| 5,009,658 A | 4/1991 | Damgaard-Iversen et al. |
| 5,011,483 A | 4/1991 | Sleister |
| 5,027,359 A | 6/1991 | Leger et al. |
| 5,030,090 A | 7/1991 | Maeda et al. |
| 5,032,178 A | 7/1991 | Cornell |
| 5,037,421 A | 8/1991 | Boutacoff et al. |
| 5,041,109 A | 8/1991 | Abela |
| 5,046,494 A | 9/1991 | Searfoss et al. |
| 5,050,597 A | 9/1991 | Daikuzono |
| 5,056,515 A | 10/1991 | Abel |
| 5,057,099 A | 10/1991 | Rink |
| 5,057,104 A | 10/1991 | Chess |
| 5,059,192 A | 10/1991 | Zaias |
| 5,060,243 A | 10/1991 | Eckert |
| 5,061,266 A | 10/1991 | Hakky |
| 5,065,515 A | 11/1991 | Iderosa |
| 5,066,292 A | 11/1991 | Muller et al. |
| 5,066,293 A | 11/1991 | Furumoto |
| 5,071,416 A | 12/1991 | Heller et al. |
| 5,071,417 A | 12/1991 | Sinofsky |
| 5,080,660 A | 1/1992 | Buelna |
| 5,090,019 A | 2/1992 | Scheps |
| 5,092,865 A | 3/1992 | Rink |
| 5,099,231 A | 3/1992 | Sato et al. |
| 5,102,410 A | 4/1992 | Dressel |
| 5,108,388 A | 4/1992 | Trokel |
| 5,109,387 A | 4/1992 | Garden et al. |
| 5,112,328 A | 5/1992 | Taboada et al. |
| 5,127,395 A | 7/1992 | Bontemps |
| 5,129,896 A | 7/1992 | Hasson |
| 5,129,897 A | 7/1992 | Daikuzono |
| 5,132,980 A | 7/1992 | Connors et al. |
| 5,133,102 A | 7/1992 | Sakuma |
| 5,137,530 A | 8/1992 | Sand |
| 5,140,608 A | 8/1992 | Karpol et al. |
| 5,140,984 A | 8/1992 | Dew et al. |
| 5,147,353 A | 9/1992 | Everett |
| 5,147,356 A | 9/1992 | Bhatta |
| 5,151,097 A | 9/1992 | Daikuzono |
| 5,159,601 A | 10/1992 | Huber |
| 5,160,194 A | 11/1992 | Feldman |
| 5,163,935 A | 11/1992 | Black et al. |
| 5,171,564 A | 12/1992 | Nathoo et al. |
| 5,178,617 A | 1/1993 | Kuizenga et al. |
| 5,180,378 A | 1/1993 | Kung et al. |
| 5,182,557 A | 1/1993 | Lang |
| 5,182,857 A | 2/1993 | Simon |
| 5,190,541 A | 3/1993 | Abele et al. |
| 5,191,883 A | 3/1993 | Lennox et al. |
| 5,192,278 A | 3/1993 | Hayes et al. |
| 5,193,526 A | 3/1993 | Daikuzono |
| 5,196,004 A | 3/1993 | Sinofsky |
| 5,197,470 A | 3/1993 | Helfer et al. |
| 5,201,731 A | 4/1993 | Hakky |
| 5,207,671 A | 5/1993 | Franken et al. |
| 5,207,672 A | 5/1993 | Roth et al. |
| 5,207,673 A | 5/1993 | Ebling et al. |
| 5,209,748 A | 5/1993 | Daikuzono |
| 5,213,092 A | 5/1993 | Uram |
| 5,217,455 A | 6/1993 | Tan |
| 5,219,347 A | 6/1993 | Negus et al. |
| 5,222,907 A | 6/1993 | Katabuchi et al. |
| 5,222,953 A | 6/1993 | Dowlatshahi |
| 5,225,926 A | 7/1993 | Cuomo et al. |
| 5,226,907 A | 7/1993 | Tankovich |
| 5,242,437 A | 9/1993 | Everett et al. |
| 5,242,438 A | 9/1993 | Saadatmanesh et al. |
| 5,246,436 A | 9/1993 | Rowe |
| 5,249,192 A | 9/1993 | Kuizenga et al. |
| 5,254,114 A | 10/1993 | Reed, Jr. et al. |
| 5,255,277 A | 10/1993 | Carvalho |
| 5,257,970 A | 11/1993 | Dougherty |
| 5,257,991 A | 11/1993 | Fletcher et al. |
| 5,261,904 A | 11/1993 | Baker et al. |
| 5,267,399 A | 12/1993 | Johnston |
| 5,267,995 A | 12/1993 | Doiron et al. |
| 5,267,998 A | 12/1993 | Hagen |
| 5,269,777 A | 12/1993 | Doiron et al. |
| 5,269,780 A | 12/1993 | Roos |
| 5,281,211 A | 1/1994 | Panel et al. |
| 5,281,216 A | 1/1994 | Klicek |
| 5,282,797 A | 2/1994 | Chess |
| 5,284,154 A | 2/1994 | Raymond et al. |
| 5,287,372 A | 2/1994 | Ortiz |
| 5,287,380 A | 2/1994 | Hsia |
| 5,290,273 A | 3/1994 | Tan |
| 5,290,274 A | 3/1994 | Levy et al. |
| 5,292,320 A | 3/1994 | Brown et al. |
| 5,293,880 A | 3/1994 | Levitt |
| 5,300,063 A | 4/1994 | Tano et al. |
| 5,300,065 A | 4/1994 | Anderson |
| 5,300,097 A | 4/1994 | Lerner et al. |
| 5,303,585 A | 4/1994 | Lichte |
| 5,304,167 A | 4/1994 | Freiberg |
| 5,304,170 A | 4/1994 | Green |
| 5,304,173 A | 4/1994 | Kittrell et al. |
| 5,306,143 A | 4/1994 | Levy |
| 5,306,274 A | 4/1994 | Long |
| 5,307,369 A | 4/1994 | Kimberlin |

(56) References Cited

U.S. PATENT DOCUMENTS

| | | |
|---|---|---|
| 5,308,311 A | 5/1994 | Eggers et al. |
| 5,312,395 A | 5/1994 | Tan et al. |
| 5,312,396 A | 5/1994 | Feld et al. |
| 5,320,618 A | 6/1994 | Gustafsson |
| 5,320,620 A | 6/1994 | Long et al. |
| 5,330,470 A | 7/1994 | Hagen |
| 5,331,649 A | 7/1994 | Dacquay et al. |
| 5,334,191 A | 8/1994 | Poppas et al. |
| 5,334,193 A | 8/1994 | Nardella |
| 5,336,217 A | 8/1994 | Buys et al. |
| 5,336,221 A | 8/1994 | Anderson |
| 5,342,358 A | 8/1994 | Daikuzono |
| 5,344,418 A | 9/1994 | Ghaffar |
| 5,344,434 A | 9/1994 | Talmore |
| 5,346,488 A | 9/1994 | Prince et al. |
| 5,348,551 A | 9/1994 | Spears et al. |
| 5,349,590 A | 9/1994 | Amirkhanian et al. |
| 5,350,376 A | 9/1994 | Brown |
| 5,353,020 A | 10/1994 | Schumann |
| 5,353,790 A | 10/1994 | Jacques et al. |
| 5,354,294 A | 10/1994 | Chou |
| 5,356,081 A | 10/1994 | Sellar |
| 5,358,503 A | 10/1994 | Bertwell et al. |
| 5,360,426 A | 11/1994 | Muller et al. |
| 5,366,456 A | 11/1994 | Rink et al. |
| 5,368,031 A | 11/1994 | Cline et al. |
| 5,368,038 A | 11/1994 | Fraden |
| 5,369,496 A | 11/1994 | Alfano et al. |
| 5,369,831 A | 12/1994 | Bock |
| 5,370,642 A | 12/1994 | Keller |
| 5,370,649 A | 12/1994 | Gardetto et al. |
| 5,380,317 A | 1/1995 | Everett et al. |
| 5,383,876 A | 1/1995 | Nardella |
| 5,386,427 A | 1/1995 | Zayhowski |
| 5,387,211 A | 2/1995 | Saadatmanesh et al. |
| 5,395,356 A | 3/1995 | King et al. |
| 5,403,306 A | 4/1995 | Edwards et al. |
| 5,405,368 A | 4/1995 | Eckhouse |
| 5,409,446 A | 4/1995 | Rattner |
| 5,409,479 A | 4/1995 | Dew et al. |
| 5,409,481 A | 4/1995 | Poppas et al. |
| 5,415,654 A | 5/1995 | Daikuzono |
| 5,421,337 A | 6/1995 | Richards-Kortum et al. |
| 5,421,339 A | 6/1995 | Ramanujam et al. |
| 5,422,112 A | 6/1995 | Williams |
| 5,423,800 A | 6/1995 | Ren et al. |
| 5,423,803 A | 6/1995 | Tankovich et al. |
| 5,423,805 A | 6/1995 | Brucker et al. |
| 5,425,728 A | 6/1995 | Tankovich |
| 5,425,735 A | 6/1995 | Rosen et al. |
| 5,425,754 A | 6/1995 | Braun et al. |
| 5,439,954 A | 8/1995 | Bush |
| 5,441,499 A | 8/1995 | Fritzsch |
| 5,445,608 A | 8/1995 | Chen et al. |
| 5,445,611 A | 8/1995 | Eppstein et al. |
| 5,454,807 A | 10/1995 | Lennox et al. |
| 5,456,682 A | 10/1995 | Edwards et al. |
| 5,458,140 A | 10/1995 | Eppstein et al. |
| 5,464,436 A | 11/1995 | Smith |
| 5,464,724 A | 11/1995 | Akiyama et al. |
| 5,470,331 A | 11/1995 | Daikuzono |
| 5,472,748 A | 12/1995 | Wolfe et al. |
| 5,474,549 A | 12/1995 | Ortiz et al. |
| 5,484,436 A | 1/1996 | Eggers et al. |
| 5,486,170 A | 1/1996 | Winston et al. |
| 5,486,172 A | 1/1996 | Chess |
| 5,488,626 A | 1/1996 | Heller et al. |
| 5,489,256 A | 2/1996 | Adair |
| 5,492,894 A | 2/1996 | Bascom et al. |
| 5,496,305 A | 3/1996 | Kittrell et al. |
| 5,496,307 A | 3/1996 | Daikuzono |
| 5,498,935 A | 3/1996 | McMahan et al. |
| 5,499,313 A | 3/1996 | Kleinerman |
| 5,501,680 A | 3/1996 | Kurtz et al. |
| 5,502,582 A | 3/1996 | Larson et al. |
| 5,505,726 A | 4/1996 | Meserol |
| 5,505,727 A | 4/1996 | Keller |
| 5,507,739 A | 4/1996 | Vassiliadis et al. |
| 5,519,534 A | 5/1996 | Smith et al. |
| 5,521,367 A | 5/1996 | Bard et al. |
| 5,522,813 A | 6/1996 | Trelles |
| 5,527,350 A | 6/1996 | Grove et al. |
| 5,527,368 A | 6/1996 | Supkis et al. |
| 5,530,711 A | 6/1996 | Scheps |
| 5,531,739 A | 7/1996 | Trelles |
| 5,531,740 A | 7/1996 | Black |
| 5,536,168 A | 7/1996 | Bourke |
| 5,540,676 A | 7/1996 | Freiberg |
| 5,540,678 A | 7/1996 | Long et al. |
| 5,540,681 A | 7/1996 | Strul et al. |
| 5,541,948 A | 7/1996 | Krupke et al. |
| 5,546,214 A | 8/1996 | Black et al. |
| 5,549,660 A | 8/1996 | Mendes et al. |
| 5,557,625 A | 9/1996 | Durville |
| 5,558,666 A | 9/1996 | Dewey et al. |
| 5,558,667 A | 9/1996 | Yarborough et al. |
| 5,561,881 A | 10/1996 | Klinger et al. |
| 5,571,098 A | 11/1996 | Domankevitz et al. |
| 5,578,029 A | 11/1996 | Trelles et al. |
| 5,578,866 A | 11/1996 | DePoorter et al. |
| 5,595,568 A | 1/1997 | Anderson et al. |
| 5,598,426 A | 1/1997 | Hsia et al. |
| 5,608,210 A | 3/1997 | Esparza et al. |
| 5,611,793 A | 3/1997 | Wilson et al. |
| 5,616,140 A | 4/1997 | Prescott |
| 5,618,284 A | 4/1997 | Sand |
| 5,620,478 A | 4/1997 | Eckhouse |
| 5,624,435 A | 4/1997 | Furumoto et al. |
| 5,626,631 A | 5/1997 | Eckhouse |
| 5,628,744 A | 5/1997 | Coleman et al. |
| 5,628,771 A | 5/1997 | Mizukawa et al. |
| 5,630,811 A | 5/1997 | Miller |
| 5,632,741 A | 5/1997 | Zavislan et al. |
| 5,634,711 A | 6/1997 | Kennedy et al. |
| 5,647,866 A | 7/1997 | Zaias et al. |
| 5,649,972 A | 7/1997 | Hochstein |
| 5,651,783 A | 7/1997 | Reynard |
| 5,652,481 A | 7/1997 | Johnson et al. |
| 5,653,706 A | 8/1997 | Zavislan et al. |
| 5,655,547 A | 8/1997 | Karni |
| 5,657,760 A | 8/1997 | Ying et al. |
| 5,658,148 A | 8/1997 | Neuberger et al. |
| 5,658,323 A | 8/1997 | Miller |
| 5,660,836 A | 8/1997 | Knowlton |
| 5,661,744 A | 8/1997 | Murakami et al. |
| 5,662,643 A | 9/1997 | Kung et al. |
| 5,662,644 A | 9/1997 | Swor |
| 5,668,824 A | 9/1997 | Furumoto et al. |
| 5,671,315 A | 9/1997 | Tabuchi et al. |
| 5,673,451 A | 10/1997 | Moore et al. |
| 5,679,113 A | 10/1997 | Caisey et al. |
| 5,683,380 A | 11/1997 | Eckhouse et al. |
| 5,684,902 A | 11/1997 | Tada |
| 5,688,266 A | 11/1997 | Edwards et al. |
| 5,688,267 A | 11/1997 | Panescu et al. |
| 5,692,509 A | 12/1997 | Voss et al. |
| 5,698,866 A | 12/1997 | Doiron et al. |
| 5,707,369 A | 1/1998 | Vaitekunas et al. |
| 5,707,401 A | 1/1998 | Talmore |
| 5,707,403 A | 1/1998 | Grove et al. |
| 5,713,738 A | 2/1998 | Yarborough |
| 5,714,119 A | 2/1998 | Kawagoe et al. |
| 5,720,772 A | 2/1998 | Eckhouse |
| 5,720,894 A | 2/1998 | Neev et al. |
| 5,722,397 A | 3/1998 | Eppstein |
| 5,725,522 A | 3/1998 | Sinofsky |
| 5,728,090 A | 3/1998 | Martin et al. |
| 5,735,844 A | 4/1998 | Anderson et al. |
| 5,735,884 A | 4/1998 | Thompson et al. |
| 5,738,678 A | 4/1998 | Patel |
| 5,742,392 A | 4/1998 | Anderson et al. |
| 5,743,901 A | 4/1998 | Grove et al. |
| 5,743,902 A | 4/1998 | Trost |
| 5,746,735 A | 5/1998 | Furumoto et al. |

(56) References Cited

U.S. PATENT DOCUMENTS

| | | |
|---|---|---|
| 5,748,822 A | 5/1998 | Miura et al. |
| 5,749,868 A | 5/1998 | Furumoto |
| 5,755,751 A | 5/1998 | Eckhouse |
| 5,759,162 A | 6/1998 | Oppelt et al. |
| 5,759,200 A | 6/1998 | Azar |
| 5,760,362 A | 6/1998 | Eloy |
| 5,769,076 A | 6/1998 | Maekawa et al. |
| 5,776,129 A | 7/1998 | Mersch |
| 5,782,249 A | 7/1998 | Weber et al. |
| 5,802,136 A | 9/1998 | Carol |
| 5,807,386 A | 9/1998 | Slatkine et al. |
| 5,810,801 A | 9/1998 | Anderson et al. |
| 5,810,802 A | 9/1998 | Panescu et al. |
| 5,812,567 A | 9/1998 | Jeon et al. |
| 5,813,855 A | 9/1998 | Crisio, Jr. |
| 5,814,008 A | 9/1998 | Chen et al. |
| 5,814,040 A | 9/1998 | Nelson et al. |
| 5,814,041 A | 9/1998 | Anderson et al. |
| 5,817,089 A | 10/1998 | Tankovich et al. |
| 5,818,580 A | 10/1998 | Murnick |
| 5,820,625 A | 10/1998 | Izawa et al. |
| 5,820,626 A | 10/1998 | Baumgardner |
| 5,822,034 A | 10/1998 | Shimashita et al. |
| 5,824,023 A | 10/1998 | Anderson |
| 5,827,264 A | 10/1998 | Hohla |
| 5,828,803 A | 10/1998 | Eckhouse |
| 5,830,208 A | 11/1998 | Muller |
| 5,830,209 A | 11/1998 | Savage et al. |
| 5,835,648 A | 11/1998 | Narciso, Jr. et al. |
| 5,836,877 A | 11/1998 | Zavislan |
| 5,836,999 A | 11/1998 | Eckhouse et al. |
| 5,837,001 A | 11/1998 | Mackey |
| 5,840,048 A | 11/1998 | Cheng |
| 5,843,072 A | 12/1998 | Furumoto et al. |
| 5,849,029 A | 12/1998 | Eckhouse et al. |
| 5,851,181 A | 12/1998 | Talmor |
| 5,853,407 A | 12/1998 | Miller |
| 5,860,967 A | 1/1999 | Zavislan et al. |
| 5,868,731 A | 2/1999 | Budnik et al. |
| 5,868,732 A | 2/1999 | Waldman et al. |
| 5,871,479 A | 2/1999 | Furumoto et al. |
| 5,871,480 A | 2/1999 | Tankovich |
| 5,879,159 A | 3/1999 | Cipolla |
| 5,879,346 A | 3/1999 | Waldman et al. |
| 5,879,376 A | 3/1999 | Miller |
| 5,883,471 A | 3/1999 | Rodman et al. |
| 5,885,211 A | 3/1999 | Eppstein et al. |
| 5,885,273 A | 3/1999 | Eckhouse et al. |
| 5,885,274 A | 3/1999 | Fullmer et al. |
| 5,891,063 A | 4/1999 | Vigil |
| 5,893,828 A | 4/1999 | Uram |
| 5,893,885 A | 4/1999 | Webster, Jr. |
| 5,895,350 A | 4/1999 | Hori |
| 5,897,549 A | 4/1999 | Tankovich |
| 5,906,609 A | 5/1999 | Assa et al. |
| 5,908,418 A | 6/1999 | Dority et al. |
| 5,908,731 A | 6/1999 | Leenders et al. |
| 5,913,883 A | 6/1999 | Alexander et al. |
| 5,916,211 A | 6/1999 | Quon et al. |
| 5,919,601 A | 7/1999 | Nguyen et al. |
| 5,920,374 A | 7/1999 | Vaphiades et al. |
| 5,921,926 A | 7/1999 | Rolland et al. |
| 5,928,222 A | 7/1999 | Kleinerman |
| 5,935,124 A | 8/1999 | Klumb et al. |
| 5,944,687 A | 8/1999 | Benett et al. |
| 5,944,748 A | 8/1999 | Mager et al. |
| 5,948,011 A | 9/1999 | Knowlton |
| 5,948,596 A | 9/1999 | Zhong et al. |
| 5,949,222 A | 9/1999 | Buono |
| 5,951,543 A | 9/1999 | Brauer |
| 5,954,710 A | 9/1999 | Paolini et al. |
| 5,955,490 A | 9/1999 | Kennedy et al. |
| 5,957,915 A | 9/1999 | Trost |
| 5,964,749 A | 10/1999 | Eckhouse et al. |
| 5,968,033 A | 10/1999 | Fuller et al. |
| 5,968,034 A | 10/1999 | Fullmer et al. |
| 5,971,976 A | 10/1999 | Wang et al. |
| 5,974,059 A | 10/1999 | Dawson |
| 5,974,616 A | 11/1999 | Dreyfus |
| 5,976,123 A | 11/1999 | Baumgardner et al. |
| 5,977,723 A | 11/1999 | Yoon |
| 5,979,454 A | 11/1999 | Anvari et al. |
| 5,983,900 A | 11/1999 | Clement et al. |
| 5,984,915 A | 11/1999 | Loeb et al. |
| 6,004,723 A | 12/1999 | Figov |
| 6,007,219 A | 12/1999 | O'Meara |
| 6,015,404 A | 1/2000 | Altshuler et al. |
| 6,017,677 A | 1/2000 | Maemoto et al. |
| 6,022,316 A | 2/2000 | Eppstein et al. |
| 6,022,346 A | 2/2000 | Panescu et al. |
| 6,024,095 A | 2/2000 | Stanley, III |
| 6,026,828 A | 2/2000 | Altshuler |
| 6,027,493 A | 2/2000 | Donitzky et al. |
| 6,027,495 A | 2/2000 | Miller |
| 6,028,694 A | 2/2000 | Schmidt |
| 6,029,303 A | 2/2000 | Dewan |
| 6,029,304 A | 2/2000 | Hulke et al. |
| 6,030,378 A | 2/2000 | Stewart |
| 6,030,399 A | 2/2000 | Ignotz et al. |
| 6,032,071 A | 2/2000 | Binder |
| RE36,634 E | 3/2000 | Ghaffari |
| 6,033,431 A | 3/2000 | Segal |
| 6,036,684 A | 3/2000 | Tankovich et al. |
| 6,044,514 A | 4/2000 | Kaneda et al. |
| 6,045,548 A | 4/2000 | Furumoto et al. |
| 6,050,990 A | 4/2000 | Tankovich et al. |
| D424,197 S | 5/2000 | Sydlowski et al. |
| 6,056,548 A | 5/2000 | Neuberger et al. |
| 6,056,738 A | 5/2000 | Marchitto et al. |
| 6,058,937 A | 5/2000 | Doiron et al. |
| 6,059,820 A | 5/2000 | Baronov |
| 6,063,108 A | 5/2000 | Salansky et al. |
| 6,068,963 A | 5/2000 | Aoshima |
| 6,070,092 A | 5/2000 | Kazama et al. |
| 6,071,239 A | 6/2000 | Cribbs et al. |
| 6,074,382 A | 6/2000 | Asah et al. |
| 6,077,294 A | 6/2000 | Cho et al. |
| 6,080,146 A | 6/2000 | Altshuler et al. |
| 6,080,147 A | 6/2000 | Tobinick |
| 6,083,217 A | 7/2000 | Tankovich |
| 6,086,363 A | 7/2000 | Moran et al. |
| 6,086,558 A | 7/2000 | Bower et al. |
| 6,086,580 A | 7/2000 | Mordon et al. |
| 6,090,524 A | 7/2000 | Deboer et al. |
| 6,094,767 A | 8/2000 | Iimura |
| 6,096,028 A | 8/2000 | Bahmanyar et al. |
| 6,096,029 A | 8/2000 | O'Donnell, Jr. |
| 6,096,209 A | 8/2000 | O'Brien et al. |
| 6,099,521 A | 8/2000 | Shadduck |
| 6,101,207 A | 8/2000 | Ilorinne |
| 6,104,959 A | 8/2000 | Spertell |
| 6,106,293 A | 8/2000 | Wiesel |
| 6,106,294 A | 8/2000 | Daniel |
| 6,110,195 A | 8/2000 | Xie et al. |
| 6,112,123 A | 8/2000 | Kelleher et al. |
| 6,113,559 A | 9/2000 | Klopotek |
| 6,117,129 A | 9/2000 | Mukai |
| 6,120,497 A | 9/2000 | Anderson et al. |
| 6,126,655 A | 10/2000 | Domankevitz et al. |
| 6,129,723 A | 10/2000 | Anderson et al. |
| 6,132,929 A | 10/2000 | Nakamura et al. |
| 6,135,774 A | 10/2000 | Hack et al. |
| 6,142,650 A | 11/2000 | Brown et al. |
| 6,142,939 A | 11/2000 | Eppstein et al. |
| 6,149,644 A | 11/2000 | Xie |
| 6,149,895 A | 11/2000 | Kutsch |
| 6,153,352 A | 11/2000 | Oohashi et al. |
| 6,156,030 A | 12/2000 | Neev |
| 6,159,203 A | 12/2000 | Sinofsky |
| 6,159,236 A | 12/2000 | Biel |
| 6,162,055 A | 12/2000 | Montgomery et al. |
| 6,162,211 A | 12/2000 | Tankovich et al. |
| 6,162,212 A | 12/2000 | Kreindel et al. |
| 6,162,215 A | 12/2000 | Feng |

(56) References Cited

U.S. PATENT DOCUMENTS

| | | |
|---|---|---|
| 6,162,218 A | 12/2000 | Elbrecht et al. |
| 6,164,837 A | 12/2000 | Haake et al. |
| 6,171,300 B1 | 1/2001 | Adams |
| 6,171,301 B1 | 1/2001 | Nelson et al. |
| 6,171,302 B1 | 1/2001 | Talpalriu et al. |
| 6,171,332 B1 | 1/2001 | Whitehurst |
| 6,173,202 B1 | 1/2001 | Eppstein |
| 6,174,325 B1 | 1/2001 | Eckhouse |
| 6,176,854 B1 | 1/2001 | Cone |
| 6,177,230 B1 | 1/2001 | Kawamura |
| 6,183,434 B1 | 2/2001 | Eppstein |
| 6,183,500 B1 | 2/2001 | Kohler |
| 6,183,773 B1 | 2/2001 | Anderson |
| 6,187,001 B1 | 2/2001 | Azar et al. |
| 6,187,029 B1 | 2/2001 | Shapiro et al. |
| 6,190,825 B1 | 2/2001 | Denzinger et al. |
| 6,190,831 B1 | 2/2001 | Leon et al. |
| 6,197,020 B1 | 3/2001 | O'Donnell, Jr. |
| 6,200,134 B1 | 3/2001 | Kovac et al. |
| 6,200,309 B1 | 3/2001 | Rice et al. |
| 6,202,242 B1 | 3/2001 | Salmon et al. |
| 6,203,540 B1 | 3/2001 | Weber |
| 6,208,458 B1 | 3/2001 | Galvanauskas et al. |
| 6,210,425 B1 | 4/2001 | Chen |
| 6,210,426 B1 | 4/2001 | Cho et al. |
| 6,214,034 B1 | 4/2001 | Azar |
| 6,221,068 B1 | 4/2001 | Fried et al. |
| 6,221,095 B1 | 4/2001 | Van Zuylen et al. |
| 6,228,074 B1 | 5/2001 | Almeida |
| 6,228,075 B1 | 5/2001 | Furumoto |
| 6,229,831 B1 | 5/2001 | Nightingale et al. |
| 6,233,584 B1 | 5/2001 | Purcell |
| 6,235,015 B1 | 5/2001 | Mead, III et al. |
| 6,235,016 B1 | 5/2001 | Stewart |
| 6,236,891 B1 | 5/2001 | Ingle et al. |
| 6,238,839 B1 | 5/2001 | Tomita et al. |
| 6,239,442 B1 | 5/2001 | Iimura |
| 6,240,306 B1 | 5/2001 | Rohrscheib et al. |
| 6,240,925 B1 | 6/2001 | McMillan et al. |
| 6,245,093 B1 | 6/2001 | Li et al. |
| 6,245,486 B1 | 6/2001 | Teng |
| 6,246,710 B1 | 6/2001 | Furumoto et al. |
| 6,248,103 B1 | 6/2001 | Tannenbaum et al. |
| 6,248,503 B1 | 6/2001 | Vermeersch et al. |
| 6,251,127 B1 | 6/2001 | Biel |
| 6,254,388 B1 | 7/2001 | Yarborough |
| 6,261,740 B1 | 7/2001 | Nguyen et al. |
| 6,263,233 B1 | 7/2001 | Zavislan et al. |
| 6,264,649 B1 | 7/2001 | Whitcroft et al. |
| 6,267,779 B1 | 7/2001 | Gerdes |
| 6,267,780 B1 | 7/2001 | Streeter |
| 6,273,883 B1 | 8/2001 | Furumoto |
| 6,273,884 B1 | 8/2001 | Altshuler et al. |
| 6,273,885 B1 | 8/2001 | Koop et al. |
| 6,280,438 B1 | 8/2001 | Eckhouse et al. |
| 6,282,442 B1 | 8/2001 | DeStefano et al. |
| 6,283,956 B1 | 9/2001 | McDaniel |
| 6,287,549 B1 | 9/2001 | Sumian et al. |
| 6,290,496 B1 | 9/2001 | Azar et al. |
| 6,290,712 B1 | 9/2001 | Nordquist et al. |
| 6,290,713 B1 | 9/2001 | Russell |
| 6,294,311 B1 | 9/2001 | Shimazu et al. |
| 6,306,130 B1 | 10/2001 | Anderson et al. |
| 6,306,160 B1 | 10/2001 | Nidetzky |
| 6,315,772 B1 | 11/2001 | Marchitto et al. |
| 6,317,624 B1 | 11/2001 | Kollias et al. |
| 6,319,274 B1 | 11/2001 | Shadduck |
| 6,322,584 B2 | 11/2001 | Ingle et al. |
| 6,325,769 B1 | 12/2001 | Klopotek |
| 6,327,506 B1 | 12/2001 | Yogo et al. |
| 6,328,733 B1 | 12/2001 | Trost |
| 6,331,111 B1 | 12/2001 | Cao |
| 6,332,891 B1 | 12/2001 | Himes |
| 6,338,855 B1 | 1/2002 | Albacarys et al. |
| 6,340,495 B1 | 1/2002 | Sumian et al. |
| 6,343,400 B1 | 2/2002 | Massholder et al. |
| 6,343,933 B1 | 2/2002 | Montgomery et al. |
| 6,346,365 B1 | 2/2002 | Kawauchi et al. |
| 6,350,261 B1 | 2/2002 | Domankevitz et al. |
| 6,350,276 B1 | 2/2002 | Knowlton |
| 6,352,811 B1 | 3/2002 | Patel et al. |
| 6,354,370 B1 | 3/2002 | Miller et al. |
| 6,355,054 B1 | 3/2002 | Neuberger |
| 6,358,242 B1 | 3/2002 | Cecchetti |
| 6,358,272 B1 | 3/2002 | Wilden |
| 6,358,669 B1 | 3/2002 | Savariar-Hauck et al. |
| 6,364,872 B1 | 4/2002 | Hsia et al. |
| 6,383,176 B1 | 5/2002 | Connors et al. |
| 6,383,177 B1 | 5/2002 | Balle-Petersen et al. |
| 6,387,089 B1 | 5/2002 | Kreindel et al. |
| 6,387,353 B1 | 5/2002 | Jensen et al. |
| 6,391,022 B1 | 5/2002 | Furumoto et al. |
| 6,394,949 B1 | 5/2002 | Crowley et al. |
| 6,395,016 B1 | 5/2002 | Oron et al. |
| 6,398,801 B1 | 6/2002 | Clement et al. |
| 6,400,011 B1 | 6/2002 | Miki |
| 6,402,739 B1 | 6/2002 | Neev |
| 6,405,732 B1 | 6/2002 | Edwards et al. |
| 6,406,474 B1 | 6/2002 | Neuberger et al. |
| 6,409,665 B1 | 6/2002 | Scott et al. |
| 6,409,723 B1 | 6/2002 | Edwards |
| 6,413,267 B1 | 7/2002 | Dumoulin-White et al. |
| 6,416,319 B1 | 7/2002 | Cipolla |
| 6,419,389 B1 | 7/2002 | Fuchs et al. |
| 6,423,462 B1 | 7/2002 | Kunita |
| 6,424,852 B1 | 7/2002 | Zavislan |
| 6,425,912 B1 | 7/2002 | Knowlton |
| 6,435,873 B1 | 8/2002 | Burgio |
| 6,436,094 B1 | 8/2002 | Reuter |
| 6,439,888 B1 | 8/2002 | Boutoussov et al. |
| 6,440,155 B1 | 8/2002 | Matsumae et al. |
| 6,440,633 B1 | 8/2002 | Kawauchi |
| 6,443,946 B2 | 9/2002 | Clement et al. |
| 6,443,978 B1 | 9/2002 | Zharov |
| 6,447,503 B1 | 9/2002 | Wynne et al. |
| 6,447,504 B1 | 9/2002 | Ben-Haim et al. |
| 6,451,007 B1 | 9/2002 | Koop et al. |
| 6,454,790 B1 | 9/2002 | Neuberger et al. |
| 6,459,919 B1 | 10/2002 | Lys et al. |
| 6,461,296 B1 | 10/2002 | Desai |
| 6,464,694 B1 | 10/2002 | Massengill |
| 6,468,717 B2 | 10/2002 | Kita et al. |
| 6,470,216 B1 | 10/2002 | Knowlton |
| 6,471,712 B2 | 10/2002 | Burres |
| 6,471,716 B1 | 10/2002 | Pecukonis |
| 6,475,211 B2 | 11/2002 | Chess et al. |
| 6,482,199 B1 | 11/2002 | Neev |
| 6,484,052 B1 | 11/2002 | Visuri et al. |
| 6,485,413 B1 | 11/2002 | Boppart et al. |
| 6,491,685 B2 | 12/2002 | Visuri et al. |
| 6,491,715 B1 | 12/2002 | Abels et al. |
| 6,493,608 B1 | 12/2002 | Niemeyer |
| 6,494,900 B1 | 12/2002 | Salansky et al. |
| 6,497,702 B1 | 12/2002 | Bernaz |
| 6,503,269 B2 | 1/2003 | Nield et al. |
| 6,503,486 B2 | 1/2003 | Xu et al. |
| 6,508,785 B1 | 1/2003 | Eppstein |
| 6,508,813 B1 | 1/2003 | Altshuler |
| 6,511,475 B1 | 1/2003 | Altshuler et al. |
| 6,514,243 B1 | 2/2003 | Eckhouse et al. |
| 6,517,532 B1 | 2/2003 | Altshuler et al. |
| 6,519,376 B2 | 2/2003 | Biagi et al. |
| 6,525,819 B1 | 2/2003 | Delawter et al. |
| 6,527,716 B1 | 3/2003 | Eppstein |
| 6,527,764 B1 | 3/2003 | Neuberger et al. |
| 6,529,540 B1 * | 3/2003 | Demmer ............ H01S 3/1075 372/27 |
| 6,530,915 B1 | 3/2003 | Eppstein et al. |
| 6,530,916 B1 | 3/2003 | Shimmick |
| 6,537,270 B1 | 3/2003 | Elbrecht et al. |
| 6,544,257 B2 | 4/2003 | Nagase et al. |
| 6,547,780 B1 | 4/2003 | Sinofsky |
| 6,551,346 B2 | 4/2003 | Crossley |
| 6,554,439 B1 | 4/2003 | Teicher et al. |

(56) References Cited

U.S. PATENT DOCUMENTS

| | | |
|---|---|---|
| 6,556,596 B1 | 4/2003 | Kim et al. |
| 6,558,372 B1 | 5/2003 | Altshuler |
| 6,561,808 B2 | 5/2003 | Neuberger |
| 6,569,155 B1 | 5/2003 | Connors et al. |
| 6,570,892 B1 | 5/2003 | Lin et al. |
| 6,570,893 B1 | 5/2003 | Libatique et al. |
| 6,572,634 B2 | 6/2003 | Koo |
| 6,572,637 B1 | 6/2003 | Yamazaki et al. |
| 6,580,732 B1 | 6/2003 | Guch, Jr. et al. |
| 6,595,934 B1 | 7/2003 | Hissong et al. |
| 6,600,951 B1 | 7/2003 | Anderson |
| 6,602,245 B1 | 8/2003 | Thiberg |
| 6,602,275 B1 | 8/2003 | Sullivan |
| 6,603,988 B2 | 8/2003 | Dowlatshahi |
| 6,605,080 B1 | 8/2003 | Altshuler et al. |
| 6,605,083 B2 | 8/2003 | Clement et al. |
| 6,606,755 B1 | 8/2003 | Robinson et al. |
| 6,607,525 B2 | 8/2003 | Franco |
| 6,610,052 B2 | 8/2003 | Furumoto |
| 6,613,040 B2 | 9/2003 | Tankovich et al. |
| 6,616,447 B1 | 9/2003 | Rizoiu et al. |
| 6,616,451 B1 | 9/2003 | Rizoiu et al. |
| 6,618,531 B1 | 9/2003 | Goto et al. |
| 6,623,272 B2 | 9/2003 | Clemans |
| 6,623,513 B2 | 9/2003 | Biel |
| 6,629,971 B2 | 10/2003 | McDaniel |
| 6,629,989 B2 | 10/2003 | Akita |
| 6,632,219 B1 | 10/2003 | Baranov et al. |
| 6,635,075 B2 | 10/2003 | Li et al. |
| 6,641,578 B2 | 11/2003 | Mukai |
| 6,641,600 B1 | 11/2003 | Kohler |
| 6,648,904 B2 | 11/2003 | Altshuler et al. |
| 6,652,459 B2 | 11/2003 | Payne et al. |
| 6,653,618 B2 | 11/2003 | Zenzie |
| 6,659,999 B1 | 12/2003 | Anderson et al. |
| 6,660,000 B2 | 12/2003 | Neuberger et al. |
| 6,663,620 B2 | 12/2003 | Altshuler et al. |
| 6,663,658 B1 | 12/2003 | Kollias et al. |
| 6,663,659 B2 | 12/2003 | McDaniel |
| 6,666,856 B2 | 12/2003 | Connors et al. |
| 6,669,685 B1 | 12/2003 | Rizoiu et al. |
| 6,675,425 B1 | 1/2004 | Iimura |
| 6,676,654 B1 | 1/2004 | Balle-Petersen et al. |
| 6,679,837 B2 | 1/2004 | Daikuzono |
| 6,682,523 B2 | 1/2004 | Shadduck |
| 6,682,524 B1 | 1/2004 | Elbrecht et al. |
| 6,685,639 B1 | 2/2004 | Wang et al. |
| 6,685,699 B1 | 2/2004 | Eppstein et al. |
| 6,685,722 B1 | 2/2004 | Rosenbluth et al. |
| 6,689,124 B1 | 2/2004 | Thiberg |
| 6,692,456 B1 | 2/2004 | Eppstein et al. |
| 6,692,517 B2 | 2/2004 | Cho et al. |
| 6,699,040 B1 | 3/2004 | Hahn et al. |
| 6,706,035 B2 | 3/2004 | Cense et al. |
| 6,709,269 B1 | 3/2004 | Altshuler |
| 6,709,446 B2 | 3/2004 | Lundahl et al. |
| 6,723,090 B2 | 4/2004 | Altshuler et al. |
| 6,724,958 B1 | 4/2004 | German et al. |
| 6,726,681 B2 | 4/2004 | Grasso, III et al. |
| 6,736,807 B2 | 5/2004 | Yamazaki et al. |
| 6,743,222 B2 | 6/2004 | Durkin et al. |
| 6,746,444 B2 | 6/2004 | Key |
| 6,749,623 B1 | 6/2004 | Hsi et al. |
| 6,755,647 B2 | 6/2004 | Melikechi et al. |
| 6,770,069 B1 | 8/2004 | Hobart et al. |
| 6,772,053 B2 | 8/2004 | Niemeyer |
| 6,790,205 B1 | 9/2004 | Yamazaki et al. |
| 6,800,122 B2 | 10/2004 | Anderson et al. |
| 6,801,595 B2 | 10/2004 | Grodzins et al. |
| 6,808,331 B2 | 10/2004 | Hall et al. |
| 6,808,532 B2 | 10/2004 | Andersen et al. |
| 6,824,542 B2 | 11/2004 | Jay |
| RE38,670 E | 12/2004 | Asah et al. |
| 6,858,009 B2 | 2/2005 | Kawata et al. |
| 6,860,879 B2 | 3/2005 | Irion et al. |
| 6,860,896 B2 | 3/2005 | Leber et al. |
| 6,862,771 B1 | 3/2005 | Muller |
| 6,863,781 B2 | 3/2005 | Nocera et al. |
| 6,872,203 B2 | 3/2005 | Shalirslein et al. |
| 6,878,144 B2 | 4/2005 | Altshuler et al. |
| 6,881,212 B1 | 4/2005 | Clement et al. |
| 6,887,260 B1 | 5/2005 | McDaniel |
| 6,888,319 B2 | 5/2005 | Inochkin et al. |
| 6,893,259 B1 | 5/2005 | Reizenson |
| 6,902,397 B2 | 6/2005 | Farrell et al. |
| 6,902,563 B2 | 6/2005 | Wilkens et al. |
| 6,905,492 B2 | 6/2005 | Zvuloni et al. |
| 6,916,316 B2 | 7/2005 | Jay |
| 6,936,046 B2 | 8/2005 | Hissong et al. |
| 6,942,658 B1 | 9/2005 | Rizoiu et al. |
| 6,953,341 B2 | 10/2005 | Black |
| 6,974,450 B2 | 12/2005 | Weber et al. |
| 6,974,451 B2 | 12/2005 | Altshuler et al. |
| 6,976,985 B2 | 12/2005 | Altshuler et al. |
| 6,986,903 B2 | 1/2006 | Zulli et al. |
| 6,989,007 B2 | 1/2006 | Shadduck |
| 6,989,023 B2 | 1/2006 | Black |
| 6,991,644 B2 | 1/2006 | Spooner et al. |
| 6,997,923 B2 | 2/2006 | Anderson et al. |
| 7,001,413 B2 | 2/2006 | Butler |
| 7,006,223 B2 | 2/2006 | Mullani |
| 7,006,540 B2 | 2/2006 | Rieger |
| 7,006,874 B2 | 2/2006 | Knowlton et al. |
| 7,018,396 B2 | 3/2006 | Sierra et al. |
| 7,029,469 B2 | 4/2006 | Vasily |
| 7,033,349 B2 | 4/2006 | Key |
| 7,036,516 B1 | 5/2006 | Dees et al. |
| 7,041,094 B2 | 5/2006 | Connors et al. |
| 7,041,100 B2 | 5/2006 | Kreindel |
| 7,044,959 B2 | 5/2006 | Anderson et al. |
| 7,060,061 B2 | 6/2006 | Altshuler et al. |
| 7,066,733 B2 | 6/2006 | Logan et al. |
| 7,070,611 B2 | 7/2006 | Biel |
| 7,077,840 B2 | 7/2006 | Altshuler et al. |
| 7,081,128 B2 | 7/2006 | Hart et al. |
| 7,097,639 B1 | 8/2006 | Almeida |
| 7,097,656 B1 | 8/2006 | Akopov et al. |
| 7,104,985 B2 | 9/2006 | Martinelli |
| 7,118,562 B2 | 10/2006 | Furumoto |
| 7,118,563 B2 | 10/2006 | Weckwerth et al. |
| 7,135,033 B2 | 11/2006 | Altshuler et al. |
| 7,144,247 B2 | 12/2006 | Black |
| 7,144,248 B2 | 12/2006 | Irwin |
| 7,145,105 B2 | 12/2006 | Gaulard |
| 7,145,108 B2 | 12/2006 | Kanel et al. |
| 7,160,289 B2 | 1/2007 | Cohen |
| 7,170,034 B2 | 1/2007 | Shalev et al. |
| 7,175,617 B2 | 2/2007 | Jay |
| 7,182,760 B2 | 2/2007 | Kubota |
| 7,198,634 B2 | 4/2007 | Harth et al. |
| 7,202,446 B2 | 4/2007 | Shalev et al. |
| 7,204,832 B2 | 4/2007 | Altshuler et al. |
| 7,216,055 B1 | 5/2007 | Horton et al. |
| 7,217,265 B2 | 5/2007 | Hennings et al. |
| 7,217,267 B2 | 5/2007 | Jay |
| 7,220,254 B2 | 5/2007 | Altshuler et al. |
| 7,223,270 B2 | 5/2007 | Altshuler et al. |
| 7,223,281 B2 | 5/2007 | Altshuler et al. |
| 7,255,691 B2 | 8/2007 | Tolkoff et al. |
| 7,274,155 B2 | 9/2007 | Inochkin et al. |
| 7,276,058 B2 | 10/2007 | Altshuler et al. |
| 7,280,866 B1 | 10/2007 | McIntosh et al. |
| 7,282,060 B2 | 10/2007 | DeBenedictis et al. |
| 7,282,723 B2 | 10/2007 | Schomacker et al. |
| 7,291,140 B2 | 11/2007 | MacFarland et al. |
| 7,291,141 B2 | 11/2007 | Jay |
| 7,309,335 B2 | 12/2007 | Altshuler et al. |
| 7,311,722 B2 | 12/2007 | Larsen |
| 7,322,972 B2 | 1/2008 | Viator et al. |
| 7,329,273 B2 | 2/2008 | Altshuler et al. |
| 7,329,274 B2 | 2/2008 | Altshuler et al. |
| 7,331,953 B2 | 2/2008 | Manstein et al. |
| 7,331,964 B2 | 2/2008 | Maricle et al. |
| 7,333,698 B2 | 2/2008 | Israel |

(56) References Cited

U.S. PATENT DOCUMENTS

| | | |
|---|---|---|
| 7,333,841 B2 | 2/2008 | Maruo et al. |
| 7,351,252 B2 | 4/2008 | Altshuler et al. |
| 7,354,448 B2 | 4/2008 | Altshuler et al. |
| 7,422,598 B2 | 9/2008 | Altshuler et al. |
| 7,423,767 B2 | 9/2008 | Steinsiek et al. |
| 7,431,719 B2 | 10/2008 | Altshuler et al. |
| 7,436,863 B2 | 10/2008 | Matsuda et al. |
| 7,500,956 B1 | 3/2009 | Wilk |
| 7,531,967 B2 | 5/2009 | Inochkin et al. |
| 7,540,869 B2 | 6/2009 | Altshuler et al. |
| 7,553,308 B2 | 6/2009 | Jay |
| 7,586,957 B2 | 9/2009 | Sierra et al. |
| 7,588,547 B2 | 9/2009 | Deem et al. |
| 7,624,640 B2 | 12/2009 | Maris et al. |
| 7,647,092 B2 | 1/2010 | Motz et al. |
| 7,699,058 B1 | 4/2010 | Jay |
| 7,722,600 B2 | 5/2010 | Connors et al. |
| 7,758,621 B2 | 7/2010 | Altshuler et al. |
| 7,763,016 B2 | 7/2010 | Altshuler et al. |
| 7,839,972 B2 | 11/2010 | Ruchala et al. |
| 7,856,985 B2 | 12/2010 | Mirkov et al. |
| 7,860,554 B2 | 12/2010 | Leonardi et al. |
| 7,929,579 B2 | 4/2011 | Hohm et al. |
| 7,931,028 B2 | 4/2011 | Jay |
| 7,935,107 B2 | 5/2011 | Altshuler et al. |
| 7,938,821 B2 | 5/2011 | Chan et al. |
| 7,942,869 B2 | 5/2011 | Houbolt et al. |
| 7,942,915 B2 | 5/2011 | Altshuler et al. |
| 7,942,916 B2 | 5/2011 | Altshuler et al. |
| 7,998,181 B2 | 8/2011 | Nightingale et al. |
| 8,002,768 B1 | 8/2011 | Altshuler et al. |
| 8,027,710 B1 | 9/2011 | Dannan |
| 8,109,924 B2 | 2/2012 | Altshuler et al. |
| 8,113,209 B2 | 2/2012 | Masotti et al. |
| 8,182,473 B2 | 5/2012 | Altshuler et al. |
| 8,317,779 B2 | 11/2012 | Mirkov et al. |
| 8,322,348 B2 | 12/2012 | Mirkov et al. |
| 8,328,794 B2 | 12/2012 | Altshuler et al. |
| 8,328,796 B2 | 12/2012 | Altshuler et al. |
| 8,346,347 B2 | 1/2013 | Altshuler et al. |
| 8,357,145 B2 | 1/2013 | Schleicher et al. |
| 8,378,322 B2 | 2/2013 | Dahm et al. |
| 8,439,940 B2 | 5/2013 | Chomas et al. |
| 2001/0007068 A1 | 7/2001 | Ota et al. |
| 2001/0008973 A1 | 7/2001 | Van Zuylen et al. |
| 2001/0016732 A1 | 8/2001 | Hobart et al. |
| 2001/0023363 A1 | 9/2001 | Harth et al. |
| 2001/0024777 A1 | 9/2001 | Azar et al. |
| 2001/0025173 A1 | 9/2001 | Ritchie et al. |
| 2001/0029956 A1 | 10/2001 | Argenta et al. |
| 2001/0041886 A1 | 11/2001 | Durkin et al. |
| 2001/0046652 A1 | 11/2001 | Ostler et al. |
| 2001/0048077 A1 | 12/2001 | Afanassieva |
| 2002/0002367 A1 | 1/2002 | Tankovich et al. |
| 2002/0004066 A1 | 1/2002 | Stanley et al. |
| 2002/0005475 A1 | 1/2002 | Zenzie |
| 2002/0013572 A1 | 1/2002 | Berlin |
| 2002/0015911 A1 | 2/2002 | Nakamura |
| 2002/0016587 A1 | 2/2002 | Furumoto |
| 2002/0018754 A1 | 2/2002 | Sagel et al. |
| 2002/0019624 A1 | 2/2002 | Clement et al. |
| 2002/0019625 A1 | 2/2002 | Azar |
| 2002/0026225 A1 | 2/2002 | Segal |
| 2002/0028404 A1 | 3/2002 | Nakamura |
| 2002/0029071 A1 | 3/2002 | Whitehurst |
| 2002/0032437 A1 | 3/2002 | Andrews et al. |
| 2002/0039702 A1 | 4/2002 | Hotta |
| 2002/0045891 A1 | 4/2002 | Clement et al. |
| 2002/0048722 A1 | 4/2002 | Aoshima |
| 2002/0049432 A1 | 4/2002 | Mukai |
| 2002/0049483 A1 | 4/2002 | Knowlton |
| 2002/0058890 A1 | 5/2002 | Visuri et al. |
| 2002/0071287 A1 | 6/2002 | Haase |
| 2002/0071827 A1 | 6/2002 | Petersen et al. |
| 2002/0072676 A1 | 6/2002 | Afanassieva |
| 2002/0081555 A1 | 6/2002 | Wiesel |
| 2002/0090725 A1 | 7/2002 | Simpson et al. |
| 2002/0091377 A1 | 7/2002 | Anderson et al. |
| 2002/0108193 A1 | 8/2002 | Gruber |
| 2002/0111546 A1 | 8/2002 | Cook et al. |
| 2002/0111610 A1 | 8/2002 | Nordquist |
| 2002/0120256 A1 | 8/2002 | Furuno et al. |
| 2002/0123745 A1 | 9/2002 | Svaasand et al. |
| 2002/0125230 A1 | 9/2002 | Haight et al. |
| 2002/0127224 A1 | 9/2002 | Chen |
| 2002/0128635 A1 | 9/2002 | Altshuler et al. |
| 2002/0128695 A1 | 9/2002 | Harth et al. |
| 2002/0128696 A1 | 9/2002 | Pearl et al. |
| 2002/0151878 A1 | 10/2002 | Shimmick et al. |
| 2002/0151879 A1 | 10/2002 | Loeb |
| 2002/0160299 A1 | 10/2002 | Asawa et al. |
| 2002/0161357 A1 | 10/2002 | Anderson et al. |
| 2002/0161418 A1 | 10/2002 | Wilkens et al. |
| 2002/0167974 A1 | 11/2002 | Kennedy et al. |
| 2002/0173723 A1 | 11/2002 | Lewis et al. |
| 2002/0173777 A1 | 11/2002 | Sand |
| 2002/0173780 A1 | 11/2002 | Altshuler et al. |
| 2002/0173781 A1 | 11/2002 | Cense et al. |
| 2002/0173782 A1 | 11/2002 | Cense et al. |
| 2002/0182563 A1 | 12/2002 | Boutoussov et al. |
| 2002/0183808 A1 | 12/2002 | Biel |
| 2002/0198517 A1 | 12/2002 | Alfano et al. |
| 2003/0004499 A1 | 1/2003 | McDaniel |
| 2003/0004556 A1 | 1/2003 | McDaniel |
| 2003/0009158 A1 | 1/2003 | Perricone |
| 2003/0009205 A1 | 1/2003 | Biel |
| 2003/0018373 A1 | 1/2003 | Eckhardt et al. |
| 2003/0023235 A1 | 1/2003 | Cense et al. |
| 2003/0023283 A1 | 1/2003 | McDaniel |
| 2003/0023284 A1 | 1/2003 | Gartstein et al. |
| 2003/0028186 A1 | 2/2003 | Kreindel |
| 2003/0028227 A1 | 2/2003 | Neuberger et al. |
| 2003/0032900 A1 | 2/2003 | Ella |
| 2003/0032950 A1 | 2/2003 | Altshuler et al. |
| 2003/0036680 A1 | 2/2003 | Black |
| 2003/0040739 A1 | 2/2003 | Koop |
| 2003/0055413 A1 | 3/2003 | Altshuler et al. |
| 2003/0055414 A1 | 3/2003 | Altshuler et al. |
| 2003/0057875 A1 | 3/2003 | Inochkin et al. |
| 2003/0059738 A1 | 3/2003 | Neuberger |
| 2003/0065314 A1 | 4/2003 | Altshuler et al. |
| 2003/0073989 A1 | 4/2003 | Hoey et al. |
| 2003/0083649 A1 | 5/2003 | Margaron et al. |
| 2003/0084534 A1 | 5/2003 | Kaizuka |
| 2003/0092982 A1 | 5/2003 | Eppstein |
| 2003/0097122 A1 | 5/2003 | Ganz et al. |
| 2003/0100936 A1 | 5/2003 | Altshuler et al. |
| 2003/0104340 A1 | 6/2003 | Clemans |
| 2003/0109787 A1 | 6/2003 | Black |
| 2003/0109860 A1 | 6/2003 | Black |
| 2003/0113684 A1 | 6/2003 | Scott |
| 2003/0129154 A1 | 7/2003 | McDaniel |
| 2003/0130709 A1 | 7/2003 | D.C et al. |
| 2003/0152528 A1 | 8/2003 | Singh et al. |
| 2003/0158550 A1 | 8/2003 | Ganz et al. |
| 2003/0163884 A1 | 9/2003 | Weihrauch |
| 2003/0167080 A1 | 9/2003 | Hart et al. |
| 2003/0169433 A1 | 9/2003 | Koele et al. |
| 2003/0181896 A1 | 9/2003 | Zvuloni et al. |
| 2003/0187319 A1 | 10/2003 | Kaneko et al. |
| 2003/0187383 A1 | 10/2003 | Weber et al. |
| 2003/0187486 A1 | 10/2003 | Savage et al. |
| 2003/0195494 A1 | 10/2003 | Altshuler et al. |
| 2003/0199859 A1 | 10/2003 | Altshuler et al. |
| 2003/0216719 A1 | 11/2003 | Debenedictis et al. |
| 2003/0216795 A1 | 11/2003 | Harth et al. |
| 2003/0232303 A1 | 12/2003 | Black |
| 2003/0233138 A1 | 12/2003 | Spooner |
| 2004/0006332 A1 | 1/2004 | Black |
| 2004/0010298 A1 | 1/2004 | Altshuler et al. |
| 2004/0015156 A1 | 1/2004 | Vasily |
| 2004/0015158 A1 | 1/2004 | Chen et al. |
| 2004/0019120 A1 | 1/2004 | Vargas et al. |
| 2004/0019990 A1 | 2/2004 | Farrell et al. |

(56) References Cited

U.S. PATENT DOCUMENTS

| | | |
|---|---|---|
| 2004/0024388 A1 | 2/2004 | Altshuler |
| 2004/0024430 A1 | 2/2004 | Bader et al. |
| 2004/0030326 A1 | 2/2004 | Altshuler et al. |
| 2004/0034319 A1 | 2/2004 | Anderson et al. |
| 2004/0034341 A1 | 2/2004 | Altshuler et al. |
| 2004/0036975 A1 | 2/2004 | Slatkine |
| 2004/0054248 A1 | 3/2004 | Kimchy et al. |
| 2004/0073079 A1 | 4/2004 | Altshuler et al. |
| 2004/0082940 A1 | 4/2004 | Black et al. |
| 2004/0085026 A1 | 5/2004 | Inochkin et al. |
| 2004/0092506 A1 | 5/2004 | Thompson et al. |
| 2004/0093042 A1 | 5/2004 | Altshuler et al. |
| 2004/0093043 A1 | 5/2004 | Edel et al. |
| 2004/0098070 A1 | 5/2004 | Mohr et al. |
| 2004/0105611 A1 | 6/2004 | Bischel et al. |
| 2004/0111031 A1 | 6/2004 | Alfano et al. |
| 2004/0111086 A1 | 6/2004 | Trembly |
| 2004/0111132 A1 | 6/2004 | Shenderova et al. |
| 2004/0116984 A1 | 6/2004 | Spooner et al. |
| 2004/0122311 A1 | 6/2004 | Cosman |
| 2004/0133251 A1 | 7/2004 | Altshuler et al. |
| 2004/0143181 A1 | 7/2004 | Damasco et al. |
| 2004/0143247 A1 | 7/2004 | Anderson et al. |
| 2004/0143920 A1 | 7/2004 | Nanda |
| 2004/0147984 A1 | 7/2004 | Altshuler et al. |
| 2004/0156626 A1 | 8/2004 | Thoms |
| 2004/0161213 A1 | 8/2004 | Lee |
| 2004/0162490 A1 | 8/2004 | Soltz et al. |
| 2004/0162549 A1 | 8/2004 | Altshuler |
| 2004/0162596 A1 | 8/2004 | Altshuler et al. |
| 2004/0167502 A1 | 8/2004 | Weckwerth et al. |
| 2004/0176754 A1 | 9/2004 | Island et al. |
| 2004/0176764 A1 | 9/2004 | Dant |
| 2004/0181211 A1 | 9/2004 | Graham et al. |
| 2004/0186465 A1 | 9/2004 | Francischelli et al. |
| 2004/0191729 A1 | 9/2004 | Altshuler et al. |
| 2004/0193234 A1 | 9/2004 | Butler |
| 2004/0193235 A1 | 9/2004 | Altshuler et al. |
| 2004/0193236 A1 | 9/2004 | Altshuler et al. |
| 2004/0199079 A1 | 10/2004 | Chuck et al. |
| 2004/0199151 A1 | 10/2004 | Neuberger |
| 2004/0199227 A1 | 10/2004 | Altshuler et al. |
| 2004/0204745 A1 | 10/2004 | Altshuler et al. |
| 2004/0208918 A1 | 10/2004 | Koch et al. |
| 2004/0210275 A1 | 10/2004 | Town et al. |
| 2004/0210276 A1 | 10/2004 | Altshuler et al. |
| 2004/0214132 A1 | 10/2004 | Altshuler |
| 2004/0225339 A1 | 11/2004 | Yaroslavsky et al. |
| 2004/0230258 A1 | 11/2004 | Altshuler et al. |
| 2004/0230260 A1 | 11/2004 | MacFarland et al. |
| 2004/0234460 A1 | 11/2004 | Tarver et al. |
| 2004/0249261 A1 | 12/2004 | Torchia et al. |
| 2004/0254567 A1 | 12/2004 | Holz et al. |
| 2004/0260210 A1 | 12/2004 | Ella et al. |
| 2005/0015077 A1 | 1/2005 | Kuklin et al. |
| 2005/0038418 A1 | 2/2005 | Altshuler et al. |
| 2005/0049467 A1 | 3/2005 | Stamatas et al. |
| 2005/0049582 A1 | 3/2005 | DeBenedictis et al. |
| 2005/0049658 A1 | 3/2005 | Connors et al. |
| 2005/0063931 A1 | 3/2005 | Paus et al. |
| 2005/0065502 A1 | 3/2005 | Stoltz |
| 2005/0065531 A1 | 3/2005 | Cohen |
| 2005/0074038 A1 | 4/2005 | Khaydarov |
| 2005/0080404 A1 | 4/2005 | Jones et al. |
| 2005/0085875 A1 | 4/2005 | Van Zuylen |
| 2005/0102213 A1 | 5/2005 | Savasoglu et al. |
| 2005/0107849 A1 | 5/2005 | Altshuler et al. |
| 2005/0113815 A1 | 5/2005 | Ritchie et al. |
| 2005/0113890 A1 | 5/2005 | Ritchie et al. |
| 2005/0116673 A1 | 6/2005 | Carl et al. |
| 2005/0131400 A1 | 6/2005 | Hennings et al. |
| 2005/0143719 A1 | 6/2005 | Sink |
| 2005/0143723 A1 | 6/2005 | Zvuloni et al. |
| 2005/0154380 A1 | 7/2005 | DeBenedictis et al. |
| 2005/0165315 A1 | 7/2005 | Zuluaga et al. |
| 2005/0165393 A1 | 7/2005 | Eppstein |
| 2005/0168158 A1 | 8/2005 | Inochkin et al. |
| 2005/0170313 A1 | 8/2005 | Pitz et al. |
| 2005/0171517 A1 | 8/2005 | Altshuler et al. |
| 2005/0171581 A1 | 8/2005 | Connors et al. |
| 2005/0177026 A1 | 8/2005 | Hoeg et al. |
| 2005/0177139 A1 | 8/2005 | Yamazaki et al. |
| 2005/0177142 A1 | 8/2005 | Jay |
| 2005/0182389 A1 | 8/2005 | LaPorte et al. |
| 2005/0197681 A1 | 9/2005 | Barolet et al. |
| 2005/0203496 A1 | 9/2005 | Ritchie et al. |
| 2005/0203497 A1 | 9/2005 | Speeg et al. |
| 2005/0215988 A1 | 9/2005 | Altshuler et al. |
| 2005/0220726 A1 | 10/2005 | Pauly et al. |
| 2005/0222556 A1 | 10/2005 | Ariura et al. |
| 2005/0245917 A1 | 11/2005 | Strassl et al. |
| 2005/0251116 A1 | 11/2005 | Steinke et al. |
| 2005/0251117 A1 | 11/2005 | Anderson et al. |
| 2005/0251118 A1 | 11/2005 | Anderson et al. |
| 2005/0251120 A1 | 11/2005 | Anderson et al. |
| 2005/0257612 A1 | 11/2005 | Hiemer et al. |
| 2005/0281530 A1 | 12/2005 | Rizoiu et al. |
| 2006/0004306 A1 | 1/2006 | Altshuler et al. |
| 2006/0004347 A1 | 1/2006 | Altshuler et al. |
| 2006/0007965 A1 | 1/2006 | Tankovich et al. |
| 2006/0009750 A1 | 1/2006 | Altshuler et al. |
| 2006/0013533 A1 | 1/2006 | Slatkine |
| 2006/0020309 A1 | 1/2006 | Altshuler et al. |
| 2006/0047281 A1 | 3/2006 | Kreindel |
| 2006/0052661 A1 | 3/2006 | Gannot et al. |
| 2006/0056589 A1 | 3/2006 | Engelward |
| 2006/0058712 A1 | 3/2006 | Altshuler et al. |
| 2006/0062448 A1 | 3/2006 | Hirsch et al. |
| 2006/0079947 A1 | 4/2006 | Tankovich et al. |
| 2006/0089687 A1 | 4/2006 | Spooner et al. |
| 2006/0094988 A1 | 5/2006 | Fosaya et al. |
| 2006/0095101 A1 | 5/2006 | Dees et al. |
| 2006/0100677 A1 | 5/2006 | Blumenkranz et al. |
| 2006/0116671 A1 | 6/2006 | Slayton et al. |
| 2006/0118127 A1 | 6/2006 | Chinn |
| 2006/0122584 A1 | 6/2006 | Bommannan et al. |
| 2006/0122668 A1 | 6/2006 | Anderson et al. |
| 2006/0128771 A1 | 6/2006 | Mirkov et al. |
| 2006/0149343 A1 | 7/2006 | Altshuler et al. |
| 2006/0155266 A1 | 7/2006 | Manstein et al. |
| 2006/0161143 A1 | 7/2006 | Altshuler et al. |
| 2006/0173480 A1 | 8/2006 | Zhang |
| 2006/0194164 A1 | 8/2006 | Altshuler et al. |
| 2006/0206103 A1 | 9/2006 | Altshuler et al. |
| 2006/0217689 A1 | 9/2006 | Dick et al. |
| 2006/0224148 A1 | 10/2006 | Cho et al. |
| 2006/0247609 A1 | 11/2006 | Mirkov et al. |
| 2006/0253176 A1 | 11/2006 | Caruso et al. |
| 2006/0259102 A1 | 11/2006 | Slatkine |
| 2006/0265032 A1 | 11/2006 | Hennings et al. |
| 2006/0271028 A1 | 11/2006 | Altshuler et al. |
| 2006/0282067 A1 | 12/2006 | Koop et al. |
| 2006/0287646 A1 | 12/2006 | Altshuler et al. |
| 2006/0293727 A1 | 12/2006 | Spooner et al. |
| 2006/0293728 A1 | 12/2006 | Roersma et al. |
| 2007/0027440 A1 | 2/2007 | Altshuler et al. |
| 2007/0038206 A1 | 2/2007 | Altshuler et al. |
| 2007/0038271 A1 | 2/2007 | Cole et al. |
| 2007/0049910 A1 | 3/2007 | Altshuler et al. |
| 2007/0060819 A1 | 3/2007 | Altshuler et al. |
| 2007/0060989 A1 | 3/2007 | Deem et al. |
| 2007/0067006 A1 | 3/2007 | Altshuler et al. |
| 2007/0073308 A1 | 3/2007 | Anderson et al. |
| 2007/0078501 A1 | 4/2007 | Altshuler et al. |
| 2007/0088206 A1 | 4/2007 | Peyman et al. |
| 2007/0093797 A1 | 4/2007 | Chan et al. |
| 2007/0105212 A1 | 5/2007 | Oldham et al. |
| 2007/0121069 A1 | 5/2007 | Andersen et al. |
| 2007/0123851 A1 | 5/2007 | Alejandro et al. |
| 2007/0142881 A1 | 6/2007 | Hennings |
| 2007/0159592 A1 | 7/2007 | Rylander et al. |
| 2007/0173749 A1 | 7/2007 | Williams et al. |
| 2007/0179378 A1 | 8/2007 | Boese et al. |
| 2007/0179470 A1 | 8/2007 | Toombs |

(56) References Cited

U.S. PATENT DOCUMENTS

| | | |
|---|---|---|
| 2007/0185552 A1 | 8/2007 | Masotti et al. |
| 2007/0191827 A1 | 8/2007 | Lischinsky et al. |
| 2007/0194717 A1 | 8/2007 | Belikov |
| 2007/0198004 A1 | 8/2007 | Altshuler et al. |
| 2007/0208252 A1 | 9/2007 | Makower |
| 2007/0213696 A1 | 9/2007 | Altshuler et al. |
| 2007/0213698 A1 | 9/2007 | Altshuler et al. |
| 2007/0213792 A1 | 9/2007 | Yaroslavsky et al. |
| 2007/0213851 A1 | 9/2007 | Bellas et al. |
| 2007/0219602 A1 | 9/2007 | Ostrovsky et al. |
| 2007/0219604 A1 | 9/2007 | Yaroslavsky et al. |
| 2007/0219605 A1 | 9/2007 | Yaroslavsky et al. |
| 2007/0239142 A1 | 10/2007 | Altshuler et al. |
| 2007/0239143 A1 | 10/2007 | Altshuler et al. |
| 2007/0244527 A1 | 10/2007 | Hatayama et al. |
| 2007/0255355 A1 | 11/2007 | Altshuler et al. |
| 2007/0260230 A1 | 11/2007 | Youngquist et al. |
| 2007/0264625 A1 | 11/2007 | DeBenedictis et al. |
| 2007/0280305 A1 | 12/2007 | Zucker |
| 2007/0288071 A1 | 12/2007 | Rogers |
| 2008/0003536 A1 | 1/2008 | Altshuler et al. |
| 2008/0004608 A1 | 1/2008 | Dacquay et al. |
| 2008/0004611 A1 | 1/2008 | Houbolt et al. |
| 2008/0009842 A1 | 1/2008 | Manstein et al. |
| 2008/0031288 A1* | 2/2008 | Sierra ............... H01S 3/00 372/12 |
| 2008/0033516 A1 | 2/2008 | Altshuler et al. |
| 2008/0058782 A1 | 3/2008 | Frangineas et al. |
| 2008/0058783 A1 | 3/2008 | Altshuler et al. |
| 2008/0103565 A1 | 5/2008 | Altshuler et al. |
| 2008/0132886 A1 | 6/2008 | Cohen et al. |
| 2008/0139901 A1 | 6/2008 | Altshuler et al. |
| 2008/0140164 A1 | 6/2008 | Oberreiter et al. |
| 2008/0147054 A1 | 6/2008 | Altshuler et al. |
| 2008/0154157 A1 | 6/2008 | Altshuler et al. |
| 2008/0154247 A1 | 6/2008 | Dallarosa et al. |
| 2008/0172047 A1 | 7/2008 | Altshuler et al. |
| 2008/0183162 A1 | 7/2008 | Altshuler et al. |
| 2008/0183250 A1 | 7/2008 | Tanojo et al. |
| 2008/0186591 A1 | 8/2008 | Altshuler et al. |
| 2008/0194969 A1 | 8/2008 | Werahera et al. |
| 2008/0195183 A1 | 8/2008 | Botchkareva et al. |
| 2008/0208105 A1 | 8/2008 | Zelickson et al. |
| 2008/0214988 A1 | 9/2008 | Altshuler et al. |
| 2008/0215038 A1 | 9/2008 | Bakker et al. |
| 2008/0248554 A1 | 10/2008 | Merchant et al. |
| 2008/0262577 A1 | 10/2008 | Altshuler et al. |
| 2008/0294150 A1 | 11/2008 | Altshuler et al. |
| 2008/0294152 A1 | 11/2008 | Altshuler et al. |
| 2008/0294153 A1 | 11/2008 | Altshuler et al. |
| 2008/0306471 A1 | 12/2008 | Altshuler et al. |
| 2008/0319430 A1 | 12/2008 | Zenzie et al. |
| 2009/0018531 A1 | 1/2009 | Welches et al. |
| 2009/0018624 A1 | 1/2009 | Levinson et al. |
| 2009/0024023 A1 | 1/2009 | Welches et al. |
| 2009/0024192 A1 | 1/2009 | Mulholland |
| 2009/0024193 A1 | 1/2009 | Altshuler et al. |
| 2009/0043294 A1 | 2/2009 | Island et al. |
| 2009/0048557 A1 | 2/2009 | Yeshurun et al. |
| 2009/0069741 A1 | 3/2009 | Altshuler et al. |
| 2009/0132011 A1 | 5/2009 | Altshuler et al. |
| 2009/0137995 A1 | 5/2009 | Altshuler et al. |
| 2009/0149843 A1 | 6/2009 | Smits et al. |
| 2009/0149844 A1 | 6/2009 | Altshuler et al. |
| 2009/0222068 A1 | 9/2009 | Oberreiter et al. |
| 2009/0248004 A1 | 10/2009 | Altshuler et al. |
| 2009/0254076 A1 | 10/2009 | Altshuler et al. |
| 2009/0287195 A1 | 11/2009 | Altshuler et al. |
| 2009/0292277 A1 | 11/2009 | Sierra et al. |
| 2009/0312749 A1 | 12/2009 | Pini et al. |
| 2010/0010507 A1 | 1/2010 | Kinoshita et al. |
| 2010/0015576 A1 | 1/2010 | Altshuler et al. |
| 2010/0021867 A1 | 1/2010 | Altshuler et al. |
| 2010/0036295 A1 | 2/2010 | Altshuler et al. |
| 2010/0049180 A1 | 2/2010 | Wells et al. |
| 2010/0109041 A1 | 5/2010 | Yin et al. |
| 2010/0123399 A1 | 5/2010 | Bollmann et al. |
| 2010/0145321 A1 | 6/2010 | Altshuler et al. |
| 2010/0195680 A1 | 8/2010 | Sierra et al. |
| 2010/0198134 A1 | 8/2010 | Eckhouse et al. |
| 2010/0204686 A1 | 8/2010 | Yaroslavksy et al. |
| 2010/0217248 A1 | 8/2010 | Mirkov et al. |
| 2010/0278756 A1 | 11/2010 | Chung et al. |
| 2010/0286673 A1 | 11/2010 | Altshuler et al. |
| 2010/0298744 A1 | 11/2010 | Altshuler et al. |
| 2011/0046523 A1 | 2/2011 | Altshuler et al. |
| 2011/0087155 A1 | 4/2011 | Uhland et al. |
| 2011/0118722 A1 | 5/2011 | Lischinsky et al. |
| 2011/0137230 A1 | 6/2011 | Altshuler et al. |
| 2011/0152847 A1 | 6/2011 | Mirkov et al. |
| 2011/0172651 A1 | 7/2011 | Altshuler et al. |
| 2011/0184334 A1 | 7/2011 | Altshuler et al. |
| 2011/0207075 A1 | 8/2011 | Altshuler et al. |
| 2011/0257584 A1 | 10/2011 | Altshuler et al. |
| 2011/0267830 A1 | 11/2011 | Altshuler et al. |
| 2011/0313408 A1 | 12/2011 | Tankovich et al. |
| 2012/0022510 A1 | 1/2012 | Welches et al. |
| 2012/0023129 A1 | 1/2012 | Vedula et al. |
| 2012/0083862 A1 | 4/2012 | Altshuler et al. |
| 2012/0099816 A1 | 4/2012 | Wilson |
| 2012/0116271 A1 | 5/2012 | Caruso et al. |
| 2012/0123399 A1 | 5/2012 | Belikov et al. |
| 2012/0165725 A1 | 6/2012 | Chomas et al. |
| 2012/0277659 A1 | 11/2012 | Yaroslavsky et al. |
| 2012/0301842 A1 | 11/2012 | Altshuler et al. |
| 2014/0371730 A1 | 12/2014 | Sierra et al. |

FOREIGN PATENT DOCUMENTS

| | | |
|---|---|---|
| CN | 2053926 U | 3/1990 |
| CN | 1073607 A | 6/1993 |
| CN | 1182572 A | 5/1998 |
| CN | 1351483 A | 5/2002 |
| CN | 1535126 A | 10/2004 |
| CN | 101055401 A | 10/2007 |
| DE | 2826383 A1 | 12/1979 |
| DE | 3304230 A1 | 8/1984 |
| DE | 3719561 A1 | 1/1988 |
| DE | 8807746 U1 | 9/1988 |
| DE | 3837248 A1 | 5/1990 |
| DE | 3841503 A1 | 6/1990 |
| DE | 9102407 U1 | 7/1991 |
| DE | 19803460 C1 | 8/1999 |
| DE | 19944401 A1 | 3/2001 |
| DE | 10140715 A1 | 3/2002 |
| DE | 10112289 A1 | 9/2002 |
| DE | 10120787 A1 | 1/2003 |
| EP | 0000593 A1 | 2/1979 |
| EP | 0142671 A1 | 5/1985 |
| EP | 0172490 A1 | 2/1986 |
| EP | 0297360 A1 | 1/1989 |
| EP | 0320080 A1 | 6/1989 |
| EP | 0324120 A1 | 7/1989 |
| EP | 0413025 A1 | 2/1991 |
| EP | 0458576 A2 | 11/1991 |
| EP | 0563953 A2 | 10/1993 |
| EP | 0565331 A2 | 10/1993 |
| EP | 0575274 A1 | 12/1993 |
| EP | 0593375 A1 | 4/1994 |
| EP | 0598984 A1 | 6/1994 |
| EP | 0709941 A1 | 5/1996 |
| EP | 0724894 A2 | 8/1996 |
| EP | 0726083 A2 | 8/1996 |
| EP | 0736308 A2 | 10/1996 |
| EP | 0743029 A2 | 11/1996 |
| EP | 0755698 A2 | 1/1997 |
| EP | 0763371 A2 | 3/1997 |
| EP | 0765673 A2 | 4/1997 |
| EP | 0765674 A2 | 4/1997 |
| EP | 0783904 A2 | 7/1997 |
| EP | 0884066 A2 | 12/1998 |
| EP | 0885629 A2 | 12/1998 |
| EP | 0920840 A2 | 6/1999 |
| EP | 0927544 A2 | 7/1999 |

(56) References Cited

FOREIGN PATENT DOCUMENTS

| | | |
|---|---|---|
| EP | 0949730 A2 | 10/1999 |
| EP | 1031414 A1 | 8/2000 |
| EP | 1038505 A2 | 9/2000 |
| EP | 1057454 A2 | 12/2000 |
| EP | 1057455 A2 | 12/2000 |
| EP | 1072402 A2 | 1/2001 |
| EP | 1075854 A2 | 2/2001 |
| EP | 1138269 A1 | 10/2001 |
| EP | 1138349 A2 | 10/2001 |
| EP | 1147785 A2 | 10/2001 |
| EP | 1219258 A1 | 7/2002 |
| EP | 1226787 A2 | 7/2002 |
| EP | 1238683 A1 | 9/2002 |
| EP | 1250893 A2 | 10/2002 |
| EP | 1457234 A2 | 9/2004 |
| EP | 1495735 A1 | 1/2005 |
| EP | 1512373 A1 | 3/2005 |
| EP | 1535582 A1 | 6/2005 |
| EP | 1627662 A1 | 2/2006 |
| EP | 1650615 A1 | 4/2006 |
| EP | 1797836 A1 | 6/2007 |
| EP | 1839705 A1 | 10/2007 |
| EP | 1854505 A2 | 11/2007 |
| FR | 1251424 A | 1/1961 |
| FR | 2199453 A1 | 4/1974 |
| FR | 2591902 A1 | 6/1987 |
| GB | 1251424 A | 10/1971 |
| GB | 1274017 A | 5/1972 |
| GB | 1546625 A | 5/1979 |
| GB | 2044908 A | 10/1980 |
| GB | 2059053 A | 4/1981 |
| GB | 2059054 A | 4/1981 |
| GB | 2123287 A | 2/1984 |
| GB | 2212010 A | 7/1989 |
| GB | 2239675 A | 7/1991 |
| GB | 2270159 A | 3/1994 |
| GB | 2356570 A | 5/2001 |
| GB | 2360461 A | 9/2001 |
| GB | 2360946 A | 10/2001 |
| GB | 2364376 A | 1/2002 |
| GB | 2368020 A | 4/2002 |
| GB | 2390021 A | 12/2003 |
| GB | 2397528 A | 7/2004 |
| JP | S54129791 A | 10/1979 |
| JP | S5552766 A | 4/1980 |
| JP | S5577187 A | 6/1980 |
| JP | S574007 A | 1/1982 |
| JP | S62165985 A | 7/1987 |
| JP | S6323648 A | 1/1988 |
| JP | S63249577 A | 10/1988 |
| JP | S6427554 A | 1/1989 |
| JP | S6481222 A | 3/1989 |
| JP | H0199574 A | 4/1989 |
| JP | H01181877 A | 7/1989 |
| JP | H02199 A | 1/1990 |
| JP | H022199 A | 1/1990 |
| JP | H0213014 A | 1/1990 |
| JP | H0285694 A | 3/1990 |
| JP | H02174804 A | 7/1990 |
| JP | H02285694 A | 11/1990 |
| JP | H0316956 A | 1/1991 |
| JP | H0319385 A | 1/1991 |
| JP | H0366387 A | 3/1991 |
| JP | H03183184 A | 8/1991 |
| JP | H03281390 A | 12/1991 |
| JP | H0622871 A | 2/1994 |
| JP | H06154239 A | 6/1994 |
| JP | H079179 A | 1/1995 |
| JP | H0763957 A | 3/1995 |
| JP | H07328025 A | 12/1995 |
| JP | H0815539 A | 1/1996 |
| JP | H0854538 A | 2/1996 |
| JP | H0984803 A | 3/1997 |
| JP | H09141869 A | 6/1997 |
| JP | H9220292 A | 8/1997 |
| JP | H1014661 A | 1/1998 |
| JP | H1147146 A | 2/1999 |
| JP | H11232229 A | 8/1999 |
| JP | 2000037400 A | 2/2000 |
| JP | 2000153003 A | 6/2000 |
| JP | 2000300684 A | 10/2000 |
| JP | 2001000560 A | 1/2001 |
| JP | 2001029124 A | 2/2001 |
| JP | 2001145520 A | 5/2001 |
| JP | 2001196665 A | 7/2001 |
| JP | 2001343560 A | 12/2001 |
| JP | 2002272861 A | 9/2002 |
| JP | 2003052843 A | 2/2003 |
| JP | 2005017796 A | 1/2005 |
| JP | 2005027702 A | 2/2005 |
| JP | 2006192073 A | 7/2006 |
| RU | 2082337 C1 | 6/1997 |
| RU | 2089126 C1 | 9/1997 |
| RU | 2089127 C1 | 9/1997 |
| RU | 2096051 C1 | 11/1997 |
| RU | 2122848 C1 | 12/1998 |
| WO | 9602783 A1 | 5/1986 |
| WO | 9804592 A1 | 6/1988 |
| WO | 9000420 A1 | 1/1990 |
| WO | 9006727 A1 | 6/1990 |
| WO | 9012548 A1 | 11/1990 |
| WO | 9101053 A1 | 1/1991 |
| WO | 9102562 A1 | 3/1991 |
| WO | 9112050 A1 | 8/1991 |
| WO | 9113652 A1 | 9/1991 |
| WO | 9113653 A1 | 9/1991 |
| WO | 9118646 A1 | 12/1991 |
| WO | 9203977 A2 | 3/1992 |
| WO | 9206739 A1 | 4/1992 |
| WO | 9216338 A1 | 10/1992 |
| WO | 9219165 A1 | 11/1992 |
| WO | 9305920 A1 | 4/1993 |
| WO | 9321843 A1 | 11/1993 |
| WO | 9503089 A1 | 2/1995 |
| WO | 9504393 A2 | 2/1995 |
| WO | 9510243 A1 | 4/1995 |
| WO | 9514251 A1 | 5/1995 |
| WO | 9515725 A1 | 6/1995 |
| WO | 9532441 A1 | 11/1995 |
| WO | 9533518 A1 | 12/1995 |
| WO | 9609853 A1 | 4/1996 |
| WO | 9618347 A1 | 6/1996 |
| WO | 9622741 A1 | 8/1996 |
| WO | 9622813 A1 | 8/1996 |
| WO | 9623447 A1 | 8/1996 |
| WO | 9624182 A1 | 8/1996 |
| WO | 9624406 A1 | 8/1996 |
| WO | 9625979 A1 | 8/1996 |
| WO | 9628212 A1 | 9/1996 |
| WO | 1996034316 A1 | 10/1996 |
| WO | 9636396 A2 | 11/1996 |
| WO | 9639734 A1 | 12/1996 |
| WO | 9641579 A1 | 12/1996 |
| WO | 1997000777 A2 | 1/1997 |
| WO | 9713458 A1 | 4/1997 |
| WO | 9713552 A1 | 4/1997 |
| WO | 9722384 A1 | 6/1997 |
| WO | 9728752 A1 | 8/1997 |
| WO | 9737602 A2 | 10/1997 |
| WO | 9737723 A1 | 10/1997 |
| WO | 9804317 A1 | 2/1998 |
| WO | 9805286 A1 | 2/1998 |
| WO | 9805380 A1 | 2/1998 |
| WO | 9806456 A1 | 2/1998 |
| WO | 9807379 A1 | 2/1998 |
| WO | 9820937 A2 | 5/1998 |
| WO | 9824507 A2 | 6/1998 |
| WO | 9829134 A2 | 7/1998 |
| WO | 9841158 A1 | 9/1998 |
| WO | 9851235 A1 | 11/1998 |
| WO | 9852481 A1 | 11/1998 |
| WO | 9858595 A1 | 12/1998 |
| WO | 9910046 A1 | 3/1999 |
| WO | 9917666 A1 | 4/1999 |

(56) References Cited

FOREIGN PATENT DOCUMENTS

| | | |
|---|---|---|
| WO | 9917667 A1 | 4/1999 |
| WO | 9917668 A1 | 4/1999 |
| WO | 9927997 A1 | 6/1999 |
| WO | 9929243 A1 | 6/1999 |
| WO | 9934867 A1 | 7/1999 |
| WO | 9938569 A2 | 8/1999 |
| WO | 9939410 A1 | 8/1999 |
| WO | 9943387 A1 | 9/1999 |
| WO | 9944638 A1 | 9/1999 |
| WO | 9946005 A1 | 9/1999 |
| WO | 9949937 A1 | 10/1999 |
| WO | 9958195 A1 | 11/1999 |
| WO | 9962472 A1 | 12/1999 |
| WO | 9966988 A1 | 12/1999 |
| WO | 0002491 A1 | 1/2000 |
| WO | 0003257 A1 | 1/2000 |
| WO | 0007514 A1 | 2/2000 |
| WO | 0030714 A1 | 6/2000 |
| WO | 0032272 A1 | 6/2000 |
| WO | 0040266 A2 | 7/2000 |
| WO | 0041278 A1 | 7/2000 |
| WO | 0043070 A1 | 7/2000 |
| WO | 0044294 A1 | 8/2000 |
| WO | 0053113 A1 | 9/2000 |
| WO | 0054649 A2 | 9/2000 |
| WO | 0054685 A2 | 9/2000 |
| WO | 0062700 A1 | 10/2000 |
| WO | 0064537 A1 | 11/2000 |
| WO | 0066226 A1 | 11/2000 |
| WO | 0071045 A1 | 11/2000 |
| WO | 0074583 A1 | 12/2000 |
| WO | 0074781 A1 | 12/2000 |
| WO | 0078242 A1 | 12/2000 |
| WO | 0103257 A1 | 1/2001 |
| WO | 0114012 A1 | 3/2001 |
| WO | 0126573 A1 | 4/2001 |
| WO | 0134048 A1 | 5/2001 |
| WO | 2001042671 A1 | 6/2001 |
| WO | 0150963 A1 | 7/2001 |
| WO | 0154606 A1 | 8/2001 |
| WO | 0154770 A1 | 8/2001 |
| WO | 0178830 A2 | 10/2001 |
| WO | 0209813 A1 | 2/2002 |
| WO | 0226147 A1 | 4/2002 |
| WO | 02053050 A1 | 7/2002 |
| WO | 02069825 A2 | 9/2002 |
| WO | 02078559 A1 | 10/2002 |
| WO | 02094116 A1 | 11/2002 |
| WO | 03005883 A2 | 1/2003 |
| WO | 03049633 A1 | 6/2003 |
| WO | 03103529 A1 | 12/2003 |
| WO | 2004000150 A1 | 12/2003 |
| WO | 2004011848 A2 | 2/2004 |
| WO | 2004033040 A1 | 4/2004 |
| WO | 2004037068 A2 | 5/2004 |
| WO | 2004037287 A2 | 5/2004 |
| WO | 2004073537 A2 | 9/2004 |
| WO | 2004080279 A2 | 9/2004 |
| WO | 2004084752 A2 | 10/2004 |
| WO | 2004086947 A2 | 10/2004 |
| WO | 2005007003 A1 | 1/2005 |
| WO | 2005009266 A1 | 2/2005 |
| WO | 2005030317 A2 | 4/2005 |
| WO | 2005046793 A2 | 5/2005 |
| WO | 2005065288 A2 | 7/2005 |
| WO | 2005092438 A1 | 10/2005 |
| WO | 2005096981 A2 | 10/2005 |
| WO | 2005099369 A2 | 10/2005 |
| WO | 2005112815 A1 | 12/2005 |
| WO | 2006006123 A1 | 1/2006 |
| WO | 2006036968 A2 | 4/2006 |
| WO | 2006066226 A1 | 6/2006 |
| WO | 2006089227 A2 | 8/2006 |
| WO | 2006101735 A1 | 9/2006 |
| WO | 2006116141 A1 | 11/2006 |
| WO | 2007035444 A2 | 3/2007 |
| WO | 2007122611 A2 | 11/2007 |
| WO | 2008007218 A2 | 1/2008 |
| WO | 2008070747 A2 | 6/2008 |
| WO | 2008153999 A1 | 12/2008 |
| WO | 2010102255 A1 | 9/2010 |
| WO | 2012023129 A1 | 2/2012 |

OTHER PUBLICATIONS

Goldman, M. P., "Leg Veins and Lasers," American Society for Laser Medicine and Surgery Abstracts, Fourteen Annual Meeting, Toronto, Ontario, Canada, p. 48 (Apr. 8-10, 1994).

Gottlieb, I., "Power Supplies, Switching Regulators, Inverters & Converters," 1976.

Greenwald et al. "Comparative Histological Studies of the Tunable Dye (at 577 nm) Laser and Argon Laser: The Specific Vascular Effects of the Dye Laser," The Journal of Investigative Dermatology, 77:305-310 (1981).

Grossman, et al., "780 nm Low Power Diode Laser Irradiation Stimulates Proliferation of Keratinocyte Cultures nvolvement of Reactive Oxygen Species," Lasers in Surgery and Medicine vol. 29, pp. 212-218, 1998.

Grossman, M.C et al., "Damage to hair follicles by normal-mode ruby laser pulses," Journal of he American Academy of Dermatology, vol. 35, No. 6, pp. 889-894, Dec. 1996.

Grossman, M.C. et al., "Laser Targeted at Hair Follicles," Lasers Med Surg., Suppl. 13:221 (2001).

Haedersal, et el., "Fractional Nonablative 1540 nm Laser Resurfacing for Thermal Burn Scars: a Randomized Controlled Trial", Lasers in Surgery and Medicine, 41:189-195,2009, 7 pages.

Hicks et al., "After Low Fluence Argon Laser and Flouride Treatment," Compendium, vol. 18, No. 6, Jun. 1997.

Hicks et al., "Enamel Carries Initiation and Progression Following Low Fluence (energy) and Argon Laser and Fluoride Treatment," The Journal of Clinical Pediatric Dentistry, vol. 20, No. 1 pp. 9-13, 1995.

Hsu et al., "Combined Effects of Laser Irradiation/Solution Flouride Ion on Enamel Demineralization," Journal of Clinical Laser Medicine and Surgery, vol. 16, No. 2 pp. 93-105, 1998.

Hulsbergen Henning et al. "Clinical and Histological Evaluation of Portwine Stain Treatment with a Microsecond-Pulsed Dye-Laser at 577 NM," Lasers in Surgery and Medicine, 4:375-380 (1984).

Hulsbergen Henning et al., "Port Wine Stain Coagulation Experiments with a 540-nm Continuous Wave Dye-Laser," Lasers in Surgery and Medicine, 2:205-210 (1983).

Ivanov, A.P. et al., "Radiation Propagation in Tissues and Liquids with Close Particle Packing," Zhurnal Prikladnoi Spektroskopii, vol. 47, No. 4, pp. 662-668 (Oct. 1987).

Johnsson et al., "No photoinactivation of Propionibacterium acnes with soft laser treatment," Dermatologica, 175(1):50, 1987.

Kalivradzhiyan et al., "The Usage of Low Intensity Laser Radiation for the Treatment of the Inflammatory processes of the Oral Cavity Mucosa after Applying Removable Plate Dentures," SPIE vol. 1984 pp. 225-230.

Kandel, Laurence B., M.D., et al., "Transurethral Laser Prostatectomy in the Canine Model," Lasers in Surgery and Medicine, 12:33-42 (1992).

Kantor et al., "Treatment of acne keloidalis nuchae with carbon dioxide laser," J. Am. Acad. Dermatol., 14:263-267, 1986.

Karu, "Cell Attachment to Extracellular Matrics is Modulated by Pulsed Radiation at 820 nm and Chemicals that Modify the Activity of Enzymes in the Plasma Membrane," Laser in Surgery and Medicine, vol. 29, pp. 274-281, 2001.

Karu, "Photobiological Fundamentals of Low-Power Laser Therapy," 8th Congress of International Society for Laser Surgery and Medicine, Mar. 30, 1987.

Kazmina et al., "Laser Prophlaxis and Treatment of Primary caries," SPIE vol. 1984, pp. 231-233.

Kilmer et al., "Pulse Dye Laser Treatment of Rhytids," American Society for Laser Medicine and Surgery Abstracts, p. 44 (Apr. 1997).

(56) References Cited

OTHER PUBLICATIONS

Klein E. et al., "Biological effects of laser radiation 1.,"Northeast Electroncis Research and Engineering Meeting, NEREM Record, IEEE catalogue No. F-60, pp. 108-109, 1965.
Korobov et al., "Dependence of the Quantum Yield of Intercombinational Conversion into the Triplet State of Rhodamine 6G on the pH of the Medium", Zhur. Prikl Spektrosk. 24(1) 28-31 (Jan. 1976).
Kozlov et al., "Laser in Diagnostics and Treatment of Microcirculation Disorders Under Parodontitis," SPIE vol. 1984, pp. 253-264.
Krames et al. (2007) "Status and Future of High-Power Light-Emitting Diodes for Solid State Lighting," J. Display Technol., 3(2):160-175.
Kuhns J.G. et al., "Biological effects of laser radiation II Effects of laser irradiation on the skin," NEREM Record, pp. 152-153, 1965.
Kuhns J.G. et al., "Laser injury in skin," Laboratory Investigation, vol. 17, No. 1, pp. 1-13, Jul. 1967.
Leger, J. et al., "Geometrical Transformation of Linear Diode-Laser Arrays for Longitudinal Pumping of Solid-State Lasers," IEEE Journal of Quantum Electronics, vol. 28, No. 4, Apr. 1992.
Lesnik et al., "Agents that cause enlargement of sebaceous glands in hairless mice," Arch. Dermatol., 284:100-105, 1992.
Levin, G. et al., "Designing with hyseretic current-mode control," EDN Magazine, pp. 1-8, Apr. 11, 1996.
Levin, G. et al., "Designing with hyseretic current-mode control," EDN Magazine, pp. 1-8, Apr. 28, 1994.
Lucchina et al., "Fluorescence photography in the evaluation of acne," J. Am. Acad. Dermatol. 35:58-63 (1996).
Maegawa, et al., "Effects of Near-Infrared Low-Level Laser Irradiation on Microcirculation," Lasers in Surgery and Medicine, vol. 27, pp. 427-437, 2000.
Mamedova et al., "Microbiological Estimate of Parodontis Laser Therapy Efficiency," SPIE vol. 1984, pp. 247-249.
Manstein, D. et al., "Selective Photothermolysis of Lipid-Rich Tissue," American Society for Laser medicine and Surgery Abstracts, No. 17, American Society for Laser Medicine and Surgery Twenty-First Annual Meeting, Apr. 20-22, 2001, p. 6.
Manstein, D., et al., "Fractional Photothermolysis: A New Concept for Cutaneous Remodeling Using Microscopic Patterns of Thermal Injury," Lasers in Surgery and Medicine, 34: 426-438 (2004).
Manuskiatti et al., "Laser hair removal affects sebaceous glands and sebum excretion: a pilot study" J. Am. Acad. Dermatol., 41:176-180, 1999.
Margolis, R.J. et al., "Visible action spectrum for melanin-specific selective photothermolysis," Lasers in Surgery and Medicine, vol. 9, pp. 389-397, 1989.
Marinelli et al., "Diode laser illuminated automotive lamp systems," SPIE Proceedings vol. 3285:170-177 (1998).
Marshak, I.S., et al., "Pulsed Light Sources," State Power Engineering Press, Moscow and Leningrad (1963).
Matsunaga et al., "Effect of pH on Dye-Laser Output Power", J. Appl. Phys. 48(2):842-844 (Feb. 1977).
Roth et al. "Transurethral Ultrasound-guided Laser-Induced Prostatectomy (TULIP) Procedure): A Canine Prostate Feasibility Study," The Journal of Urology, 146:1126-1135 (1991).
McDaniel, et al., "Hexascan: A New Robotized Scanning Laser Handpiece," Cutis, 45:300-305 (1990).
McNicholas, T. A., et al., "Interstitial Laser Coagulation of the Prostate: Experimental Studies," SPIE, 1421:30-35 4991). (From Proceedings of Lasers in Urol., Laparoscopy, and General Surgery, Jan. 21-23, (1991).
Moretti, Michael, "Holmium Boosts Orthopedic Laser Development," Medical Laser Buyers Guide, p. 93 (1992).
Moretti, Michael, "Lasers Improve Prostatectomy Treatment," Medical Laser Buyers Guide, p. 94-96 (1992).
Mostovnikov, V.A. et al., "Recovery of Lasing Properties of Dye Solutions after Their Photolysis," Sov. J. Quantum Electron, 6(9), Sep. 1976, pp. 1126-1128.
Nanni, C.A. et al., "Complications of Carbon Dioxide Laser Resurfacing," Washington Inst. of Dermatol. Surg. 24:315-320 (1998).

Nemeth, et al., "Copper vapor laser treatment of pigmented lesions," Lasers Surg. Med. Supp. 2:51 (1990).
Ohbayashi, "Stimulatory Effect of Laser Irradiation on Calcified Nodule Formation in Human Dental Pulp Fibroblasts," Abstract J-Endod Jan. 1999; 25(1): 30-3.
Ohshiro et al., "The Ruby and Argon Lasers in the Treatment of the Naevi," Annals Academy of Medicine, Apr. 1983, vol. 12, No. 2, pp. 388-395.
Oleinik, et al., "Automatized Securing Definition for Laser Therapy Indications in Case of Non-complicated Caries," SPIE, vol. 1984, pp. 238-244.
Orchardson, "Effect of Pulsed Nd:YAG Laser Radiation on Action Potential Conduction in Nerve Fibres Inside Teeth in vitro," Abstract J-Dent. Jul.-Aug. 1998; 26(5-6): 421-6.
Overholt BF et al. "Balloon photodynamic therapy of esophageal cancer: effect of increasing balloon size." PubMed; Lasers Surg Med. 1996, 18(3):248-52.
Ozawa et al., "Stimulatory Effects of Low-Power Laser Irradiation on Bone Formation in vitro," SPIE vol. 1984, pp. 281-288.
Panjehpour M et al. "Spectroscopic diagnosis of esophageal cancer: new classification model, improved measurement system." PubMed; Gastrointest Endosc. 1995, Jun.; 41 (6):577-81.
Parrish, J.A., "Selective thermal effects with pulsed irradiation from lasers: From organ to organelle," Journal of Investigative Dermatology, vol. 80, No. 6 Supplement, p. 75s-80s, 1983.
Petrischev et al. "Clinical and Experimental Low-Intense Laser Therapy in Dentistry," SPIE, vol. 1984, pp. 212-214.
Petrischev et al., "Report on Low Intensity Laser Radiation Usage in Dentistry," SPIE vol. 1984, pp. 202-211.
Polanyi, Thomas & Tobias, Irwin, Lasers-A Series of Advances, Edited by A.K. Levine, vol. 2, Marcel Dekker, Inc, N.Y., 1968, pp. 400, 402-403 & 422.
Polla, L. et al., "Melanosomes are a primary target of Q-switched ruby laser irradiation in guinea pig skin," Journal of Investigative Dermatology, vol. 89, No. 3, pp. 281-286, Sep. 1987.
Powell, "Laser Dental Decay Prevention: does it have a future?" SPIE vol. 3192, 1997.
Reed J.T. et al., "Treatment of Periorbital Wrinkles," Washington Inst, of Dermatol. Surg. 23:643-648 (1997).
Remillard et al., "Diode laser illuminated automotive brake lamp using a linear fanout diffractive optical element," Proc. of the Diffractive Optics and Micro-Optics Conference, OSA Technical Digest Series vol. 10, 192-194 (1998).
Remillard et al., "Diode Laser Illuminators for Night-Vision Applications," SPIE Proceedings vol. 4285:14-22 (2001).
Riggle et al., "Laser Effects on Normal and Tumor Tissue," Laser Applications in Medicine and Biology, vol. 1, M.L. Wolbarsht, editor, Plenum Press, publishers, Ch. 3, pp. 35-65 (1971).
Rohrer, "Evaluating the Safety and Efficacy Of A Novel Light Based Hair Removal System," Lasers. Surg. Med. Supp. 13:97 (2001).
Rosenfeld, H., et al., "Treatment of Cutaneous and Deep Vascular Lesions with the Nd:YAG Laser," Lasers in Surgery and Medicine, 6:20-23 (1986).
Rotteleur, et al., "Robotized scanning laser handpiece for the treatment of port wine stains and other angiodysplasias," Lasers Surg. Med., 8:283-287 (1998).
Rubach et al., "Histological and Clinical Evaluation of Facial Resurfacing Using a Carbon Dioxide Laser With the Computer Pattern Generator," Arch Otolaryngol Head Neck Surg., 123:929-934 (1997).
Rylander, C.G. et al., "Mechanical Tissue Optical Clearing Devices: Enhancement of Light Penetration in Ex Vivo Porcine Skin and Adipose Tissue," Lasers in Surgery and Medicine, vol. 40, pp. 688-694 (2008).
Sandford et al.,"Thermal Effects During Desensitisation of Teeth with Gallium-Aluminum-Arsenide Lasers," University of Queensland Dental School, Periodontology 15:25-30 (1994).
Schade, W. et al., "Temperature tuned distributed feedback dye laser with high repetition rate", Applied Optics, vol. 2 9, No. 27, Sep. 20, 1990, pp. 3950-3954.
Schappert et al., "Temperture Tuning of an Organic Dye Laser" Applied Physics Letters 13(4):124-126 (Aug. 15, 1968).

(56) References Cited

OTHER PUBLICATIONS

Schindl, "Does Low Intensity Laser Irradiation Really Cause Cell Damage?" Laser in Surgery and Medicine vol. 22, pp. 105, 2001.
Sheehan-Dare, et al., "Lasers in Dermatology," British Journal of Dermatology, 129:1-8 (1993).
Shimbashi, T. et al., "Ruby laser treatment of pigmented skin lesions," Aesth. Plast. Surg., vol. 19, pp. 225-229, 1995.
Shimizu et al., "Prospect of Relieving Pain Due to Tooth Movement During Orthodontic Treatment Utilizing a GA-AL As Diode Laser," SPIE vol. 1984, pp. 275-280.
Shumilovitch et al., "Influence of Low Intensity Laser Radiation Upon the Microflora of Carious Cavities and Root Canal," SPIE vol. 1984, pp. 215-220.
Shuster, "Acne: The Ashes of a Burnt Out Controversy," Acta Derm. Venereol. SuppL (Stockh), 120:43-46, 1985.
Sigurdsson et al., "Phototherapy of Acne Vulgaris with Visible Light," Dermatology, 194:256-260, 1997.
Sing, "Electroacupuncture and Laser Stimulation Treatment: Evaluation by Somatosensory Evoked Potential in Conscious Rabbits," Abstract AM-J-Chin-Med. 1997; 25(3-4): 263-71.
Sliney et al., "Safety with Lasers and Other Optical Sources: A Comprehensive Handbook," Plenum Press, pp. 477-480 (1980).
Sokolova et al., "Low-intense Laser Radiation in Complex Treatment of Inflammatory Diseases of Parodontium," SPIE vol. 1984, pp. 234-237.
Spears et al., "Fluorescence of Experimental Atheromatous Plaques with Hematoporphyrin Derivative," J. Clin. Invest, 71:395-399 (1983).
Spotswood, "Novel Use of Fractional Lasers for Scarring Improves Quality of Life for Injured Troops", http://www.usmedicine.com/articles/novel-use-of-fractional-lasers-for-sca- rring-improves-quality-of-life-for-injured-troops-.html, (Aug. 2012), U.S. Medicine ISSN: 0191-6246. 4 pages.
Stratton, K. et al., "Biological Effects of Laser Radiation II: ESR Studies of Melanin Containing Tissues after Laser Irradiation," Northeast Electronics Research and Engineering Meeting-NEREM Record, IEEE Catalogue No. F-60, pp. 150-151, Nov. 1965.
Strauss et al., "Skin Lipids and Acne," Annu. Rev. Med., 26:27-31, 1975.
Sumian, C.C. et al., "A Preliminary Clinical and Histopathological Study Of Laser Skin Resurfacing Using A frequency-Doubled Nd:YAG Laser After Application of Chromofilm.RTM.," Journal of Cutaneous Laser Therapy, vol. 1, pp. 159-166, 1999.
Sumian, C.C. et al., "Laser Skin Resurfacing Using A Frequency Doubled Nd:YAG Laser After Topical Application Of An Exogenous Chromophore," Lasers in Surgery and Medicine, vol. 25, pp. 43-50, 1999.
Sumian et al., "A new method to improve penetration depth of dyes into the follicular duct: . . . , " J. Am. Acad. Dermotol., 41(2) Part 1:172-175,1999.
Tarasov, L. V., Laser Physics, Translated from Russion by Ram S. Wadhwa, MIR publishers, Moscow, pp. 178-181, Chapter 2, 1983.
Tarijian, et al., "Fractional ablative laser skin resurfacing: A review", Journal of Cosmetic and Laser Therapy, 13:262-264, ISSN 1476/4172. Informa UK Ltd. Sep. 2011, 3 pages.
Taylor, C.R. et al., "Treatment of tattoos by Q-switched ruby laser," Arch. Dermatol. vol. 126, pp. 893-899, Jul. 1990.
Togatov, V.V. et al., "Electronic discharge module for pump systems of solid-state lasers", J. Opt/ Technol., vol. 67, No. 4, pp. 379-382 (2000).
Tuchin, V.V., "Laser light scattering in biomedical diagnostics and therapy," Journal of Laser Applications, vol. 5, No. 2-3, pp. 43-60, 1993.
Unger, W.P., Laser hair transplantation III: Computer-assisted laser transplanting. Dermatol Surg. 1995;21:1047-1055.
Van Bruegel, "Power Density and Exposure Time of He-Ne Irradiation Are More Important Than Total Energy Dose in Photo-Biomodulation of Human Fibroblasts in Vitro," Lasers in Surgery and Medicine, vol. 12 pp. 528-537, 1992.
Vasily, et al., "Non-Ablative Fractional Resurfacing of Surgical and Post-Traumatic Scars", Journal of Drugs in Dermatology, 8(11):998-1005, Nov. 2009, 8 pages.
Walsh, "Laser "Curettage": a Critical Analysis," Periodontology 14:4-12,1993.
Watanabe, S. et al., "Comparative studies of femtosecond to microsecond laser pulses on selective pigmented cell injury in skin," Photochemistry and Photobiology, vol. 53, No. 6, pp. 757-762, 1991.
Watanabe, S. et al.," The Effect of Pulse Duration on Selective Pigmented Cell Injury by Dye Lasers," The Journal of Investigative Dermatology, 88:523, 1987.
Watson, G. M., MS, "Minimally Invasive Therapies of the Prostate," Minimally Invasive Therapy, 1:231-240 (1992).
Wei Tech Ang et al., "Design of All-Accelerometer Inertial Measurement Unit for Tremor Sensing in Hand-Held Microsurgical Instrument," 2003 IEEE International Conference on Robotics and Automation (vol. 2), Taipei, Taiwan, Sep. 14-19, 2003.
Wei Tech Ang et al., "Kalman Filtering for Real-Time Orientation Tracking of Handheld Microsurgical Instrument," 2004 IEEE/RSJ International Conference on Intelligent Robots and Systems (IROS), Sendai, Japan, Sep. 28-Oct. 2, 2004.
Welch, A.J. et al., "Evaluation of cooling techniques for the protection of the epidermis during HD-yag laser iradiation of the skin," Neodymium-Yag Laser in Medicine and Surgery, Elsevier Science Publishing Co., publisher, pp. 195-204, 1983.
Westerman et al., "Argon Laser Irradiation Effects on Sound Root Surfaces: In Vitro Scanning Electron Microscopic Observations," Journal of Clinical Laser Medicine and Surgery, vol. 16, No. 2, pp. 111-115, 1998.
Wilson, S.W., "Passive Alignment of a Semiconductor Laser to an Optical Fiber," Universirty of Maryland, Masters Thesis (1995).
Winters, B.H. et al., "Photochemical Products in Coumarin Laser Dyes," Laboratory for Physical Sciences, College Park, MD, Aug. 26, 1974.
Yang et al., "Hybrid optoelectronics: A polymer laser pumped by a nitride light emitting diode," Applied Physics Letters 92, Jan. 23, 2008.
Yules, R.B. et al., "The effect of Q-switched ruby laser radiation on dermal tattoo pigment in man," Arch Surg, vol. 95, pp. 179-180, Aug. 1967.
Zeitler, E. et al., "Laser Characteristics that Might be Useful in Biology," Laser Applications in Medicine and Biology, vol. I, M.L. Wolbarsht, editor, Plenum Press, publishers, Chapter 1, pp. 1-18, 1971.
Zonios et al., "Skin Melanin, Hemoglobin, and Light Scattering Properties can be Quantitatively Assessed in Vivo Using Diffuse Reflectance Spectroscopy," Journal of Investigative Dermatology,117:1452-1457 (Dec. 2001).
Office Action dated Jul. 12, 2013 in U.S. Appl. No. 12/534,357 (10 pages).
Jacques, Steven L., "Role of Tissue Optics and Pulse Duration on Tissue Effects during High-Power Laser Irradiation" Applied Optics, May 1, 1993, pp. 2447-2454, vol. 32, No. 13, Optical Society of America.
Herd, Robert M. et al., "A Clinical and Histologic Prospective Controlled Comparative Study of the Picosecond Titanium: Sapphire (795 nm) Laser Versus the Q-switched Alexandrite (752 nm) Laser for Removing Tattoo Pigment" Journal of the American Academy of Dermatology, Apr. 1999, pp. 603-606, vol. 40, American Academy of Dermatology, Inc.
Ho, Darwin D.-M. et al.," Laser-Tattoo Removal—A Study of the Mechanism and the Optimal Treatment Strategy via Computer Simulations" Lasers in Surgery and Medicine, 2002, pp. 389-397, vol. 30, Wiley-Liss, Inc.
Kilmer, Suzanne Linsmeier, et al.,"Picosecond and Femtosecond Laser Treatment of Tattoo Ink," Lasers in Surgery and Medicine, Sep. 8, 1996, p. 36, No. 203, Wiley-Liss, Inc.
Ross, CDR E. Victor, et al.,"Comparison of Responses of Tattoos to Picosecond and Nanosecond Q-Switched Neodymium: YAG Lasers" Arch Dermatol, Feb. 1998, pp. 167-171, vol. 134, American Medical Association.

(56) References Cited

OTHER PUBLICATIONS

European Search Report (ESR) and Opinion EP Application No. 07811128.3, dated Sep. 28, 2016.
Derma Chiller advertisement (2 pages) from Paradigm Trex.
"Innovative Non-Surgical Treatment for Barrett's Esophagus", Jul. 1995, see http://7wvvvv.plsaroup.com/da950728.htm.
Brauer, Jeremy A. et al., "Successful and Rapid Treatment of Blue and Green Tattoo Pigment With a Novel Picosecond Laser", Archives of Dermatology, vol. 148, No. 7, 2012, pp. 820-823.
Ertan et al., "Esophagel Adenocarcinoma Associated with Barrett's Esophagus: Long-term Management with Laser Ablation", Am. J. Gastro, 90: pp. 2201-2203, 1995.
Habbema, Louis et al., "Minimally invasive non-thermal laser technology using laser-induced optical breakdown fir skin rejuvenation", J. Biophotonics, vol. 5, No. 2, 2012, pp. 194-199.
Kliewer, Michael L. et al., "Excited State Absorption of Pump Radiation as a Loss Mechanism in Solid-State Lasers", IEEE Journal of Quantum Electronics, vol. 25, 1989, pp. 1850-1854.
Kuizenga, Dirk J. et al., "FM and AM Mode Locing of the Homogenous Laser-Part I: Theory", IEEE Journal of Quantum Electronics, vo 6, No. 11, Nov. 1970, pp. 694-708.
Lee, Junsu et al., "Q-switched Mode-Locking of an Erbium-doped Fiber Laser through Subharmonic Cavity Modulation", Photonics Conference (IPC), 202 IEEE, Sep. 23, 2012, pp. 664665.
Mingxin, Qiu et al., "Performance of a Nd:YV04 microchip laser with continuous-wave pumping at wavelengths between 741 and 825 nm". Applied Optics, vol. 32, No. 12, Apr. 20, 1993, p. 2085.
Ogiso et al, "Phase Transitions of Rat Stratum Corneum Lipids By an Electron Paramagnetic Resonance Study and Relationship of Phase States to Drug Penetration," Biochimica et Biophysica Acta 1301:97-104 (1996).
Oraevsky, Alexander A. et al., "Plasma Mediated Ablation of Biological Tissues with Nanosecond-to-Femtosecond Laser Pulses: Relative Role of Linear and Nonlinear Absorption", IEEE Journal of Selected Topics in Quantum Electronics, vol. 2, No. 4, Dec. 1996, pp. 801-809.
Zayhowski, J.J. et al., "Gain-switched pulsed operation of microchip lasers", Optice Letters, Optical Society of America, U.S. 14:23, Dec. 1, 1989, pp. 1318-1320.
Extended European Search Report & Written Opinion for EP 20155408, dated Apr. 17, 2020.
Bishop, A. I. and P. F. Barker "Subnanosecond Pockels cell switching using avalanche transistors." Review of scientific instruments 77.4: 044701 (2006).
Brauer, J. A., et al. "Use of a picosecond pulse duration laser with specialized optic for treatment of facial acne scarring." JAMA dermatology 151.3: 278-284 (2015).
Coyle, D. B., et al. "An interactive numerical model of diode-pumped, Q-switched/cavity-dumped lasers." Journal of Physics D: Applied Physics 28.3: 452 (1995).
Degnan, John J. "Theory of the optimally coupled Q-switched laser." IEEE Journal of Quantum Electronics 25.2: 214-220 (1989).
Gerstman, B., et al. "Laser induced bubble formation in the retina." Lasers in Surgery and Medicine 18.1: 10-21 (1996).
McDaniel, David. "Gene expression analysis in cultured human skin fibroblasts following exposure to a picosecond pulsed alexandrite laser and specially designed focus optic." Lasers in surgery and medicine 47:8 (2015).
Mirkov, M., et al. "Theoretical analysis of the mechanism producing the histologically observed epidermal changes with a picosecond alexandrite laser with diffractive lens array ", Lasers in Surgery and Medicine 48:1 (2016).
Nielsen, K. P., et al. "Retrieval of the physiological state of human skin from UV-Vis reflectance spectra-a feasibility study." Journal of Photochemistry and Photobiology B: Biology 93.1: 23-31 (2008).
Scheps et al., "Alexandrite Laser Pumped by Semiconductor Lasers," Appl. Phys. Lett. 56(23), 2288-2290 (1990).
Shand, M., and H. Jenssen. "Temperature dependence of the excited-state absorption of alexandrite." IEEE Journal of Quantum Electronics 19.3: 480-484 (1983).

Siegman, "Lasers," University Science Books, 1986, Ch.25, p. 976.
Tanghetti, Emil. "The histology of skin treated with a picosecond alexandrite laser and a fractional lens array." Lasers in surgery and medicine 48.7: 646-652 (2016).
Tanghetti, Emil. "Characterization of the histologic changes in the skin from treatment with a 755nm picosecond alexandrite laser with a fractional optic." Lasers in surgery and medicine. 47:24 (2015).
Thomas, G. M., et al. "Diode-pumped Alexandrite lasers in Q-switched and cavity-dumped Q-switched operation." Optics Express 24.24: 27212-27224 (2016).
Vogel, A., et al. "Shock wave emission and cavitation bubble generation by picosecond and nanosecond optical breakdown in water." The Journal of the Acoustical Society of America 100.1: 148-165 (1996).
Werner, S., et al. "Keratinocyte-fibroblast interactions in wound healing." Journal of investigative dermatology 127.5: 998-1008 (2007).
Kelly et al., "Nonablative Laser Treatment of Facial Rhytides: United States Phase II Clinical Study"., American Society for Laser Medicine and Surgery Abstracts, p. 38.
Apfelberg et al. "Dot or Pointillistic Method for Improvement in Results of Hypertrophic Scarring in the Argon Laser Treatment of Portwine Hemangiomas," Lasers in Surgery and Medicine, 6:552-558 (1987).
Apfelberg, D.B., "A Preliminary Study of the Combined Effect of Neodymium:YAG Laser Photocoagulation and Direct Steroid Instillation in the Treatment of Capillary/Cavernous Hemangiomas of Infancy," Department of Plastic Surgery and Comprehensive Laser Center, Palo Alto Medical Foundation, Palo Alto, CA, pp. 94-103 (1989).
Apfelberg, D.B., "Combination Treatment for Massive Cavernous Hemangioma of the Face: YAG Laser Photocoagulation Pulse Direct Steroid Injection Followed by YAG Laser Resection with Sapphire Scalpel Tips, Aided by Superselective Embolization," Lasers in Surgery and Medicine, 10:217-223 (1990).
Belikov, A.V. et al., "Identification of enamel and dentine under tooth laser treatment," SPIE vol. 2623, Progress in Biomedical Optics Europt Series, Proceedings of Medical Applications of Lasers III, pp. 109-116, Sep. 1995.
Benjavitvilai, C. et al., "Fuzzy Calibration of Magnetometer in Presence of Surgical Microscope," 2005 27th Annual International Conference of the IEEE Engineering in Medicine and Biology Society (IEEE Cat. No. 05CH37611C), Shanghai, China, Aug. 31-Sep. 3, 2005.
Bjerring, P. et al., "Selective Non-Ablative Wrinkle Reduction by Laser," J Cutan Laser Ther, vol. 2, pp. 9-15, 2000.
Blankenau et al., "In Vivo Caries-Like Lesion Prevention with Argon Laser: Pilot Study," Journal of Clinical Laser Medicine and Surgery, vol. 17, No. 6, pp. 241-243, 1999.
Bogdan Allemann, et al., "Laser Principles", Physical and Electronic Properties of Lasers, Basics in Dermatological Laser Applications, Curr. Probl. Dermatol, Basel, Karger. Zurich, Switzerland and Miami, Florida, vol. 42, pp. 7-23, 2011, 17 pages.
Bohm et al., "The Pilosebaceous Unit is Part of the Skin Immune System," Dermatology, 196:75-79, 1998.
Boiteux, M., et al., "A Transverse Flow Repetitive Dye Laser," Applied Optics, 9, 514 (1970).
Boulnois, J., "Photophysical Processes in Recent Medical Laser Developments: a Review," Lasers in Medical Science, vol. 1:47-66 (1986).
Britt et al., "The Effect of pH or Photobleaching of Organic Laser Dyes", IEEE J. Quantum Electron. (Dec. 1972), 913-914.
Burlamacchi et al., "A Simple Reliable Waveguide Dye Laser for Ophthalmological Applications," Rev of Sci Instrum; vol. 46; No. 3; pp. 281-283, Mar. 1975.
Chan, E.K., "Effects of Compression on Soft Tissue Optical Properties," IEEE Journal of Selected Topics in Quantum Electronics, vol. 2, No. 4, pp. 943-950 (Dec. 1996).
Costello, A. et al., "Nd:YAG Laser Ablation of the Prostate as a Treatment for Benign Prostatic Hypertrophy," Lasers in Surgery and Medicine, 12:121-124 (1992).
Cunliffe, "Acne Vulgaris. The Past, the Present and the Future," Acta Bermatovener (Stockh) Suppl. 120, pp. 34-38, 1985.

(56) References Cited

OTHER PUBLICATIONS

Dabrowska, "Intravital Treatment of the Pulp with Stimulation Laser Biostimulation," Abstract Rocz-Akad-Med-Bialymst. 1997; 42(1): 168-76.
Dierickx, C.C. et al., "Thermal Relaxation of Port-wine Stain Vessels Probed in Vivo: The Need for 1-10 Millisecond Laser Pulse Treatment," The Journal for Investigative Dermatology, pp. 709-714 (1995).
Dixon et al. "Hypertrophic Scarring in Argon Laser Treatment of Port-Wine Stains," Plastic and Reconstructive Surgery, 73:771-777 (1984).
Dock et al., "Clinical Histologic and Ultrastructural Evaluation of Solar Elastosis Treated With the Pulsed Dye Laser," American Society for Laser Medicine and Surgery Abstracts, p. 54 (Apr. 1997).
Doukas et al., "Transdermal Drug Delivery With a Pressure Wave," Advanced Drug Delivery Reviews 56 (2004), pp. 559-579.
Dover J.S et al., "Pigmented guinea pig skin irradiated with Q-switched ruby laser pulses," Arch Dermatol, vol. 125, pp. 43-49, Jan. 1989.
Dufresne et al., "Squamous cell carcinoma arising from the follicular occlusion triad," J. Am. Acad. Dermatol. 35(3), Part 1:475-477, 1996.
Fallon Friedlander, "Effective Treatment of Acne Fulminans-Associated Granulation Tissue with the Pulsed Dye Laser," Pediatric Dermatology, 15(5):396-398, 1998.
Finkelstein L.H. et al., "Epilation of hair-bearing urethral grafts using the neodymium:yag surgical laser," Journal of Urology, vol. 146, pp. 840-842, Sep. 1991.
Fiskerstrand E.J. et al., "Hair Removal with Long Pulsed Diode Lasers: A Comparison Between Two Systems with Different Pulse Structures," Lasers in Surgery and Medicine, vol. 32, pp. 399-404, 2003.
Forrest-Winchester et al., "The Effect of Infrared Laser Radiation on Dentinal Permeability in vitro," Department of Dentistry, University of Queensland Dental School, pp. 1-8, 1992.
Friedman-Binrbaum et al., "Seborrheic Skin and Acne Vulgaris as Protective Factors against the Development of Basal Dell Epithelioma," Dermatolgica, 183:160-163, 1991.
Furomoto, H., "Dye Chemisry and System Study for Optimum Laser Operation at 436 NM Using the LFDL-10 Laser," Prepared for Burlington Division Geophysical Corporation of America, pp. 1-23, Mar. 1982.
Ginsbach et al. "New Aspects in the Management of Benign Cutameous Tumors," Laser 79 Opto-Electronics, Munich Conference Proceedings, 344-347 (1979).
Goldberg, "Lasers for Facial Rejuvenation", Am J. Clin. Dermatol., 4(4):225-234, 2003, 10 pages.
Goldberg, "Nonablative Resurfacing", Clinics in Plastic Surgery, Skin Laser and Surgery Specialists of New York and New Jersey. Westwood, New Jersey vol. 27, No. 2, Apr. 2000, 6 pages.
Goldman, L. et al., "Effect of the laser beam on the skin, III Exposure of cytological preparations," Journal of Investigative Dermatology, vol. 42, pp. 247-251, 1964.
Goldman, L. et al., "Effect of the laser beam on the skin, Preliminary report" Journal of Investigative Dermatology, vol. 10, pp. 121-122, 1963.
Goldman, L. et al., "Impact of the laser on nevi and melanomas," Archives of Dermatology, vol. 90, pp. 71-75, Jul. 1964.
Goldman, L. et al., "Laser action at the cellular level," JAMA, vol. 198, No. 6, pp. 641-644, Nov. 1966.
Goldman, L. et al., "Laser treatment of tattoos, A preliminary survey of three year's clinical experience," JAMA, vol. 201, No. 11, pp. 841-844, Sep. 1967.
Goldman, L. et al., "Long-term laser exposure of a senile freckle," ArchEnviron Health, vol. 22, pp. 401-403, Mar. 1971.
Goldman, L. et al., "Pathology, Pathology of the effect of the laser beam on the skin," Nature, vol. 197, No. 4870, pp. 912-914, Mar. 1963.
Goldman, L. et al., "Preliminary investigation of fat embolization from pulsed ruby laser impacts of bone," Nature, vol. 221, pp. 361-363, Jan. 1969.
Goldman, L. et al., "Radiation from a Q-switched ruby laser, Effect of repeated impacts of power output of 10 megawatts on a tattoo of man," Journal of Investigative Dermatology, vol. 44, p. 69-71, 1965.
Goldman, L. et al., "Replica microscopy and scanning electron microscopy of laser impacts on the skin," Journal of Investigative Dermatology, vol. 52, No. 1, pp. 18-24, 1969.
Goldman, L. et al., "The biomedical aspects of lasers," JAMA, vol. 188, No. 3, pp. 302-306, Apr. 1964.
Goldman, L. et al., "The effect of repeated exposures to laser beams," Acta derm.-vernereol., vol. 44, pp. 264-268, 1964.
Goldman, L., "Dermatologic manifestations of laser radiation," Proceedings of the First Annual Conference on Biologic Effects of Laser Radiation, Federation of American Societies for Experimental Biology, Supp. No. 14, pp. S-92-S-93, Jan.-Feb. 1965.
Goldman, L., "Effects of new laser systems on the skin," Arch Dermatol., vol. 108, pp. 385-390, Sep. 1973.
Goldman, L., "Laser surgery for skin cancer," New York State Journal of Medicine, pp. 1897-1900, Oct. 1977.
Goldman, L., "Surgery by laser for malignant melanoma," J. Dermatol. Surg. Oncol., vol. 5, No. 2, pp. 141-144, Feb. 1979.
Goldman, L., "The skin," Arch Environ Health, vol. 18, pp. 434-436, Mar. 1969.
Goldman, L., Biomedical Aspects of the Laser, Springer-Verlag New York Inc., publishers, Chapts. 1, 2 & 23, 1967.
Altea Therapeutics, "The PassPort Patch makes medicines more effective and safer," www.alteatherapeutics.com, Sep. 30, 2004.
Goldman, Leon, et al. "Treatment of Basal Cell Epithelioma by Laser Radiation," JAMA, Epithelioma—Goldman & Wilson, vol. 189, No. 10, pp. 773-775, Laser Laboratory of the Children's Hospital Research Foundation.
Altshuler, G. et al. "The ring resonator of optical quantum generator" Aug. 15, 1975. Invention description to certificate of authorship No. 719439.
Altshuler, G. et al. "The modulator of optical radiation intensity" Oct. 10, 1977. Invention description to certificate of authorship No. 741747.
Altshuler, G. et al. "Laser interferometric device to determine non-linearity of an index of refraction of optical medium." Sep. 15, 1986. Invention description to certificate of authorship No. SU (11) 1257475 A1.
Altshuler, G et al. "The way of determination of non-linearity of an index of refraction of optical medium" Jul. 30, 1987. Invention description to certificate of authorship No. SU (11) 1326962 A1.
Altshuler, G. et al. "The way of investigation of radiation time structure of optical quantum generator." Jul. 9, 1974. Invention description to certificate of authorship No. 532304.
Mumford, Jaime, et al.," Effect of Soft Laser Treatment on Wound Healing in the Hampster Oral Mucosa," Lasers in Surgery and Medicine, Supp. 8, Abstracts, Aug. 25, 1996.Biostimulation/Low Engergy Laser, pp. 5-8, American Society for Laser Medicine and Surgery Abstracts.
Walsh,L.J., "The current status of low level laser therapy in dentistry. Par 1. Soft tissue applications." Aust. Dent. J., Aug. 1997; 42(4): pp. 247-254. Department of Dentistry, University of Queensland.
International Search Report corresponding to PCT/US07/17536.
Examination Report relating to corresponding EP Application No. 07811128.3.
Supplementary European Search Report relating to corresponding EP 07811128.
Zapka, et al., "Pulse Slicing and Pockels Cell Shutters," J. Phys. E: Sci, Instrum., vol. 15, 1982.
Russel, et al., "Flash-Lamp-Excited Self-Injection-Seeded Q-Switch Ti: Al2O3 Laser Oscillator," Applied Optics, vol. 35, No. 24, Aug. 20, 2996.
Ellenberger, et al., "Single-Frequency Nd:Glass Laser Oscillator with Pulse-Transmission-Mode Q-Switch," Optics Communications, vol. 81, No. 6, Mar. 15, 1991.
English Abstract of JP 55077187.
International Preliminary Report on Patentability relating to corresponding PCT/US07/17536.

(56) References Cited

OTHER PUBLICATIONS

[No Author] Bioptron Light Therapy System. Website print-out, accessed Jul. 13, 2006 (2 pages).
[No Author] IPG Data Sheet for TFL Thulium Laser, Jun. 2001.
[No. Author] Webpage www.gallery.com-RUTILE (Titanium Oxide)- Retrieved Oct. 3, 2011 from Http://www.galleries.com/minerals/oxides/rutile/rutile.htm. 2 pages.
[No Author] Energy Systems Corompration, "A Practical Guide for the PhotoDem.RTM.VL user," Haifa, Israel, Commercial Brochure 8 pages, Oct. 1995.
[No Author] "Final Report on the LFDL-10 Laser System for the GCA Corporation," Candela Corp., Natick, MA, Section II, subsection 5, pp. 13-15 & 27, Mar. 1982.
[No Author] "Fractional Photothermolysis Redefines Facial Skin Regeneration Science," Aesthetic Buyers Guide, Mar./Apr. 2004, www.miinews.com, pp. 1-4.
[No Author] "Hydrogel Dressings Contain Particles During Laser Therapy," Dermatology Times, ISSN-01966197, p. 26 (1994).
[No Author] "Instruction Manual, TFDL-10," Adapted for SLAC, Candela Corporation, Natick, Oct. 1985.
[No Author] "Lasers Battle for Prostatectomy Market," Medical Laser Industry Report, 5:1-3 (Aug. 1991).
[No Author] "LFDL-8 Instruction Manual," Candela Laser Corporation, Wayland, MA Revised Oct. 1987.
[No Author] "LFDL-8 Instruction Manual," Candela Laser Corporation, Wayland, MA, Jan. 1982, Revised Jun. 1987.
[No Author] "LFDL-8 Instruction Manual," Cynosure, Inc., Bedford, MA, Revised Nov. 1992.
[No. Author] "Prostate Enlargement: Benigh Prostatic Hyperplasia," brochure from U.S. Department of Health and Human Services, pp. 1-14, (at least by 1992).
[No Author] "Special Instruction and Test Results for the LFDL-2 Wave Guide Laser," Candela Laser Corporation, Wayland, MA, Sep. 1982.
[No Author] "The Laser TURP Advantage," INTRA-SONIX, Inc. pp. 1-4 (1991).
[No Author] Beckman Laser Institute "Experimental PDT to Prevent Esophegus Cancer," (8 pages) 1996.
[No Author] Cynosure Dioderm 510(k) Notification K992765 for Cynosure, Inc. to Food and Drug Administration, dated Aug. 16, 1999 and Aug. 20, 1999 (Additional Information).
[No Author] RELIANT Technologies, Inc. "Physicians Guide: Understanding Fraxel Laser Treatment," pp. 1-10 (2004).
[No Author] Ritter Sybron Corporation, "Electrosurgery, A Guide for Operating Room Personnel," pp. 1-22, (Jun. 1976).
[No Author] Selective Photothermolysis of Sebaceous Glands, Department of Health and Human Services, Public Health Service, Small Business Innovation Research Program II Grant Application, CYNOSURE, Inc., dated: Jul. 27, 2000, pp. 17-39 and 43-44.
"American Society for Laser Medicine and Surgery Abstracts," Lasers in Surgery and Medicine, Supplement 6, p. 46 (1994).

Anderson, R.R., et al., "Microvasculature Can Be Selectively Damaged Using Dye Lasers: A Basic Theory and Experimental Evidence in Human Skin," Lasers in Surgery and Medicine 1:263-276 (1981).
Altshuler et al., "Human Tooth as an Optical Device," SPIE vol. 1429 Holography and Interferometry and Optical Pattern Recognition in Biomedicine, pp. 95-104, 1991.
Altshuler et al., "Modern Optics and Dentistry," Laser in Dentistry, pp. 283-297, 1995.
Altshuler et al., "New Optical Effects in the Human Hard Tooth Tissues," Lasers and Medicine, Proc. SPIE vol. 1353, pp. 97-102, 1989.
Altshuler, et al., "Self Canalization of Laser Microbeam in Tissue as Fundamental Mechanism of Fractional Skin Resurfacing", Lasers in Surgery and Medicine Supple 15, 21, 2003.
Altshuler, G.B. et al., "Acoustic response of hard dental tissues to pulsed laser action," SPIE, vol. 2080, Dental Application of Lasers, pp. 97-103, 1993.
Altshuler, G.B. et al., "Extended theory of selective photothermolysis," Lasers in Surgery and Medicine, vol. 29, pp. 116-432, 2001.
Amy, R.L. et al., "Selective mitochondrial damage by a ruby laser microbeam: An electron microscopic study," Science, vol. 15, pp. 756-758, Nov. 1965.
Anderson, R.R. et al., "Selective photothermolysis: Precise microsurgery by selective absorption of pulsed radiation," Science, vol. 220, pp. 524-527, Apr. 1983.
Anderson, R.R. et al., "The optics of human skin," Journal of Investigative Dermatology, vol. 77, No. 1, pp. 13-19, 1981.
Angelis, et al., "Fractional, Non-Ablative Laser Therapy for the Treatment of Striae Distensae", White Paper published by Palomar Medical Technologies, Inc. (2009) 5 pages.
Apfelberg et al. "Analysis of Complications of Argon Laser Treatment for Port Wine Hemangiomas with Reference to Striped Technique," Lasers in Surgery and Medicine, 2:357-371 (1983).
"American Society for Laser Medicine and Surgery Abstracts," Lasers in Surgery and Medicine, p. 51.
Goldman, M.P., "Sclerotherapy —Treatment of Varicose and Telangiectatic Leg Veins," Second Edition, Mosby, pp. 454-467 (No. Date Given).
Mccullough, David L., M.D., "This month in Investigative Urology: Transurethral Laser Treatment of Benign Prostatic Hyperplasia". The Journal of Urology, vol. 146, 1126-1127, Oct. 1991.
Togatov, V.V. et al., "Discharge Circuit for Solid-State Lasers Pumping," Optical Journal, vol. 67, No. 4, pp. 92-96 (2000).
Knipe et al. "Effects of Secondary Chemical Reactions Upon the performance of Dye Lasers" Journal of Photochemistry, 23 (1983) 117-130.
Fletcher, Aaron N. "FY 1980 Report on Dye Laser Materials" Naval Weapons Center China lake, California 93555. Feb. 1981.
Mar. 16, 2022—(SG) Search Report & Written Opinion—App. No. 11202008151Q.

* cited by examiner

Q-SWITCHED CAVITY DUMPED SUB-NANOSECOND LASER

RELATED APPLICATION DATA

This application is a National Stage Application under 35 U.S.C. 371 of co-pending PCT application PCT/US2019/019583 designating the United States and filed Feb. 26, 2019; which claims the benefit of which claims priority to U.S. Provisional Application No. 62/635,174 filed on Feb. 26, 2018 and U.S. Provisional Application No. 62/653,767 filed on Apr. 6, 2018, each of which is hereby incorporated herein by reference in its entirety for all purposes.

FIELD

The present disclosure relates to apparatuses and methods for delivering laser energy having a short pulse duration (e.g., less than about 1 nanosecond) and high energy output per pulse (e.g., greater than about 100 millijoules). The desired operating parameters are achieved, in part, by a laser configuration including a laser cavity designed to have a sub-nanosecond round trip time so as to produce an output pulse duration in the sub-nanosecond range. The laser configuration also includes Q-switching and cavity dumping features. As a result, laser energy suitable for a number of applications, including cosmetic and medical applications, for example, treating and removing pigment particles such as those introduced to the human body as tattoos, may be generated using a relatively simple apparatus.

BACKGROUND

Lasers are recognized as controllable sources of radiation that are relatively monochromatic and coherent (i.e., have little divergence). Laser energy is applied in an ever-increasing number of areas in diverse fields such as telecommunications, data storage and retrieval, entertainment, research, and many others. In the area of medicine, lasers have proven useful in surgical and cosmetic procedures where a precise beam of high energy radiation causes localized heating and ultimately the destruction of unwanted tissues.

The principle of selective photothermolysis underlies many conventional medical laser therapies to treat diverse dermatological problems such as leg veins, portwine stain birthmarks, and other ectatic vascular and pigmented lesions. The dermal and epidermal layers containing the targeted structures are exposed to laser energy having a wavelength that is preferentially or selectively absorbed in these structures. This leads to localized heating to a temperature (e.g., to about 70° C. or higher) that denatures constituent proteins or disperses pigment particles. The fluence, or energy per unit area, used to accomplish this denaturation or dispersion is generally based on the amount required to achieve the desired targeted tissue temperature, before a significant portion of the absorbed laser energy is lost to diffusion. The fluence must, however, be limited to avoid denaturing tissues surrounding the targeted area.

In addition to fluence, pulse duration and pulse intensity can impact the degree to which laser energy diffuses into surrounding tissues during the pulse and/or causes undesired, localized vaporization. In terms of the pulse duration of the laser energy used, conventional approaches have focused on maintaining this value below the thermal relaxation time of the targeted structures, in order to achieve optimum heating. For the small vessels contained in portwine stain birthmarks, for example, thermal relaxation times and hence the corresponding pulse durations of the treating radiation are often on the order of hundreds of microseconds to several milliseconds.

The use of even shorter pulses, however, results in a change from photothermal to photomechanical processes. The latter mechanism is invoked by applying laser pulses having a duration that is below the acoustic transit time of a sound wave through targeted particles. This causes pressure to build up in the particles, in a manner analogous to the accumulation of heat within a target irradiated by laser pulses having a duration that is below the thermal relaxation time.

Photomechanical processes described above are useful in the area of treating skin pigmentations including tattoos, portwine stains, and other birthmarks. Stable tattoos are likely composed of pigment particles having in one aspect exemplary diameters on the order of 1 to 4 micrometers. According to one exemplary aspect, each particle includes sub-particles with diameters on the order of 20 to 400 nanometers. According to one exemplary aspect, each particle includes sub-particles with diameters on the order of 40 to 100 nanometers. As the speed of sound in many solid media is approximately 3000 meters/second, the acoustic transit time across such particles, and consequently the laser pulse duration required to achieve their photomechanical destruction, is as low as hundreds of picoseconds. The acoustic transit time of a sound wave in a particle is calculated by dividing the radius of the particle by the speed of sound in the particle.

In addition to such short pulse durations, high energy laser pulses are needed for significant disruption of tattoo pigment particles and other pigmentations. Required fluences of several joules per square centimeter and treatment spot sizes of a few millimeters in diameter translate to a desired laser output with several hundred millijoules (mJ) per pulse or more. Unfortunately, current systems capable of such short pulse duration and high energy output can be too complex and/or expensive for practical use in the treatment or removal of tattoos and other pigmentations. These devices generally require two or more lasers and amplifier stages, together with multiple electro-optical and/or acousto-optic devices.

Consequently, there is a need in the art for laser apparatuses of relatively low complexity that can generate laser light in the picosecond pulse range and with energies high enough to provide usage in cosmetic or medical applications.

SUMMARY

Embodiments of the present disclosure are directed to a laser configuration or laser design or laser system that includes a laser oscillator having dimensions suitable to produce a sub-nanosecond cavity round trip time that is used to generate laser light with a sub-nanosecond pulse duration. Exemplary laser configurations also generate pulse energies on the order of a few hundred mJ per pulse and above. Representative laser configurations include a Q-switching feature. Representative laser configurations include a cavity dumping feature. According to one aspect, the laser configurations described herein are used to generate and deliver pulsed laser energy with pulse characteristics suitable for a number of practical applications. Such pulse characteristics include a sufficiently short duration and/or a sufficiently high energy for the photomechanical treatment of skin pigmentations and pigmented lesions, both naturally-occurring (e.g., birthmarks), as well as artificial (e.g., tattoos).

According to one aspect, a device and method are provided for generating high energy sub-nanosecond pulses from a laser oscillator without additional amplifier stages. In this aspect, the laser configuration lacks additional amplifier stages. In an additional aspect, the laser configuration lacks modelocking. In an additional aspect, the laser configuration lacks high frequency periodic loss modulation that can be associated with a laser oscillator.

In one aspect, the laser configuration includes only a single resonator and lasing (or gain) medium. The laser configuration includes two end mirrors between which are positioned an electro-optical device such as a Pockels cell, a polarizer and a gain medium. The distance between the two reflective mirrors is designed to generate a cavity round trip time that is less than one nanosecond, i.e. a sub-nanosecond cavity round trip time. The laser configuration is designed for cavity dumping through the polarizer. According to one aspect, the cavity dumping is achieved by increasing the output coupling of the laser cavity so that all or substantially all of the energy circulating in the laser cavity is extracted out of the cavity. According to one aspect, the circulating energy is extracted from the cavity (or "dumped") over a period of time equal to or approximately equal to the cavity round trip time. In this manner, the pulse duration of the output pulse is equal to or substantially equal to the cavity round trip time. According to one aspect, in order to achieve a sub-nanosecond laser pulse duration, the cavity round trip time is less than one nanosecond. According to one aspect, in order to achieve an energy per pulse of 200 mJ and higher, the laser resonator is first Q-switched and then cavity dumped, i.e. the laser energy is extracted from the laser resonator in a manner to achieve cavity dumping as that term is known in the art. In one aspect, cavity dumping is a method known in the art for extracting pulses from a laser using an optical switch in the laser resonator, such as an acousto-optic modulator or electo-optic modulator which is turned on briefly for pulse extraction.

According to one aspect, the laser configuration is simplified in terms of components required to produce a sub-nanosecond laser pulse output with energy of greater than 10 mJ or greater than 100 mJ. The resonator length need not be adjusted and the components are few and the laser configuration is compact. According to one aspect, the laser configuration and method includes reflecting laser energy between two totally reflective or two substantially totally reflective mirrors disposed at opposite ends of a resonator and through a polarizer and an electo-optical device within the resonator and positioned along the optical path (or longitudinal axis) of the resonator. A lasing (or gain) medium, for example a flash lamp pumped laser rod, is also positioned along the optical axis. The laser resonator has a cavity round trip time of less than 1 nanosecond. According to one aspect, the laser resonator is Q-switched and cavity dumped to generate the sub-nanosecond pulses having an energy, for example, on the order of 100 mJ or 200 mJ. The pulse is expelled from the resonator at the polarizer.

According to one aspect, a representative apparatus includes a resonator having first and second mirrors, each of which is totally or substantially totally reflective, disposed at opposite ends of the resonator. The apparatus also includes a lasing material (e.g., a solid state lasing medium), an electro-optical device (e.g., a Pockels cell), and a polarizer, all of which are positioned along the optical axis of the resonator. The electro-optical device is positioned on the optical axis between the polarizer and the (arbitrarily denoted) "first" mirror. In other embodiments, the laser configuration or apparatus described herein may include a resonator of fixed length, and often includes a single resonator only of fixed length, which is configured to generate laser radiation with the desirable pulse duration and energy characteristics as discussed herein. In other embodiments, the first mirror and the second mirror are fixed within the housing to define a static resonator chamber having a sub-nanosecond round trip time. The resonator may be included in an apparatus, for example, in the absence of any other components that would materially affect its basic and novel characteristics.

The pulsed laser energy generated according to methods of the present disclosure may have at least about a 100 mJ/pulse, and often will have a pulse from about 200 to about 900 mJ/pulse, as required for applications described herein, such as the removal or dispersion of pigment particles as often used to form tattoos. As is also desired in these applications, the pulsed laser energy generally has a pulse duration of between 100 picoseconds and 900 picoseconds, between 500 picoseconds and 900 picoseconds or between 500 picoseconds and 750 picoseconds. As stated previously, any of the methods described above may be performed without the need to adjust resonator length, as the resonator length is fixed to produce a sub-nanosecond round trip time, and with the few components comprising the laser resonator.

In another embodiment, the present disclosure provides a method for treating a skin pigmentation, such as a tattoo, a portwine stain, or a birthmark. According to one aspect, a diffractive lens array optic (i.e., a fractional lens array), such as described in Tanghetti, Lasers in Surgery and Medicine, 48:646-652 (2016) hereby incorporated by reference in its entirety can be used to deliver laser light from the device as described herein to the target tissue and as described by Anderson et al. U.S. Pat. No. 6,997,923 each of which are hereby incorporated by reference in its entirety. Accordingly, a fractional laser light treatment method is provided herein.

The method comprises exposing pigmented skin of a patient to pulsed laser energy with pulses having a duration of between 100 ps and 900 ps and an energy of at least 100 mJ. The pulsed laser energy is generated according to any of the methods, or using any of the apparatuses or laser configurations, discussed above.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 4($b$), 4($c$), 4($d$) and 4($e$) illustrate calculated voltage transients (dashed line) and output pulse shapes (solid line) from a cavity dumped resonator. Time scale, transient times and output pulse durations are in units of cavity round trip times. Pockels cell voltage amplitude in units of quarter wave voltage.

FIG. 4($f$) shows a contour plot for the calculated output pulse duration.

Figure 1:
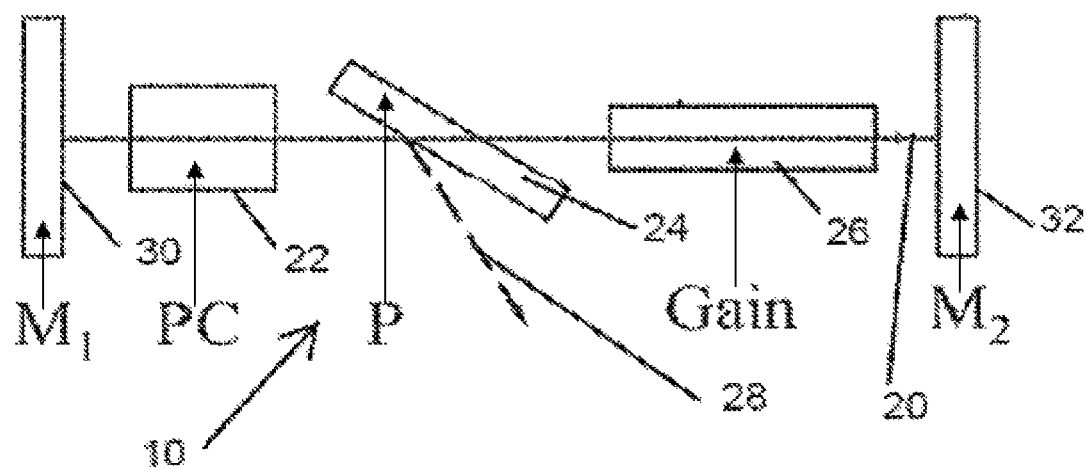
FIG. 1 is a graphical representation of a resonator layout, wherein the cavity dumped pulse is extracted along the dashed arrow.

The features of the embodiments referred to in the figures are not necessarily drawn to scale and should be understood to present an illustration of aspects of the present disclosure and/or principles involved. Some features depicted in the figures have been enlarged or distorted relative to others, in order to facilitate explanation and understanding. The same reference numbers are used in the figures for similar or identical components or features shown in the various embodiments. Laser devices, as disclosed herein, will have configurations, components, and operating parameters determined, in part, by the intended application and also the environment in which they are used.

DETAILED DESCRIPTION

Aspects of the present disclosure are directed to embodiments of a laser configuration including a laser oscillator having a length providing a sub-nanosecond round trip time. According to one aspect, the length of the laser oscillator is fixed. According to certain embodiments, the laser oscillator has a cavity dumping feature. According to certain embodiments, the laser oscillator has a Q-switching feature. According to certain aspects, the laser oscillator is Q-switched and then cavity dumped. According to certain aspects, the laser oscillator is Q-switched and then cavity dumped over a period of time that is about equal to the laser oscillator round trip time. In this manner, the pulse duration of the output pulse is equal to or about equal to the laser oscillator round trip time. An exemplary output pulse is within the sub-nanosecond range. According to one aspect, the Q-switching feature provides energy on the order of a few hundred mJ and above.

Cavity dumping is a known technique where the output coupling of the laser cavity is increased very fast so that substantially all of the energy circulating in the laser cavity is "dumped" out of the cavity as described, for example, in Siegman, "Lasers," University Science Books, 1986. Ideally, the circulating energy is dumped out of the cavity over a period of time equal to the cavity round trip time. Therefore, the pulse duration of the output pulse is equal to the cavity round trip time. Then, in order to achieve a sub-nanosecond laser pulse duration, the cavity round trip time is less than 1 nanosecond.

The requirement for relatively large energy per pulse, e.g., 200 mJ and above is achieved by the resonator being Q-switched and then cavity dumped. Q-switched cavity dumped designs have been reported and are useful in aspects of the laser designs and methods described herein. See for example, Thomas, *Opt. Expr.*, v. 24, p. 27212; Coyle, *J. Phys. D.*, v. 28, p. 452; Wayne, U.S. Pat. No. 4,176,327; Guch, U.S. Pat. No. 6,580,732; Rieger, U.S. Pat. No. 7,006,540; and Zucker US 2007/0280305 each of which is hereby incorporated herein by reference in its entirety.

According to one aspect, the laser configurations described herein generate light pulses having a pulse duration of several hundred picoseconds to cause the photomechanical disruption, through the use of sound (or pressure) waves, of tattoo pigment particles and other components of pigmented lesions. Mechanical disruption of the pigment particles facilitates removal of the pigment particles by the body's natural removal processes such as those associated with the immune system. These pulse durations are of the same order as the acoustic transit time across particles having an exemplary diameter according to one aspect of from about 1 to about 4 micrometers, which are otherwise sufficiently large to remain stable in skin tissue (e.g., without being cleared by normal immune system responses).

Embodiments of the present disclosure generate and optionally deliver laser energy having a pulse duration generally less than about 1 nanosecond, typically less than about 900 picoseconds (ps), about 800 picoseconds (ps), about 700 picoseconds (ps), about 600 picoseconds (ps), about 500 picoseconds (ps), about 400 picoseconds (ps), about 200 picoseconds (ps), and often less than about 250 ps. Common pulse duration values according to some embodiments are in the range from about 100 ps to about 900 ps, from about 150 ps to about 800 ps, from about 200 ps to about 700 ps, from about 300 ps to about 600 ps, from about 100 ps to about 300 ps, from about 500 ps to about 900 ps or from about 500 ps to about 750 ps. The above values generally represent less than several (e.g., from about one to about three or from about one to about five) acoustic transit times for pigmentation particles having a diameter in the range from about 1 to about 10 microns.

Also characteristic of laser energy that is effective for treating or removing skin pigmentations is a relatively high level of energy output. For example, fluences required to achieve significant disruption of pigment particles are generally in the range from about 1 to about 10 J/cm$^2$. For viable treatment methods having a treatment area or spot size of a few millimeters in diameter, the required laser output is at least about 100 mJ per pulse, and often in the range from about 200 to about 800 mJ per pulse.

FIG. 1 depicts a representative embodiment of a laser resonator 10 according to the present disclosure, which is capable of achieving the above pulse duration and energy output parameters, suitable for the effective treatment of pigmented lesions through photomechanical means. Advantageously, the apparatus includes a resonator (or laser cavity) capable of generating laser energy having the desirable pulse duration and energy per pulse, as described herein. The resonator has a characteristic longitudinal or optical axis 20 (i.e., the longitudinal flow path for radiation in the resonator), as indicated by the solid line. According to one aspect, the length of the optical axis is fixed. Also included in the representative apparatus shown are an electro-optical device, in this case a Pockels cell 22 (PC), a polarizer 24 (P) (e.g., a thin-film polarizer) and a gain medium 26 (Gain). During operation, the laser pulse output will be obtained along output path 28 indicated by the dashed line. According to one aspect, the laser pulse output is delivered to a target tissue using a laser light delivery device known to those of skill in the art. Such a laser light delivery device can include a single lens as is known in the art or a lens array as is known in the art. An exemplary lens array can be a fractional lens array as is known in the art.

At opposite ends of the optical axis 20 of the resonator are a first mirror 30 (M1) and a second mirror 32 (M2) having complete reflectivity or substantially complete reflectivity. The term "substantially complete reflectivity", and equivalent terms such as "substantially totally reflective" are used to indicate that the mirrors 30 and 32 completely reflect incident laser radiation of the type normally present during operation of the resonator, or reflect at least 90%, preferably at least 95%, and more preferably at least 99% of incident radiation. The length of the laser resonator, i.e. the length between the incident faces where light is reflected along the axis 20 of the first mirror 30 and the second mirror 32 supports a cavity round trip time of less than one nanosecond. The mirror reflectivity is to be distinguished from the term "effective reflectivity," which is not a property of the mirror itself but instead refers to the effective behavior of the combination of second mirror 32, Pockels cell 22, and polarizer 24 that is induced by the particular operation of the Pockels cell 22 to cause the light to be extracted from the laser cavity through polarizer 24.

In particular, a laser pulse traveling from lasing or gain medium 26 towards first mirror 30 will first pass through polarizer 24, then Pockels cell 22, reflect at first mirror 30, traverse Pockels cell 22 a second time, and finally pass through polarizer 24 a second time before returning to gain medium 26 and to second mirror 32 where the laser pulse will reflect and return to the gain medium 26. Depending upon the bias voltage applied to Pockels cell 22, the entirety of the energy in the pulse will be rejected at polarizer 24 and exit the resonator along output path 28 which is exemplary of "cavity dumping".

The lasing or gain medium 26 may be pumped by any conventional pumping device known to those of skill in the art (not shown) such as an optical pumping device (e.g., a flash lamp) or possibly an electrical or injection pumping device. A solid state lasing medium and optical pumping device are preferred for use as described in the present disclosure.

According to one aspect, the laser resonator 10 includes Q-switching and cavity dumping capabilities. The orientation or positioning or arrangement of the resonator elements depicted in FIG. 1 is designed, such as to be compact, so that the cavity round trip time is less than 1 nanosecond (ns). The two end mirrors 30 (M1) and 32 (M2) are static, i.e. are not moveable along the axis and have high reflectivity, such as about 100%, at the laser-operating wavelength. In case of coaxial laser pumping of the gain medium, mirror 32 (M2), proximal to the gain medium, is dichroic coated and has high reflectivity, such as about 100%, at the laser operating wavelength, and minimum reflectivity, such as about 0%, at the pumping wavelength.

Representative solid state lasers operate with an Alexandrite or a titanium doped sapphire (Ti:S) crystal. Alternative solid lasing media include a yttrium-aluminum garnet crystal, doped with neodymium (Nd:YAG laser). Similarly, neodymium may be used as a dopant in the pervoskite crystal (Nd:YAP or Nd:YAlO$_3$ laser) or a yttrium-lithium-fluoride crystal (Nd:YLF laser). Other rare earth and transition metal ion dopants (e.g., erbium, chromium, and titanium) and other crystal and glass media hosts (e.g., vanadate crystals such as YVO$_4$, fluoride glasses such as ZBLN, silicaglasses, and other minerals such as ruby) of these dopants may be used as lasing media. According to one aspect, the gain (or laser) medium is preferably a compact solid-state laser crystal. Examples include Alexandrite, Nd:YAG, Nd:YLF, Yb:YAG, or other rare earth, or Cr doped crystals or glasses (e.g., Cr:LiSAF). Preferably, the gain medium is a relatively low gain material such as Alexandrite.

The above mentioned types of lasers generally emit radiation, in predominant operating modes, having wavelengths in the visible to infrared region of the electromagnetic spectrum. In an Nd:YAG laser, for example, population inversion of Nd$^{+3}$ ions in the YAG crystal causes the emission of a radiation beam at 1064 nm as well as a number of other near infrared wavelengths. It is also possible to use, in addition to the treating radiation, a low power beam of visible laser light as a guide or alignment tool. Alternative types of lasers include those containing gas, dye, or other lasing media. Semiconductor or diode lasers also represent possible sources of laser energy, available in varying wavelengths. In cases where a particular type of laser emits radiation at both desired and undesired wavelengths, the use of filters, reflectors, and/or other optical components can aid in targeting a pigmented lesion component with only the desired type of radiation.

In cases when the gain medium has relatively low absorption at the wavelength of coaxial pumping through the dichroic mirror M2 (32), the optical surface of the gain that is distal with respect to dichroic mirror M2 (32) can be dichroic coated to achieve about 0% reflectivity for the lasing wavelength and about 100% reflectivity for the pumping wavelength. According to this aspect, the dichroic coating on the gain medium allows for two-pass pumping with the pump light.

The apparatuses and methods disclosed herein are in many cases significantly simplified due to the reduced number of components and/or reduced demands in terms of bias voltage and other operating parameters. Devices may be operated using a modulated waveform according to the requirements and parameters set forth herein, and using suitable electronic configuration or various equivalent configurations as would be apparent to one of ordinary skill, having the benefit of the present disclosure. Other embodiments of the disclosure may involve the introduction of conventional optical components for use in conjunction with the apparatuses disclosed herein, such as shutters or beam attenuators, reflecting prisms or other reflecting components, filters, light focusing components such as concentrators or condensers, collimating lenses, additional polarizers, electro-optical devices, and/or mirrors, etc. These variations are readily contemplated, and the above modifications are therefore well within the purview of one or ordinary skill, having regard for the present disclosure.

According to one aspect, a method and apparatus is provided that utilizes a fractional treatment modality with diffractive lens array optics of fractional lens array optics. Diffractive lens array optics are known in the art and have been described in Tanghetti, Lasers in Surgery and Medicine 48:646-652 (2016) hereby incorporated by reference in its entirety and summarized as follows. Diffractive lens array optics have been demonstrated on millisecond-pulsed laser systems for the treatment of acne scars and photo-damaged skin. These arrays created high fluence regions separated by a low fluence background to produce focal areas of ablative or non-ablative injury in the skin. To realize the advantages of a fractional treatment with the picosecond laser system of Tanghetti, a hand piece with a diffractive lens array was added for the treatment of acne scars and wrinkles. A 755 nm picosecond Alexandrite laser with a diffractive lens array optic was used to treat in vivo skin at three different fluence and spot size settings as shown in Table 1 of Tanghetti. The diffractive lens array consisted of closely packed individual hexagonal lenses with 500 micrometer pitch, the center-to-center lens distance. The diffractive lens array modifies the intensity profile of the Alexandrite laser beam to produce a hexagonal array of high intensity regions surrounded by low intensity background. Approximately 70% of the total energy is delivered in the high fluence regions comprising less than 10% of the treated area for a single non-overlapping pass. The remaining 30% of the energy provides the low fluence background.

According to Tanghetti, microscopic analysis was performed on three dimensional images taken immediately and 24 hours post treatment with a Vivascope 1500, Caliber Imaging and Diagnostics confocal microscope (formerly Lucid Inc., Andover, Mass.). Basic images are 500×500 µm² tiles that are stitched together to provide a larger field of view, up to 8×8 mm² at a given depth. Stitched images at different depths with 10 µm spacing were then stacked to form a three-dimensional cubic image for analysis.

Figure 7:
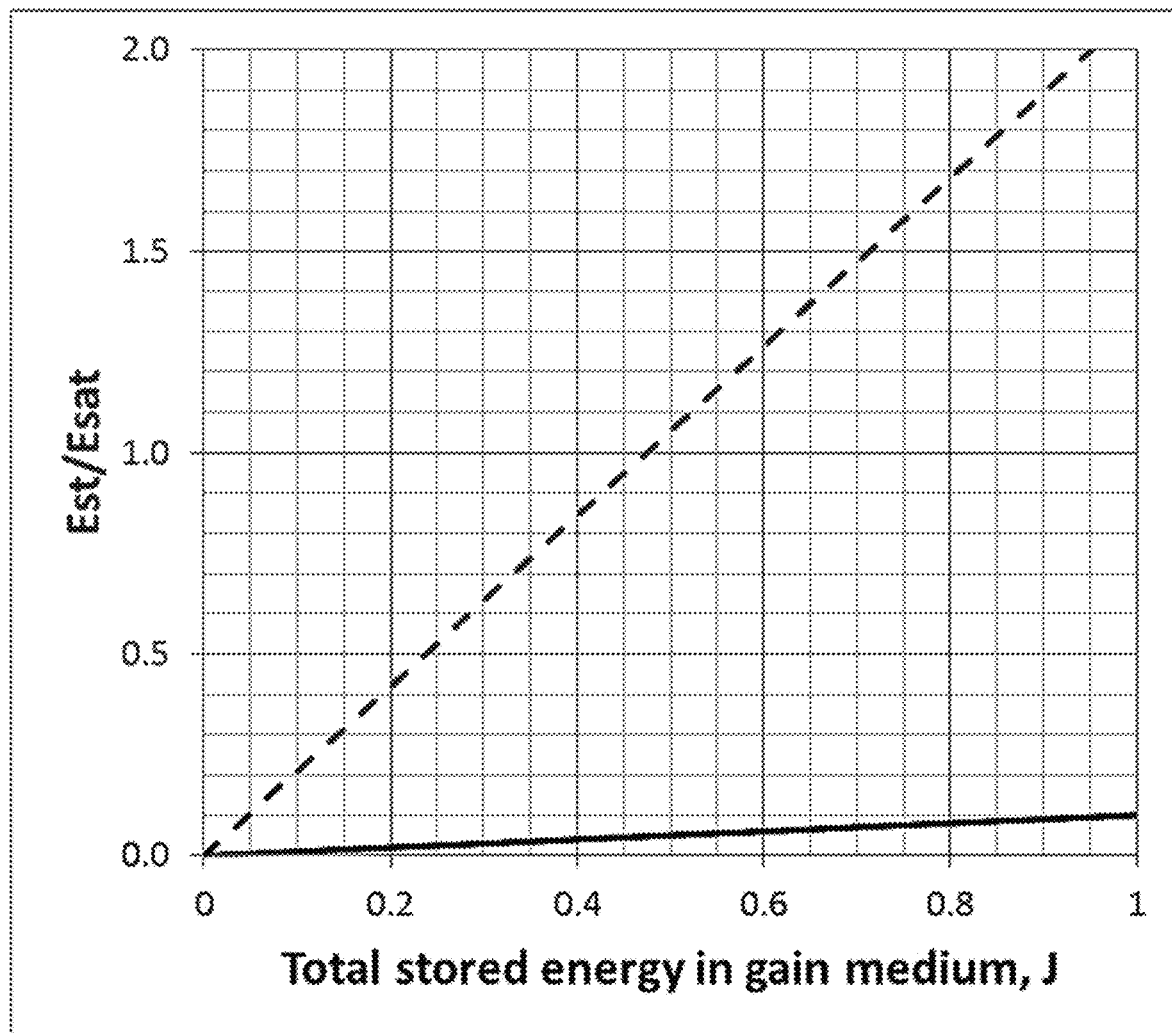
FIG. 7 shows Est/ESAT plotted as a function of the total energy stored in the gain medium. The solid line—7 mm diameter Alexandrite crystal; the dashed line—9.5 mm diameter Nd:YAG crystal.
Figure 10:
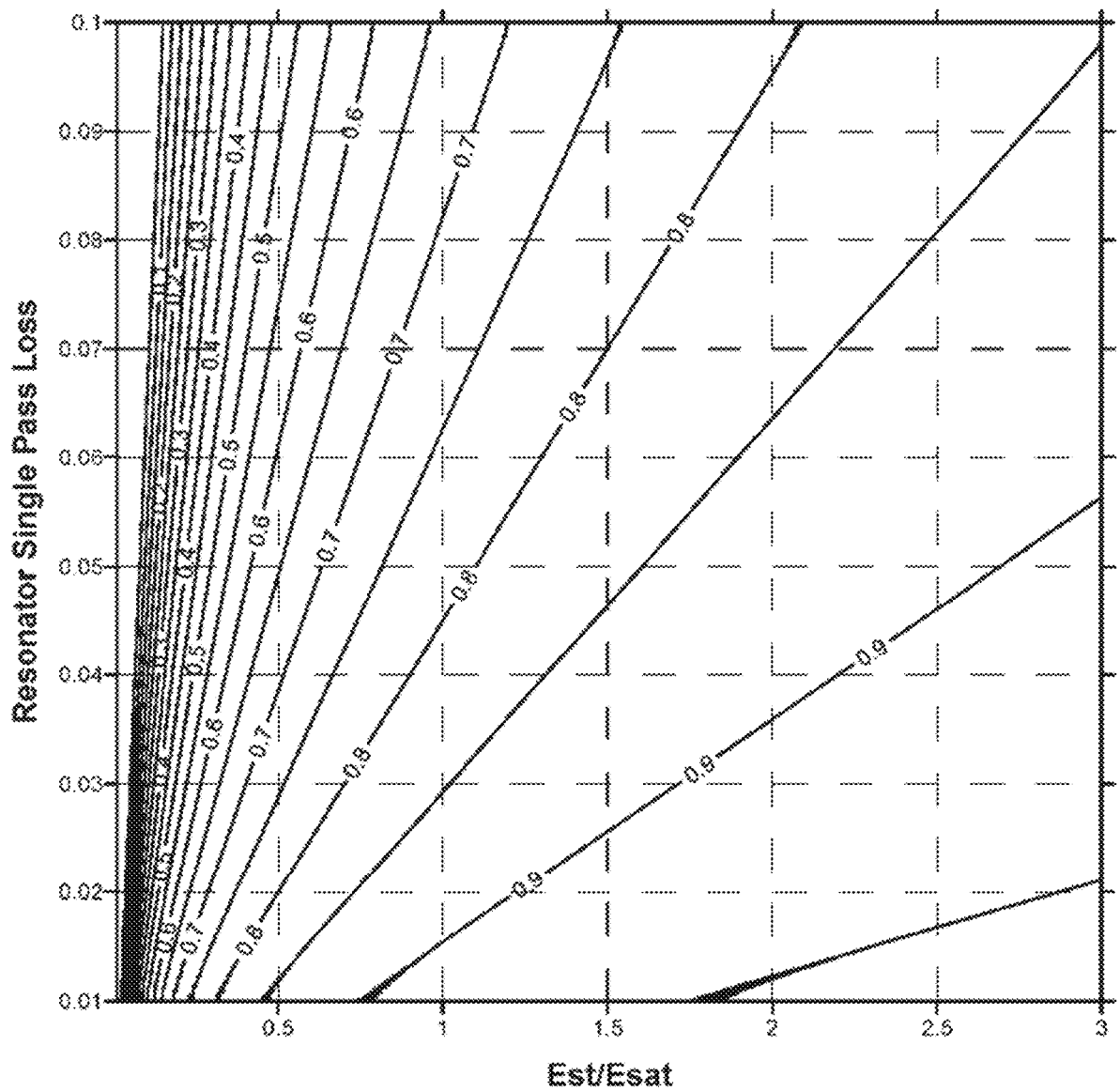
FIG. 10 shows a contour plot for the stored energy extraction efficiency Eout/Est for large gain media. The two resonator end mirrors are assumed to have reflectivity R1*R2=99%.

As described in Tanghetti, immediate post-treatment histology demonstrated well defined, approximately spherical, intra-epidermal spaces (vacuoles) void of H&E staining and measuring from 35 to 65 µm in diameter (See Tanghetti, FIG. 3). Degenerating necrotic keratinocytes were seen around the vacuoles but did not extend beyond one or two cellular layers. Location of the vacuoles varied from stratum granulosum to the dermal/epidermal junction. The vacuoles in tissue samples taken 24 hours after the treatment in darker skin types contained cellular debris positively stained with Fontana Masson, suggesting the presence of melanin (see Tanghetti, FIG. 4). Vacuoles found in lighter skin types MI<12 contained red blood cells. There was no apparent damage to surrounding cells or underlying structures found either immediately or 24 hours post treatment in any skin types. The darker skin subjects presented clinically at 24 hours and up to 3 weeks post treatment with dark spots in a hexagonal pattern at a pitch matching that of the corresponding lens array for all fluences although the intensity of the darkened dots significantly decreased with lower fluences. Mild to moderate lymphocytic perivascular inflammation was found in the papillary dermis (see Nielsen et al., J. Photochem. Photobio91. B 2008; 93:23-31 hereby incorporated by reference in its entirety. At 5 days and at 2 weeks post treatment zones of microscopic epidermal necrotic debris (MENDS) were seen immediately inferior to or within the stratum corneum (see Tanghetti FIG. 7). These zones exfoliated around 3-5 weeks post treatment. Confocal imaging immediately post treatment revealed no abnormalities in the epidermis or the papillary dermis for all subjects and treatment parameters. However, 24 hours after treatment, well-defined spherical vacuoles characterized by bright areas in the image were observed. These vacuoles ranged in diameter from 25 to 70 mm and were located between 55 and 75 mm deep within the stratum spinosum. Tanghetti FIG. 10 exhibits vacuole diameters versus treatment fluence in two darker-skinned subjects. When adjacent confocal images of the darker skinned subjects were stitched to provide a larger surface area view, a hexagonal pattern of vacuoles emerged with a pitch approximately corresponding to that of the lens array optic used for the treatment (see Tanghetti FIG. 11).

As described in Tanghetti, a 755 nm picosecond Alexandrite laser with a diffractive lens array optic delivered an array of unique, focal zones of intra-epidermal injury in the stratum spinosum characterized by vacuoles at the site of the high fluence zones. As measured with confocal microscopy and H&E staining, the stratum corneum and all tissue surrounding the vacuoles appeared normal with no indication of collateral thermal damage. This injury profile is in stark contrast to epidermal and dermal damage apparent in non-ablative and ablative fractional treatments. In a recent clinical study with a fractional picosecond Alexandrite laser, these localized epidermal vacuoles were associated with the deposition of new dermal collagen, elastic tissue, and mucin (see Brauer et al., JAMA Dermatol 2015; 151(3):278 hereby incorporated by reference in its entirety). Keratinocytes produce a number of growth factors, chemokines, and cytokines in response to injury or a wound (see Werner et al., J. Invest. Dermatol. 2007; 127(5)998-1008. These factors and agents could stimulate and regulate the response to this injury through receptors on epidermal and dermal cells. It has been speculated that the rapid vacuole formation with the generation of a laser induced breakdown (LIOB) could create a pressure fluctuation in the skin (see Vogel et al., J. Acoust. Soc. Am. 1996; 100(1):148 hereby incorporated by reference in its entirety. This could also result in the initiation of dermal remodeling from changes in cell signaling and the release of cytokines from alterations in cellular membranes (see Tanghetti et al., Lasers Surg. Med. 2015; 47(526):24 and McDaniel, Lasers Surg. Med. 2015; 47(526):22 each of which are hereby incorporated by reference in its entirety). The high fluence zones created vacuoles, but the likelihood of this depended on the fluence within the zones, that is, the diffractive lens array and the amount of pigmentation. In darker skin types with high melanin content the confocal microscopic signatures were distinctly bright, quasi-spherical regions presumably due to light scattered from cellular debris consisting of nuclei and melanosome clusters within the vacuoles. As the melanin content of the epidermis decreased, the size, location, and prevalence of the vacuoles also decreased. In lighter skin types the injury profile dramatically changed. In histology the vacuoles accompanied by hemorrhage were found at the dermal-epidermal junction. The vascular injury was only seen at the higher fluence 0.71 J/cm². The target chromophore apparently had shifted to include hemoglobin in the superficial capillary loops. These findings illustrate the importance of melanin in confining the injury to vacuoles in the epidermis and suggest a fluence threshold for vacuole formation dependent on skin pigment concentration. The role the vacuoles play in bringing about clinical outcomes is a subject of further investigation but the physical process leading to their formation is known to proceed by a complex sequence of steps. The creation of vacuoles in retina by laser heating has been reported and analyzed theoretically in the literature (Gerstman et al., Lasers Surg. Med. 1996; 18(1): 10-21.) The theory posited expansion of a steambubble created by laser heating of retinal melanin. A short laser pulse (less than microseconds) resulted in essentially instantaneous heating followed by expansion of the bubble long after the pulse had ended. In the present case, the target chromophore is the melanin in the epidermis. However, absorption of laser radiation by these granules alone is insufficient explain the observed bubble formation. A chromophore with 100 times greater absorbance is required. Such a highly absorbing chromophore can be created transiently by the laser radiation, via the LIOB process. In the LIOB process thermionic emission of one or more electrons from laser-heated melanin provides initial free "seed" electrons during the laser pulse (see Tanghetti FIG. 12A). Free electrons very efficiently absorb the laser light to gain energy between collisions with the surrounding molecules. When the energy of the seed electron exceeds that required to ionize a melanin molecule the next collision can result in the generation of a second free electron. This process repeats and the free electron density and energy grow to form an ionized plasma that continues to very efficiently absorb the remaining laser radiation of the pulse. The resulting hot plasma heats the surrounding tissue via electron-molecule collisions even after the laser pulse has ended (see Tanghetti FIG. 12C). Theoretical analysis shows that the energy of the plasma is sufficient to create a steam bubble causing the intra-epidermal vacuoles (see Tanghetti FIG. 12D) (see Mirkov et al., Lasers Surg. Med. 2016; 48(527):1.

The process for LIOB formation relies on the generation of initial seed electrons to efficiently absorb the laser radiation. The generation of these electrons by means of thermionic emission is statistical in nature. Theoretical analysis relates the probability of thermionic emission to the laser parameters and melanin concentration. The greater the laser fluence or melanin concentration, the earlier in the laser pulse a seed electron will initiate LIOB formation. This means more energy in the remaining pulse is absorbed by the electron plasma to create larger vacuoles. In light-skinned subjects the probability of LIOB formation is greatest in the deeper region of the epidermis, in proportion to the epidermal melanin concentration (see Nielsen et al., J. Photochem. Photobiol. B 2008; 93:23-31 hereby incorporated by reference in its entirety. Hemorrhagic vacuoles within the epidermis or superficial papillary dermis suggest that the LIOB process itself can either disrupt neighboring blood vessels or be initiated by hemoglobin (see Habbema et al., J. Biophotonics 2012; 5(2):194-1994 hereby incorporated by reference in its entirety.

The following examples are set forth as representative of aspects of the present disclosure. These examples are not to be construed as limiting the scope of the disclosure as other embodiments and aspects are apparent in view of the present disclosure.

Example I

Exemplary Laser Resonator

The laser device or laser resonator depicted in FIG. 1 requires building up of the Pockels cell charge. Exemplary lengths and transit times through individual components of an exemplary resonator are provided in Table 1:

TABLE 1

| Component | Laser rod | Pockels | Polarizer | Polarizer air | Air gaps | Total |
|---|---|---|---|---|---|---|
| Length, mm | 20 | 25 | 4 | 23 | 10 | 82 |
| Transit time, ps | 117 | 126 | 19 | 77 | 33 | 373 |

For a resonator employing the components listed in Table 1, the cavity transit time is 373 ps and the cavity round trip time is 746 ps. The polarizer, the Pockels cell and the M1 end mirror form a variable reflectivity output coupler. The Pockels cell allows the resonator to progress through three consecutive phases or states and generates a sub-nanosecond pulse.

Figure 2:
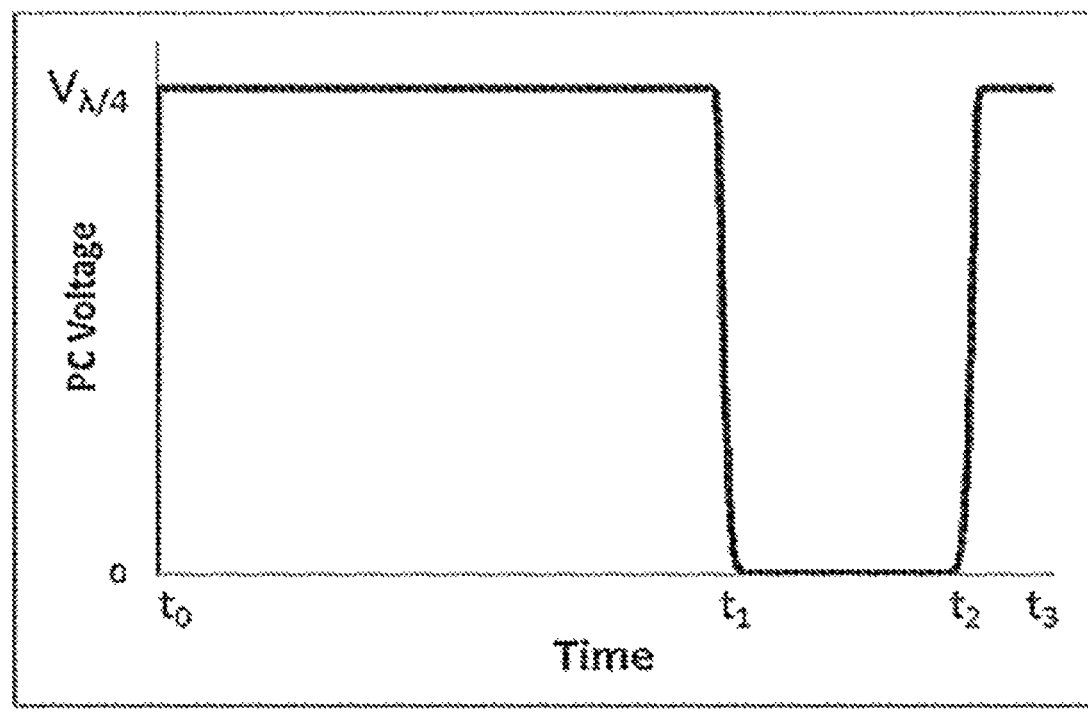
FIG. 2 illustrates the Pockels cell voltage waveform (not to scale).

The three consecutive phases or states are illustrated in FIG. 2 showing the voltage waveform applied to the Pockels cell. The processes in the laser resonator in the three consecutive states are "Hold-off", "Buildup" and "Cavity dumping" as explained below.

The Hold off state is illustrated from the $t_0$ to $t_1$ time points in FIG. 2. The quarter wave voltage applied to the Pockels cell at time $t_0$ prevents the buildup of optical field in the resonator while energy is pumped and stored in the laser gain medium. The quarter wave voltage refers to the voltage required across the Pockels cell to split the incident radiation into two components having equal intensities and retard the polarization electrical field vector of one component by one-quarter of a wavelength relative to the other component. If the polarizer 24 rejects radiation having an electric field vector that is orthogonal (or perpendicular) to the orientation of the initial electric field vector of radiation from the lasing material 26, the net effect of the combined components (first mirror 30 (or M1), Pockels cell 22, and polarizer 24) is that of a variable reflectivity mirror. The term "substantially equal to the quarter wave voltage" indicates an applied bias voltage to the electro-optical device of its quarter wave voltage or preferably at least 80% to 120%, typically at least 90% to 110%, and often at least 95% to 105% of its quarter wave voltage. Thus radiation, having been reflected at the second mirror 32 and therefore passing twice through the Pockels cell 22 with an applied voltage of $V_{\lambda/4}$, will have its polarization axis rotated 90° and will be completely rejected by polarizer 24. An applied voltage $V=V_{\lambda/4}$ therefore provides an effective reflectivity, $R_{\mathit{eff}}$, of "0%" or "substantially 0%," meaning that the radiation is either completely rejected by the polarizer 24, or possibly all but a small amount of radiation is rejected, e.g., an amount having an intensity or amplitude generally of less than about 10%, typically of less than about 5%, and often less than about 1%, of its initial intensity or amplitude, $I_0$, prior to the first pass of the radiation through the polarizer 24 and Pockels cell 22. The hold-off time from $t_0$ to $t_1$ is in the range of 0.5 to 3 storage laser level lifetimes depending on the available pump power source. A higher pump power source can be used for shorter hold off time. A lower pump power source requires a longer hold-off time. The upper limit for the hold-off time is set by a multiple of the storage level lifetime of the laser gain material.

The Buildup state is illustrated from the $t_1$ to $t_2$ time points. After storing a predetermined amount of energy in the laser gain medium, the Pockels cell is switched to 0 volts or substantially 0 volts, setting the resonator in a low-loss state. Electrically, the Pockels cell acts as a capacitor, with a typical capacitance of about 10 picofarads (pF). The term "substantially 0 volts" indicates that the electro-optical device may be completely discharged to 0 volts or that the applied voltage will generally be less than 10%, typically less than 5%, and often less than 1%, of the quarter wave voltage of the device. The two resonator end mirrors are nominally 100% reflective at the laser wavelength. In this condition, the laser energy oscillates between two totally reflective or substantially totally reflective mirrors 30 and 32 along axis 20. The relatively high gain in the laser gain medium and low resonator loss allow for buildup of the optical field inside the resonator with negligible leakage out of the resonator.

The Cavity dumping state is illustrated from the $t_2$ to $t_3$ time points. When the optical field inside the resonator builds up to its peak, the Pockels cell is switched to quarter wave voltage at time $t_2$ and kept at that voltage for about one cavity round trip time or longer, until $t_3$. That leads to extraction of the optical energy from the resonator in an optical pulse that is equal to or longer than the resonator round trip time.

The laser resonator is cycled through these three consecutive states multiple times per second to achieve a repetition rate from a few hertz to a few hundreds of hertz. The Pockels cell voltage waveform plotted in FIG. 2 has three time points with relatively large voltage transients at to, $t_1$ and $t_2$ time points. There are large differences in the requirements for the voltage transients at these three time points.

The to transient establishes the hold off voltage and the to transient can be relatively slow, for example, microseconds to a few milliseconds. The pumping of the gain medium starts after the hold off voltage is established and lasts hundreds of microseconds.

The $t_1$ transient occurs when a predetermined amount of energy is stored in the gain medium. During that transient, the gain in the resonator is the highest and the optical field builds from noise levels. Longer $t_1$ transient would allow for more energy to leak out of the resonator before the resonator reaches the low loss buildup state. For a high-gain material like Nd:YAG, it is beneficial for the $t_1$ transient to be shorter. A lower gain material like Alexandrite can work with a longer $t_1$ transient, for example, tens of nanoseconds.

The $t_2$ transient allows for the operation of the Q-switched cavity dumped laser, as it determines the cavity-dumping transient which generates a sub-nanosecond pulse output. As is known in the art, so-called "perfect dumping" occurs "suddenly" and the output pulse duration is exactly one cavity round trip time. According to the present disclosure, if the requirement for cavity dumping is relaxed from "suddenly" to on the order of the cavity round trip time, the output laser pulse duration becomes a little longer than one cavity round trip time as illustrated in FIGS. 3A-3D. For FIGS. 3A-3D illustrating the calculated voltage transients (dashed line) and output pulse shapes (solid line) from a cavity-dumped resonator, the time units are in cavity round trip time [trt]. The Pockels cell voltage transients are plotted with dashed lines, and the voltage amplitude is normalized to the quarter wave voltage for the Pockels cell $V_{\lambda/4}$. The voltage transient time $\tau_{10\text{-}90}$, is defined as the time needed for the voltage to change from 10% to 90% of the quarter wave voltage. The transient time $\tau_{10\text{-}90}$, is presented in units of cavity round trip time. The midpoint of the voltage transient, i.e., 50% of the quarter wave voltage, is set to occur on the N-th round trip for consistency of the plots. The output pulse shape is plotted with a solid line. The full width at half maximum is shown as $\tau_{pulse}$ calculated in units of cavity round trip time. In all four cases of FIGS. 3A-3D, the output pulse energy, the area under the pulse shape curve, is the same.

Figure 3A:
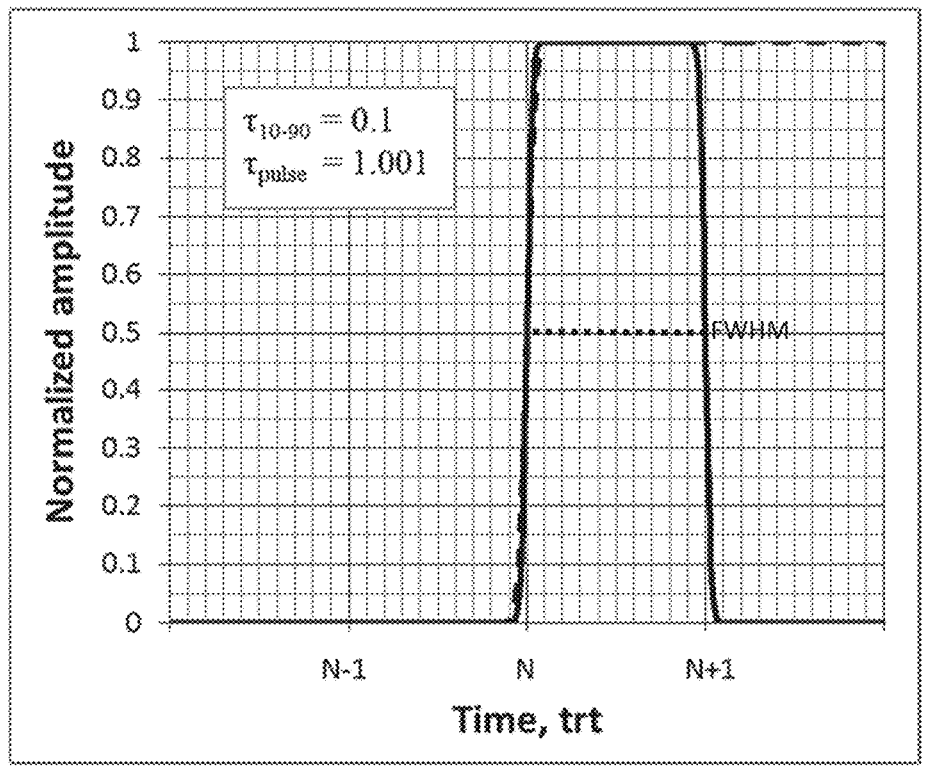
FIGS. 3($a$), 3($b$), 3($c$) and 3($d$) are time plots, where the units are in cavity round trip time [trt].
Figure 3B:
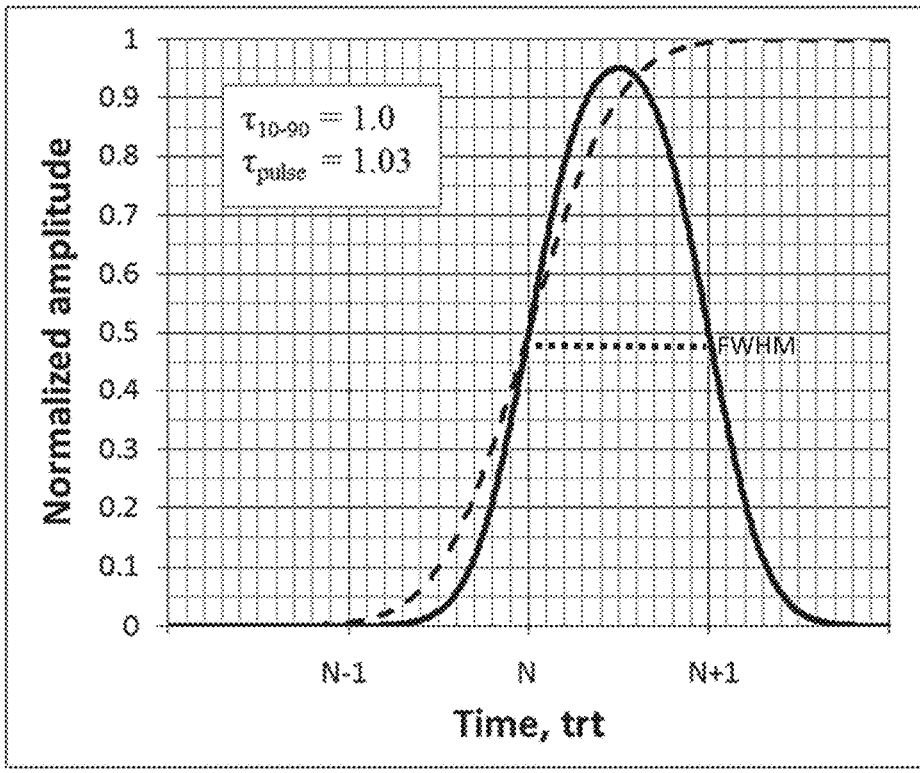
Figure 3C:
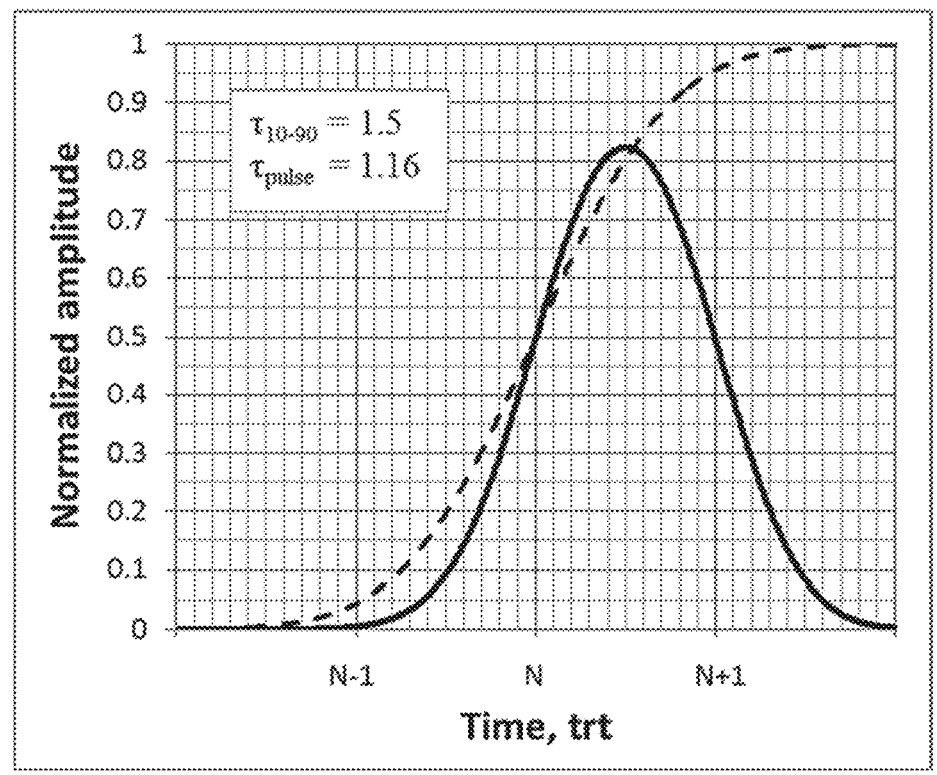
Figure 3D:
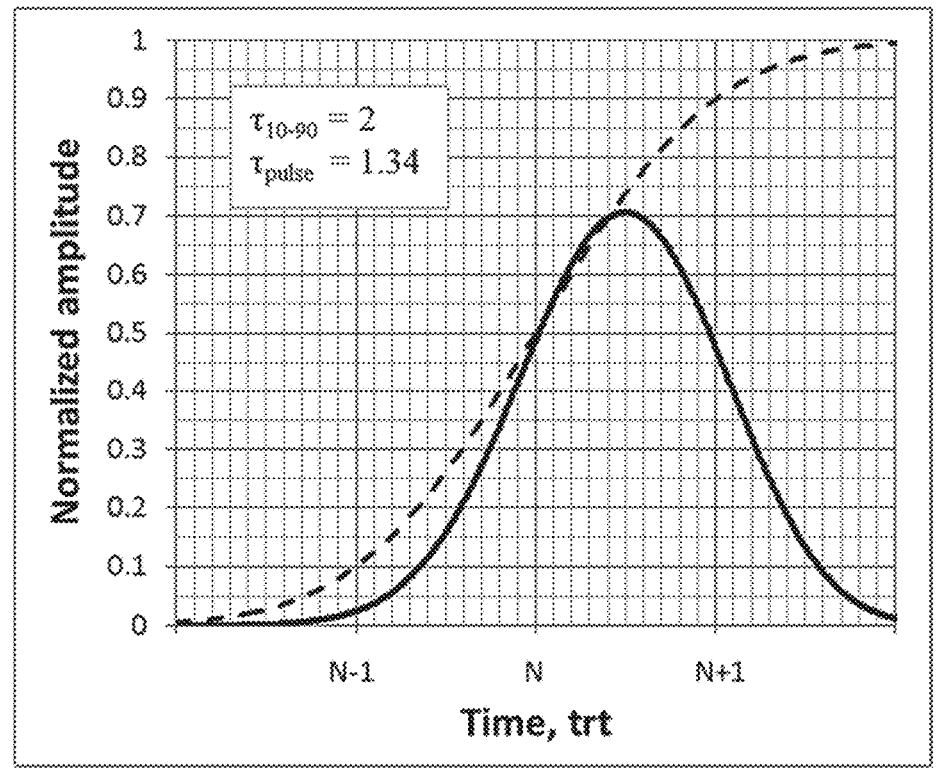

FIG. 3A is representative for the suddenly cavity-dumped resonator. The voltage transient is only 10% of the cavity round trip time and the output pulse duration is 0.1% longer than the cavity round trip time. FIGS. 3B-3D are representative for the much more practical voltage transients that are of the order of the cavity round trip time and the corresponding output pulse durations that are from 3 to 34% longer than the cavity round trip time. For example, for a resonator with a 750 picosecond cavity round time, FIG. 3B shows output pulse duration around a 772 picosecond pulse and is desirable. FIG. 3C is on the order of acceptable, but is closer to the high end of the desired output of the specification range, e.g., about 900 picoseconds.

Figure 4A:
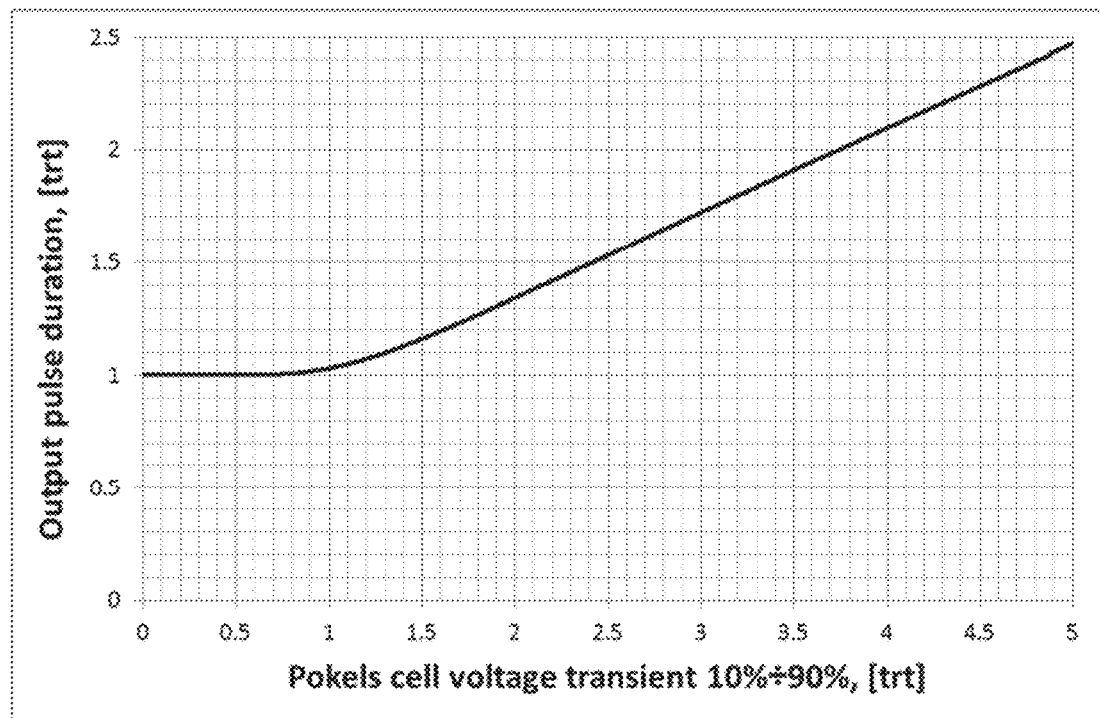
FIG. 4($a$) illustrates output pulse duration as a function of the Pockels cell voltage transient. Transient times and output pulse durations are in units of cavity round trip times.
FIG. 4(g) shows a contour plot for the calculated energy extraction efficiency. In the region enclosed between the two 99% contour lines, practically all the circulating resonator energy is extracted.
Figure 4B:
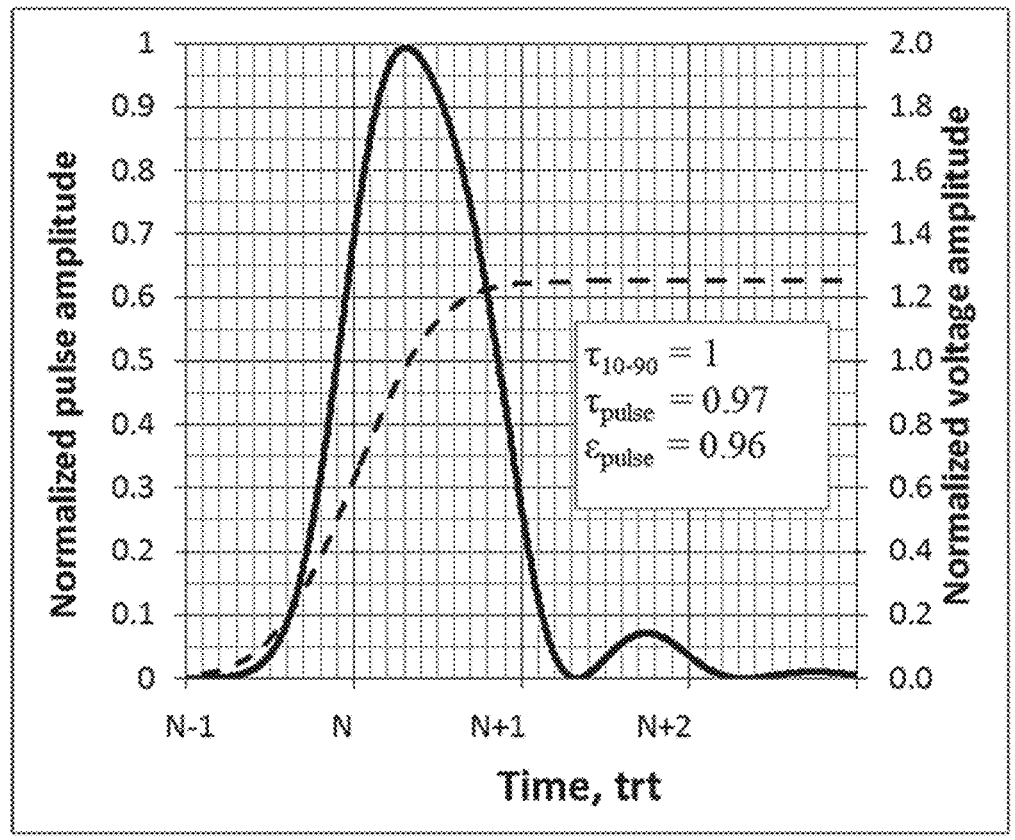
Figure 4C:
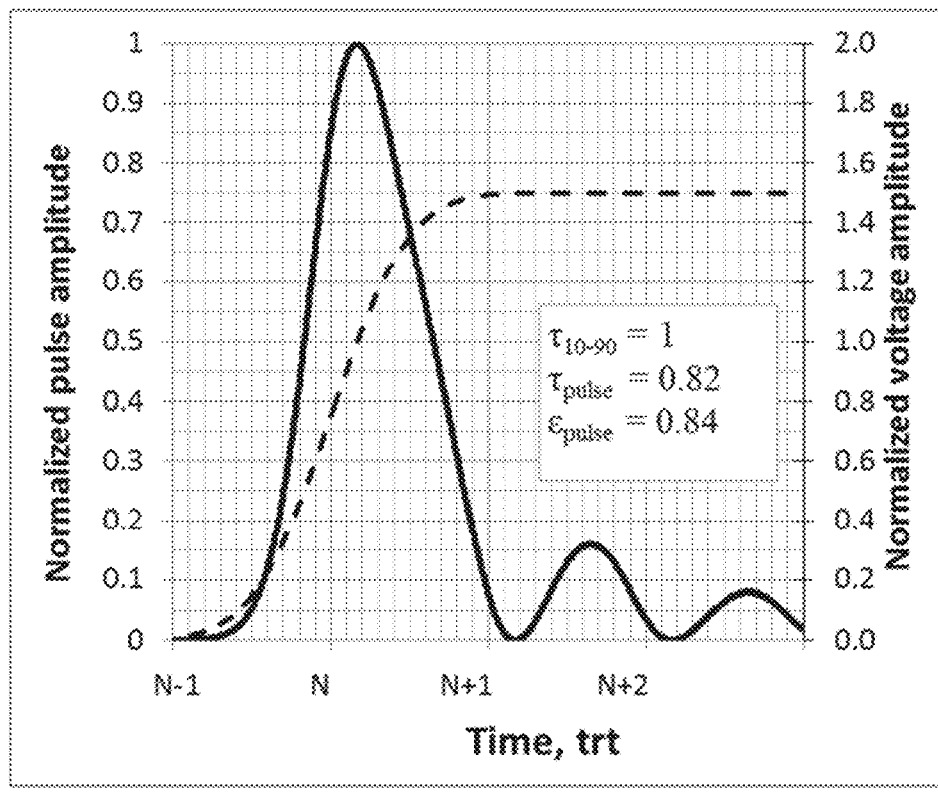
Figure 4D:
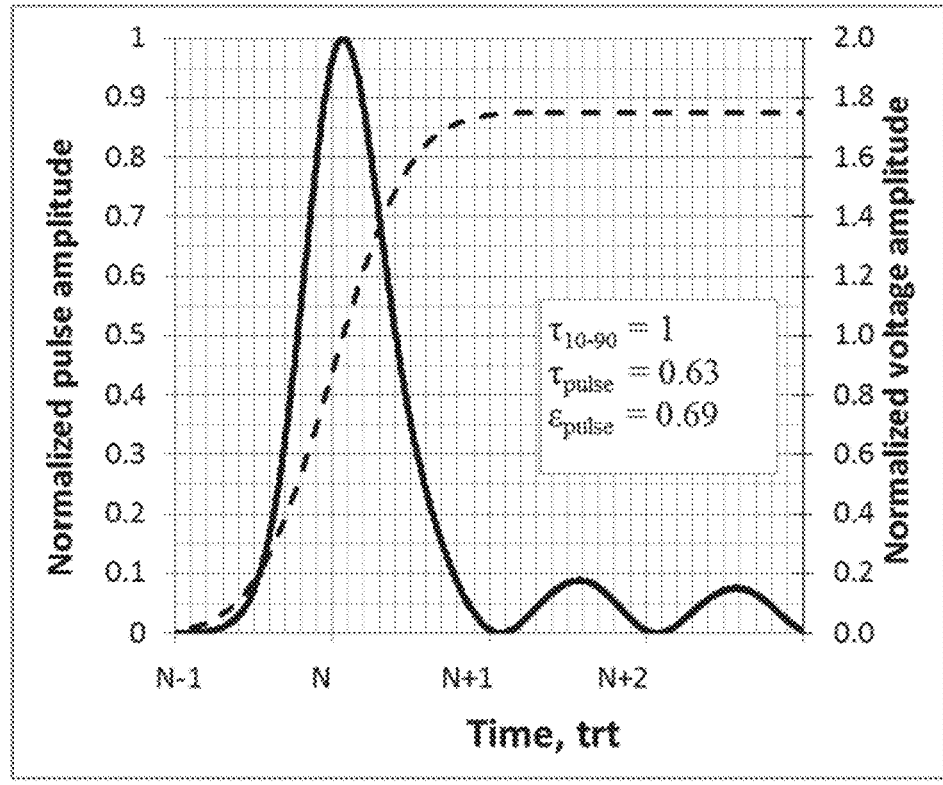

The calculated output pulse durations for a range of voltage transients are plotted on FIG. 4A in units of cavity round trip time [trt]. FIG. 4A summarizes the effect of realistic Pockels cell voltage transients on the cavity-dumped output pulse duration. As an example, using the example laser resonator depicted in FIG. 1 and with components in Table 1 with a round trip time of 746 ps, if the Pockels cell voltage transient is 746 ps, equal to the cavity round trip time, then the calculated output pulse duration is 1.03 round trip times, which is 768 ps. That is the desired sub-nanosecond output pulse duration for the example resonator with realistic Pockels cell voltage transient. Accordingly, an exemplary output pulse is from 700 ps to 800 ps. According to one aspect, sub-nanosecond voltage transient technology in a Pockels cell known to those of skill in the art is useful in the present disclosure. For example, Bishop, A. I. and P. F. Barker "Subnanosecond Pockels cell switching using avalanche transistors." Review of scientific instruments 77.4 (2006): 044701 hereby incorporated by reference in its entirety discloses methods of pulse shaping and pulse termination using subnanosecond Pockels cell switching using avalanche transistors.

According to one aspect, the Pockels cell voltage transients from 0 to quarter wave voltage (or QW to 0), allow for complete extraction of the energy circulating in the resonator and lead to output pulse durations similar to the resonator round trip time and longer as plotted in FIG. 4A. According to one aspect, output pulses can be generated with duration shorter than the resonator round trip time by applying to the Pockels cell voltage transients larger than the quarter wave voltage and leaving some of the circulating energy in the resonator. Examples of such voltage transients larger than the quarter wave voltage and the generated output pulse shapes are plotted in FIGS. 4B-4E. In all of these plots, the pulse shape is plotted with a solid line using the y-axis on the left, and the voltage transient is plotted with a dashed line using the y-axis on the right. The voltage transients are normalized with respect to the quarter wave voltage. In all plots, the voltage transient time $\tau_{10\text{-}90}$ and the full width at half maximum of the output pulse $\tau_{pulse}$ are calculated in units of cavity round trip time. The output energy pulse fraction $\varepsilon_{pulse}$ is calculated taking into account only the first pulse and ignoring the lower energy post pulses.

Figure 4E:
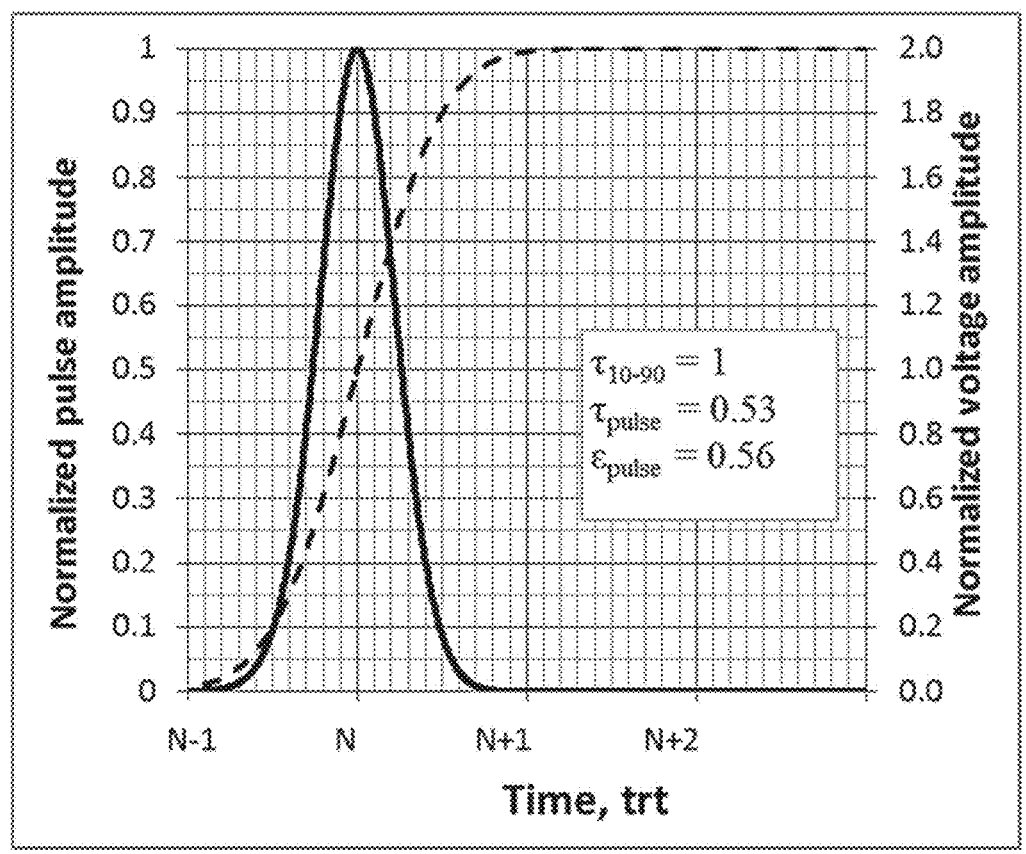

FIG. 4E shows a clean output pulse with no post pulses and with pulse duration about half of the resonator round trip time, carrying 56% of the available circulating resonator energy. The absence of post pulses is due to the fact that when the voltage applied to the Pockels cell, as depicted in FIG. 1, reaches the level of two-times the quarter wave voltage (i.e., it is equal to the half wave voltage), there is no energy extraction from the resonator.

Figure 4F:
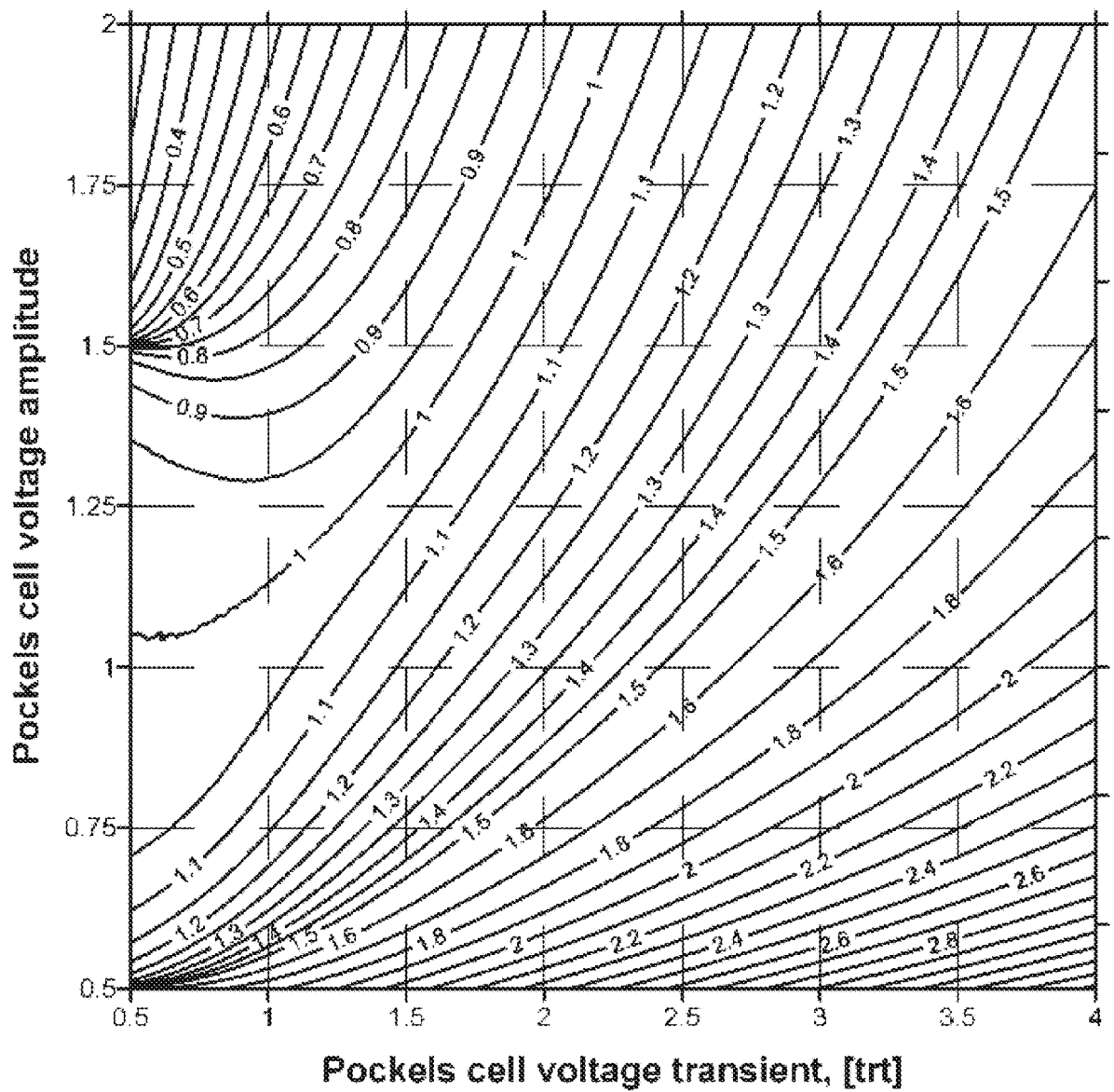
Figure 4G:
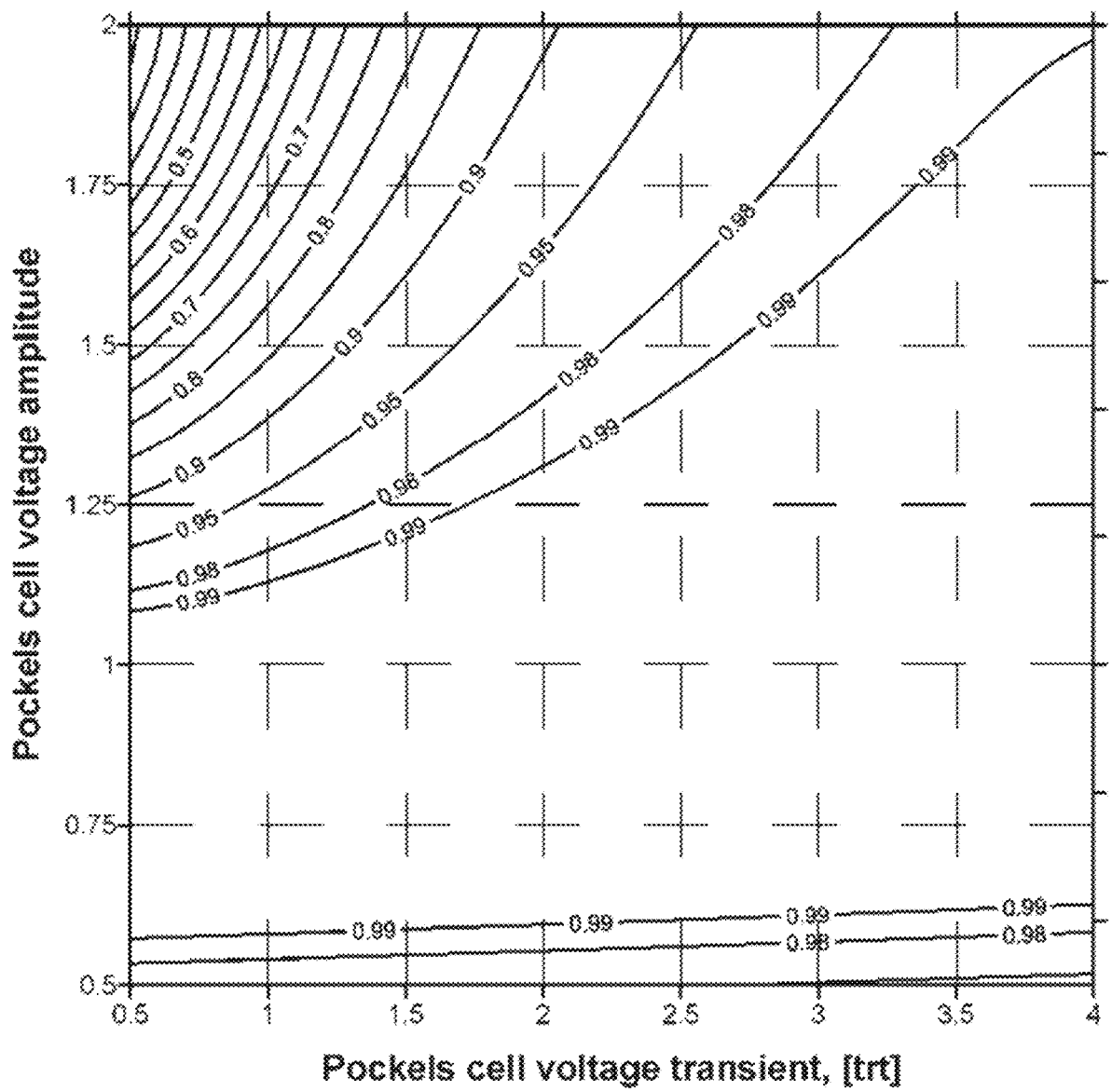

FIG. 4F is a contour plot for the calculated output pulse duration in units of cavity round trip times for a range of Pockels cell transient times and voltage amplitudes.

The Pockels cell voltage transient from zero to quarter wave voltage needed for cavity dumping shown at time $t_2$ in FIG. 2 is generally more difficult for electronics design than the transient from quarter wave voltage to zero. According to one aspect, an alternate resonator can be designed by adding a quarter wave plate 33 (Q) as shown in FIG. 5 that will lead to the alternate Pockels cell voltage waveform as shown in FIG. 6.

Figure 5:
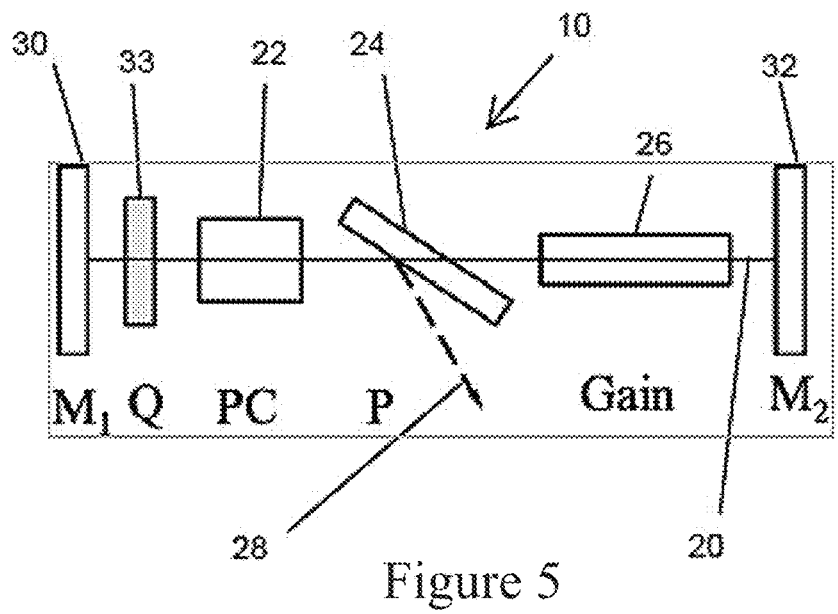
FIG. 5 illustrates an alternative resonator layout, wherein the cavity dumped pulse is extracted along the dashed arrow.
Figure 6:
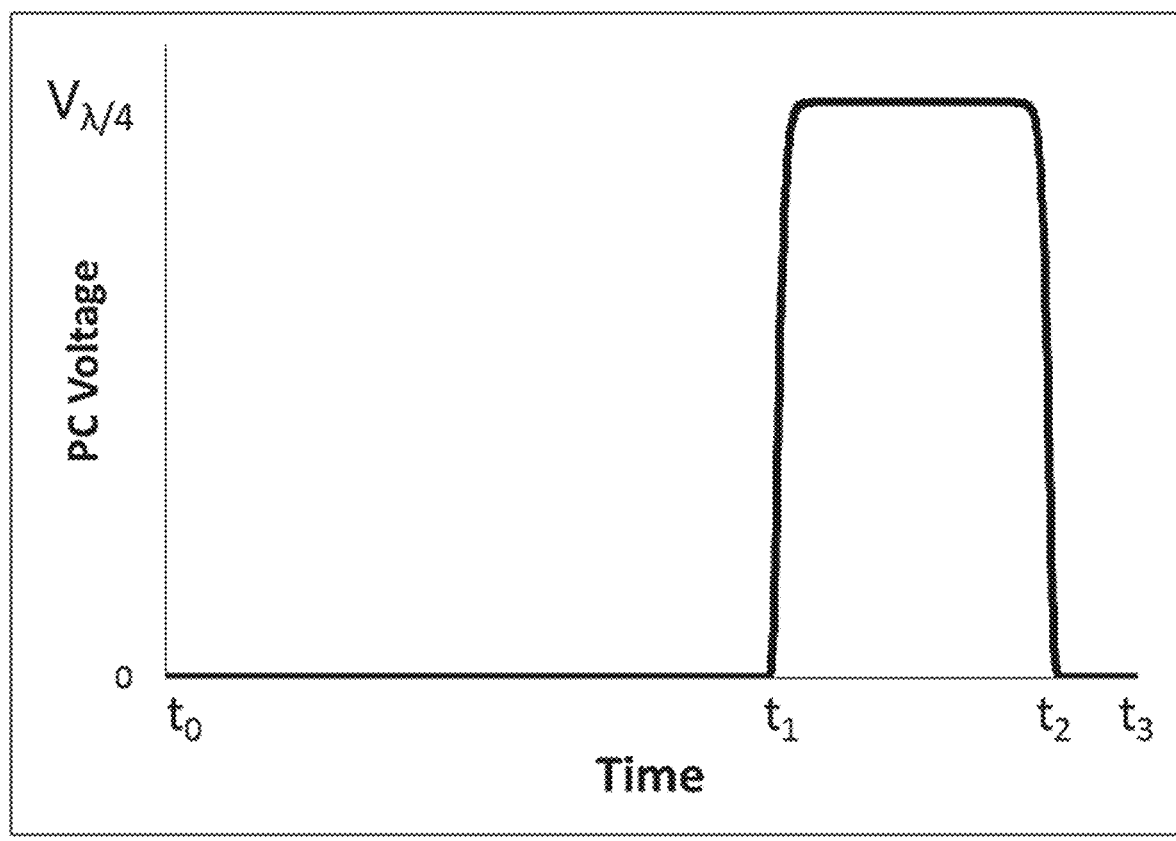
FIG. 6 illustrates an alternative Pockels cell voltage waveform (not to scale).

The embodiment of FIG. 5 enables the Pockels cell to be discharged in a manner that is relatively simple from an electrical standpoint. The arrangement of components depicted in FIG. 5 may employ a high gain material, for example, Nd:YAG. The electronics benefits of the alternative resonator layout and Pockels cell voltage waveform, as depicted in FIG. 5 and FIG. 6, are balanced against the drawbacks of the extra added component in the resonator, i.e. the quarter wave plate. The extra resonator component makes the resonator round trip time longer and therefore the output pulse duration gets longer for a fixed Pockels cell voltage transient time. In addition, the quarter wave plate adds two extra coated surfaces in the resonator with very low, but not exactly 0% reflectivity. Small resonator losses have a large effect on the output energy from the Q-switched cavity dumped laser, especially for low gain laser media like Alexandrite.

Example II

Exemplary Laser Energy Output

The output energy from the Q-switched cavity dumped resonator can be calculated following the standard actively Q-switched laser formalism as described in Degnan IEEE Journal of Quantum Electronics v. 25 p. 214 hereby incorporated by reference in its entirety. The main difference from the pure Q-switched formalism is that for the cavity-dumped mode of operation, the energy is extracted from the cavity when the intra-cavity energy density reaches its peak. In a practical design, it is not always necessary to detect the peak of the intra-cavity energy density to trigger the cavity dump transient at time $t_2$. For example, it is possible to optimize the time delay $t_2-t_1$ for maximum cavity dumped pulse energy at $t_2$.

Alternatively, it is possible to monitor the rate of change of the intra-cavity energy density by monitoring the parasitic reflection from the polarizer or leakage from one of the end mirrors. Then the cavity dump transient will be triggered at time $t_2$ when the rate of change of the intra cavity energy density approaches zero.

The laser operation starts with pump energy delivery and storage in the gain medium during the hold-off period from $t_0$ to $t_1$. The pump energy source may consist of flash lamps, LEDs, or another laser. Specifically, a semiconductor laser may be matched to absorption bands in the gain material and provide for higher than 90% pump power absorption in a gain material of relatively short length, for example 10 to 40 mm. The gain material may also have a dichroic coating as previously discussed. The semiconductor pump laser may consist of arrays of emitters. The individual emitters may be edge emitters or vertical cavity surface emitting lasers (VCSEL).

The performance of a Q-switched cavity dumped resonator is dependent on the stimulated emission cross section of the laser material $\sigma$. A material parameter called saturation fluence $E_{SAT}$ can be defined for any laser gain material:

$$E_{SAT} = \frac{h\nu}{\sigma}$$

where hν is the photon energy for the lasing wavelength. At the end of the hold-off period, from $t_0$ to $t_1$, the energy stored per unit area in the gain material is Est. The ratio of the stored energy per unit area and the saturation fluence is a convenient parameter describing the initial condition for the laser Buildup state, from $t_1$ to $t_2$. An example for the range of values of the dimensionless small signal gain parameter Est/$E_{SAT}$ is plotted in FIG. 7 for an Alexandrite and a Nd:YAG crystal.

The difference by more than 10× for Est/$E_{SAT}$ for equal stored energy is mainly due to the large difference in the saturation fluence for the two materials, 26 J/cm$^2$ for Alexandrite and 0.67 J/cm$^2$ for Nd:YAG. After the energy is stored in the gain medium, it is extracted during the Buildup stage, from $t_1$ to $t_2$, and then cavity dumped out of the resonator, from $t_2$ to $t_3$. The energy extraction efficiency is plotted in FIG. 8 for the range of Est/$E_{SAT}$ typical for small stimulated emission cross section, large $E_{SAT}$ material and a range of resonator single pass loss.

Figure 8:
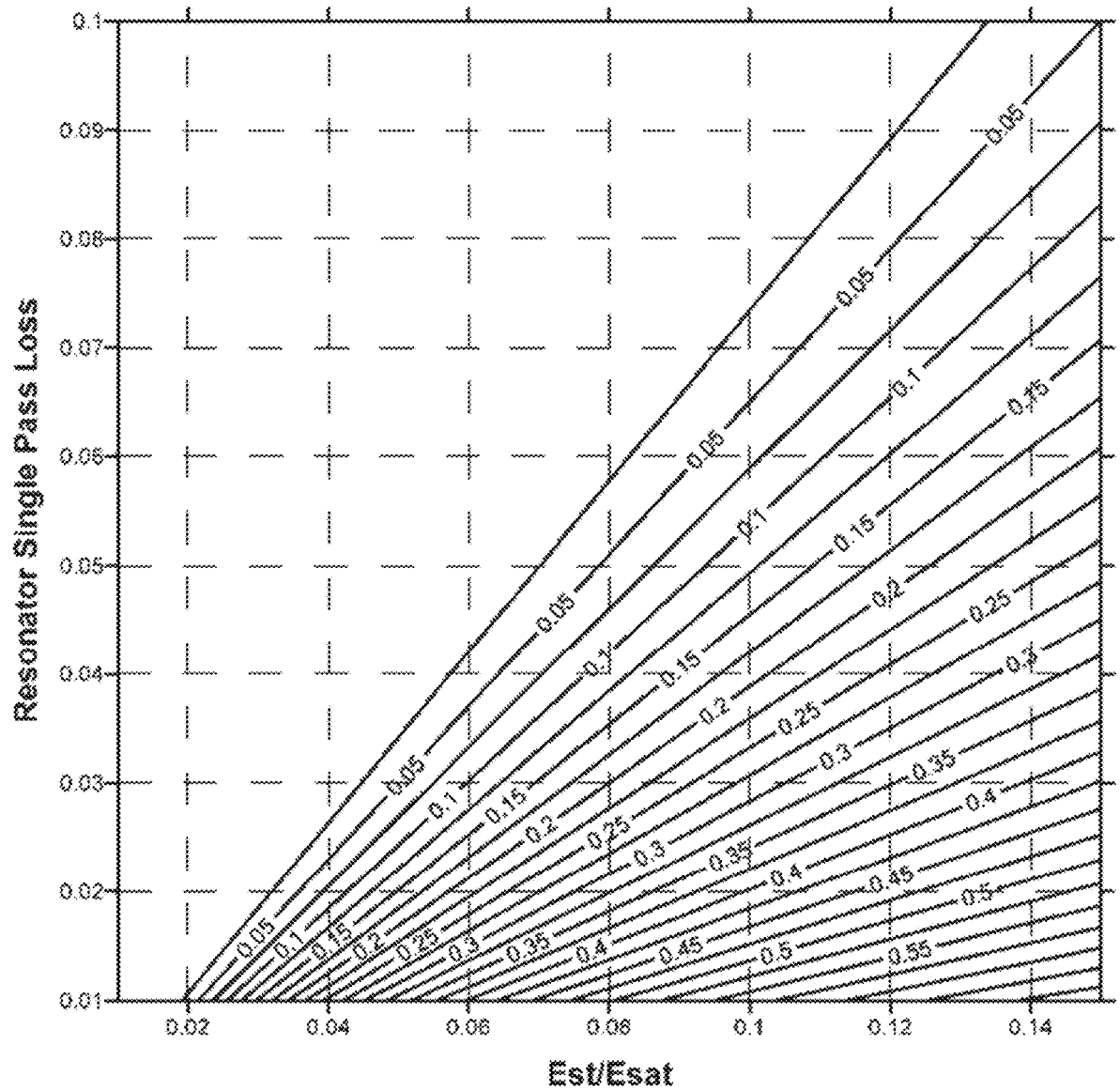
FIG. 8 shows a contour plot for the stored energy extraction efficiency Eout/Est for low gain materials. The two resonator end mirrors are assumed to have reflectivity R1*R2=99%.

FIG. 8 depicts use of low-gain materials (e.g., Alexandrite) and demonstrates the importance of keeping single pass resonator loss as small as possible, especially for low-gain material like Alexandrite. For 5% single-pass loss and the plotted range of Est/$E_{SAT}$, the maximum energy conversion efficiency is around 25%. Alternatively, for 3% single-pass loss, the conversion efficiency can be up to 40%. The large sensitivity to single-pass resonator loss is due to the relatively large number of round trips during the Buildup phase. The calculated number of Buildup round trips is plotted in FIG. 9.

Figure 9:
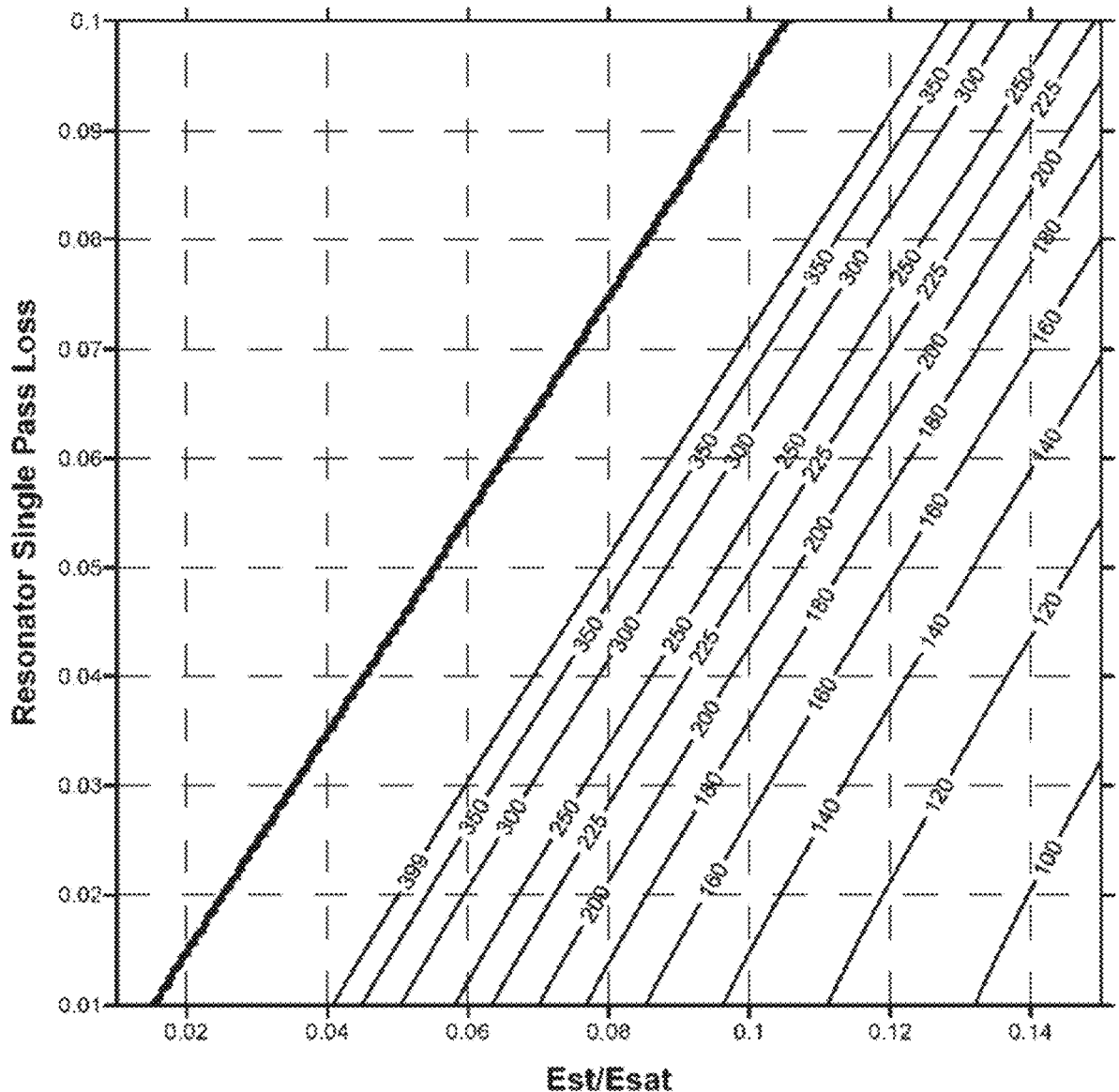
FIG. 9 shows a contour plot for the calculated number of round trips in the Buildup phase. The two resonator end mirrors are assumed to have reflectivity R1*R2=99%.

The consistent trend for FIG. 8 and FIG. 9 is that larger Est/$E_{SAT}$ and smaller single-pass loss lead to smaller number of Buildup round trips and more efficient extraction of the stored energy. The energy extraction efficiency for the Q-switched cavity dumped resonator improves for gain media with larger stimulated emission cross section, and smaller $E_{SAT}$, as plotted in FIG. 10. On the other hand, gain media with larger stimulated emission cross section present more difficulty with parasitic amplified spontaneous emission and preleasing during hold off.

A Q-switched cavity dumped resonator using the Alexandrite gain medium can be stimulated by diode pumping and can have a relatively low stimulated emission cross section and relatively short storage level lifetime. The calculated small signal gain, Est/$E_{SAT}$, in the Alexandrite rod achieved at the end of the Hold off phase is plotted in FIG. 11.

Figure 11:
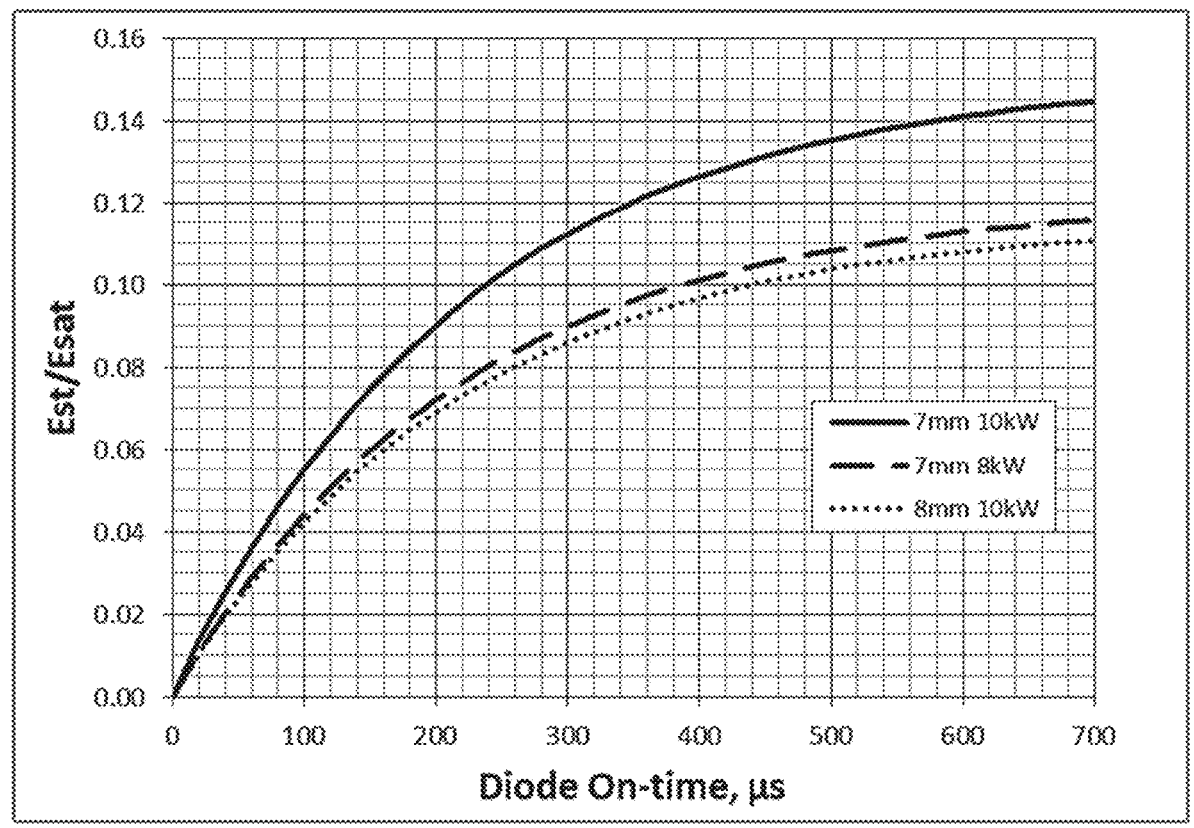
FIG. 11 shows small signal gain as a function of the pumping diode; On-time Optical efficiency 80%; Quantum efficiency 650/750; Lines labeled with Alexandrite rod diameter and pumping diode peak power.

The data plotted in FIG. 11 shows what is required to build up a resonator with Alexandrite. FIG. 11 depicts data using a 7 mm diameter Alexandrite rod versus an 8 mm rod diameter. For equal pumping power, the gain in a 7 mm rod is about 24% larger than the gain in an 8 mm rod. That increased gain has to be balanced versus the 24% smaller area of the 7 mm rod and potentially 24% higher loading of the optical coatings on the rod.

FIG. 11 also illustrates that for the Alexandrite crystal with storage level lifetime between 200 µs and 260 µs there is very little added benefit in pumping on-times beyond 600 µs (2 to 3 lifetimes). The storage level lifetime and the stimulated emission cross-section of Alexandrite are temperature dependent. The temperature dependence for these two parameters can be approximated by polynomials between 30° C. and 60° C. based on published data in Shand et al., IEEE Journal of Quantum Electronics v. 19 p. 480 hereby incorporated by reference in its entirety. The temperature set point of the Q-switched cavity dumped resonator can be optimized for maximum energy extraction. The output energy as a function of single pass loss and temperature, for fixed diode pump power and on-time, is plotted in FIG. 12.

Figure 12:
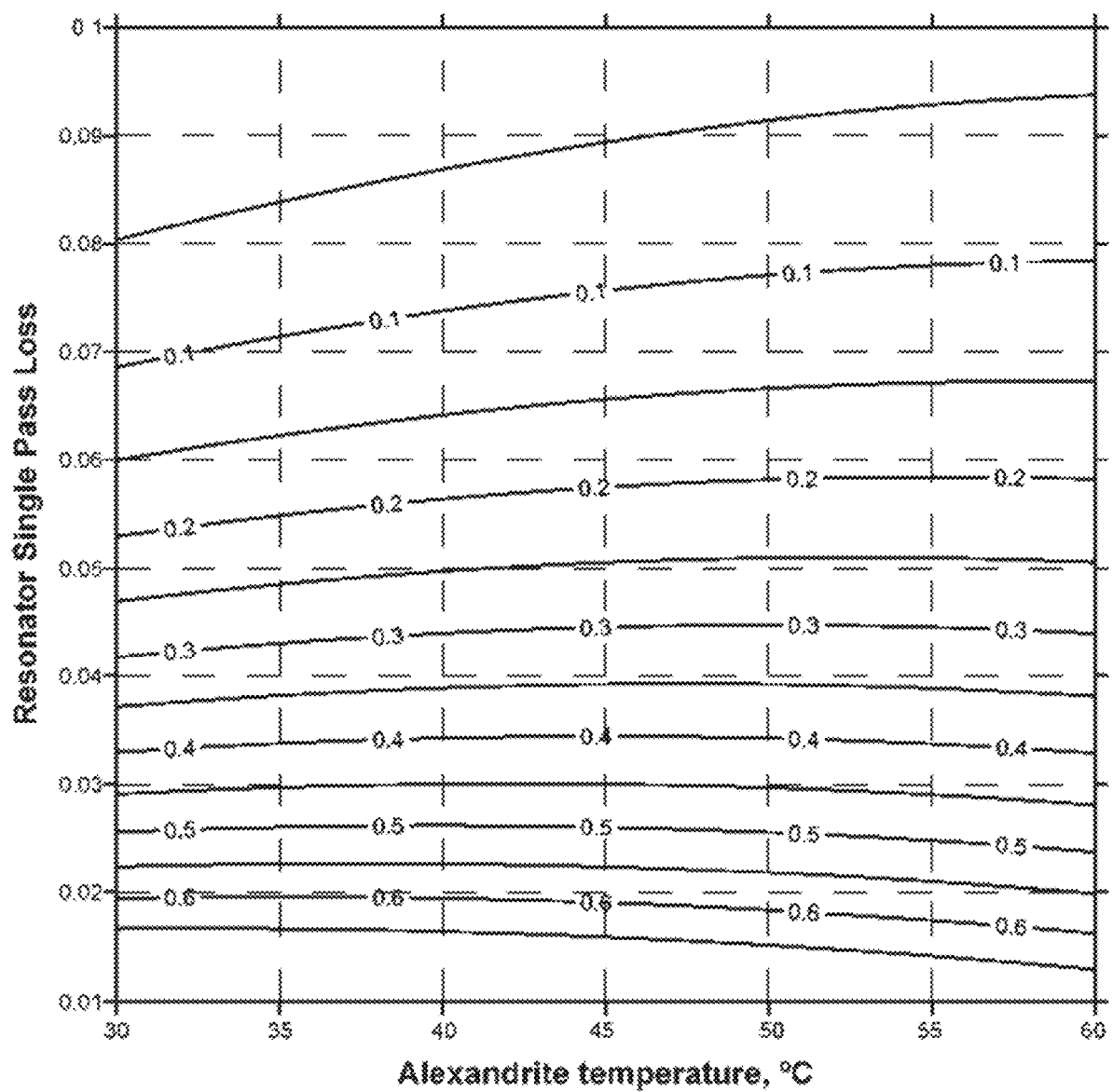
FIG. 12 shows a contour plot for output energy [J/pulse] from a Q-switched cavity dumped Alexandrite laser; Optical efficiency 80%; Quantum efficiency 650/750; 7 mm Alexandrite rod diameter; 10 kW pump diode peak power; 600 µs pump diode on-time. The two resonator end mirrors are assumed to have reflectivity R1*R2=99%.

The temperature dependence in the FIG. 12 plot indicates that under the considered pumping conditions and resulting small signal gain, the optimum Alexandrite temperature for maximum energy output shifts from around 50° C. for 5% single-pass loss to around 35° C. for 2% single-pass loss. More importantly, the temperature dependence for optimal energy output is a relatively slowly varying function. That means the Q-switched cavity dumped Alexandrite resonator temperature control can be built to maintain the temperature to within ±3° C. to ±5° C. and keep the output energy stable to within ±10%.

Example III

Exemplary Pump Sources

According to certain aspects, several different light sources can be considered for pumping the gain medium. For the two gain media used as examples herein (Nd:YAG and Alexandrite), flash lamp pumping can produce the stored energy required to produce greater than 200 mJ of laser output. According to one aspect, the flash lamp and the gain medium are housed in a traditional close-coupled, cooled, reflective pump chamber in which light from the flash lamp pumps the gain medium from the side. According to one aspect, the flash lamp provides a spectral output that overlaps with the absorption bands of the gain medium. A power supply drives the flash lamp and a cooling system removes heat generated by the system. Narrow-bandwidth pump sources (e.g., LEDs and diode lasers) can be used to efficiently pump both Nd:YAG and Alexandrite. While LEDs have been used to pump Nd:YAG and can be used to pump Alexandrite, low LED peak power requires a sufficient number of emitters to generate greater than 200 mJ of laser output. Diode lasers are a well-established pump source for Nd:YAG. Numerous geometries and pump source configurations have been used to produce efficient, high-power diode-pumped lasers.

Figure 13:
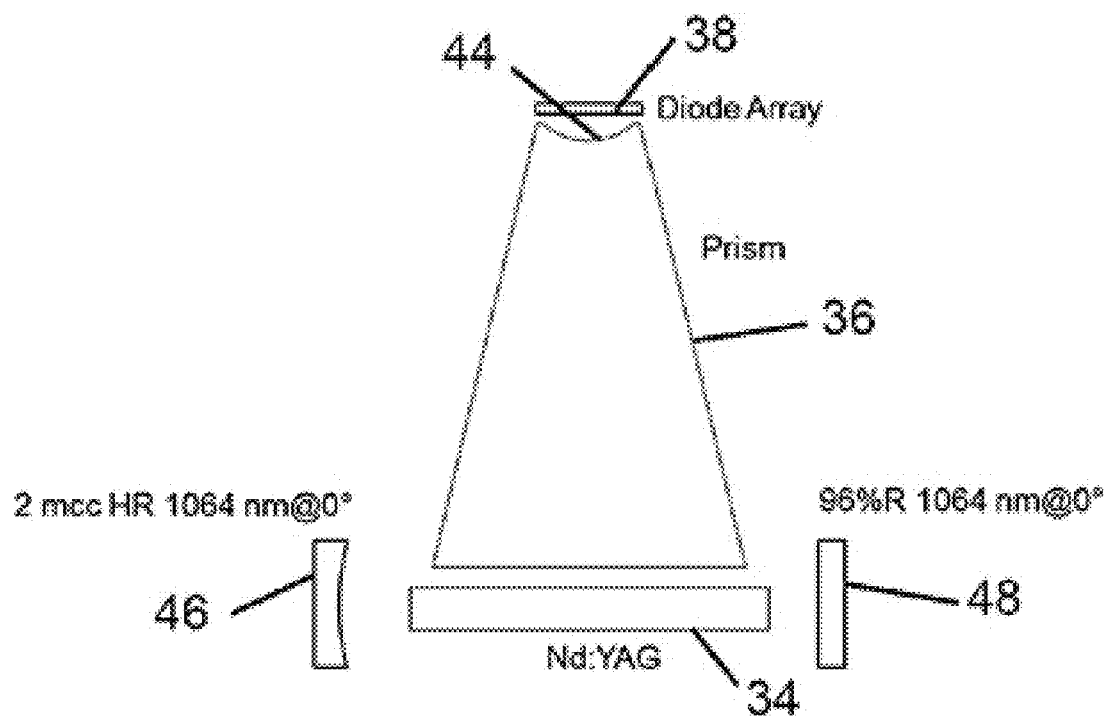
FIG. 13 illustrates a side-pumped Nd:YAG laser.
Figure 14:
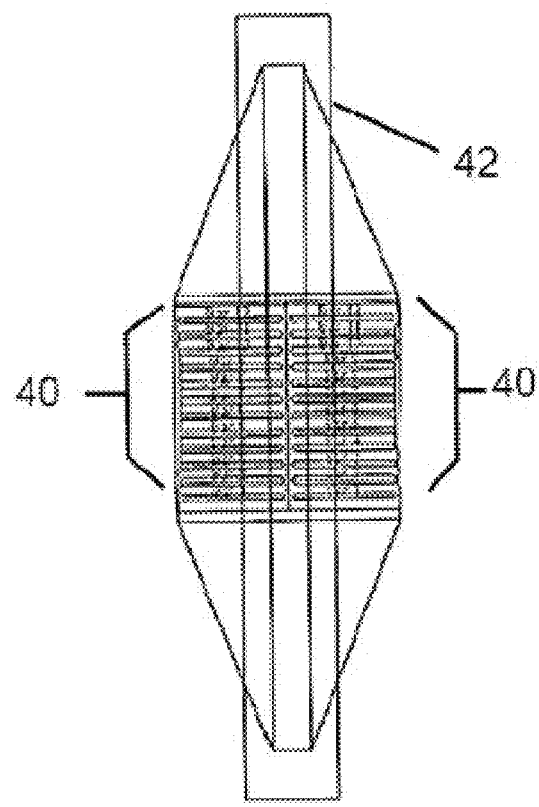
FIG. 14 shows the end view of side-pumped Nd:YAG laser.

A diode laser array suitable for use as a pump source was created using a 24-bar diode laser array emitting at 820 nm that generates 10 kW peak power in a 500 µs pulse at 10 Hz. The array includes two 12-bar, water-cooled stacks side by side. Two gold mirrors with slots for the bars were used to retro-reflect a portion of the light escaping from the pump chamber. Such an exemplary pump source is illustrated in FIG. 13. As illustrated in FIG. 13, a side-pumped Nd:YAG laser pumped by the 10 kW array was built to assess the suitability of this design for use in a Q-switched cavity dumped sub-nanosecond laser. The pump chamber consisted of a 9.5 mm diameter×80 mm long Nd:YAG rod 34 in a water-cooled flow tube inside a 3 cm diameter diffuse reflecting pump chamber (not shown) with a rectangular hole to accommodate the optical element 36 output used to couple light from the diode array 38 into the chamber. In one embodiment, the optical element 36 is a prism. Alternatively, the optical element 36 may be a lens or multiple lenses. The two 12-bar stacks 40 were placed at the 23×23 mm$^2$ NBK7 glass prism 36 input 42 as shown in the end view in FIG. 14.

The concave curve 44 in the prism expanded the fast-axis light emitted by the array such that, together with slow-axis compression, the 4×70 mm$^2$ prism output was filled. The entire Nd:YAG rod length between mirrors 46 and 48 was uniformly pumped to avoid areas of high pump density that could result in parasitic lasing during the "Hold off" state (see FIG. 2). While further beam compression is desirable to decrease the amount of pump light escaping the pump chamber, prism losses due to the low brightness of the slow-axis diode light guide against further reduction in beam width. According to certain aspects, numerous other optical systems (e.g., parabolic concentrators, various combinations of cylindrical and spherical lenses, etc.) can be used to couple light from the array to the pump chamber.

Figure 15:
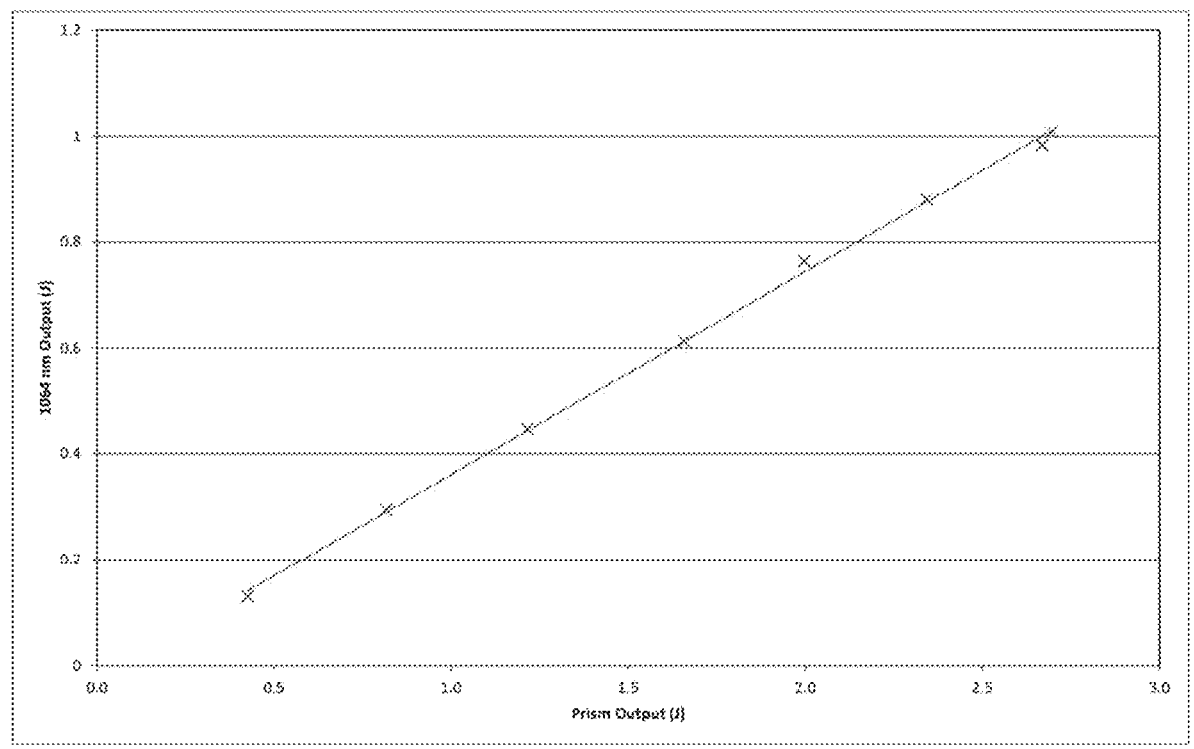
FIG. 15 shows a side-pumped Nd:YAG laser with long-pulse performance.

To assess the efficiency of the pump chamber, the multimode laser cavity shown in FIG. 13 was run in long-pulse mode with the array operated at 500 µs pulsewidth at a repetition rate of 10 Hz. The laser performance is shown in FIG. 15 where a maximum energy of 1 J was generated for 2.7 J of pump light (measured at the prism output). Taking into account the 85% prism transmission, the overall optical to optical efficiency is 31%. Given the typical 50% diode array electrical to optical efficiency, the overall efficiency (1064 nm laser output/electrical input to the array) is 16%, which is significantly higher than the about 6% efficiency observed in a typical flash lamp-pumped Nd:YAG laser.

Figure 16:
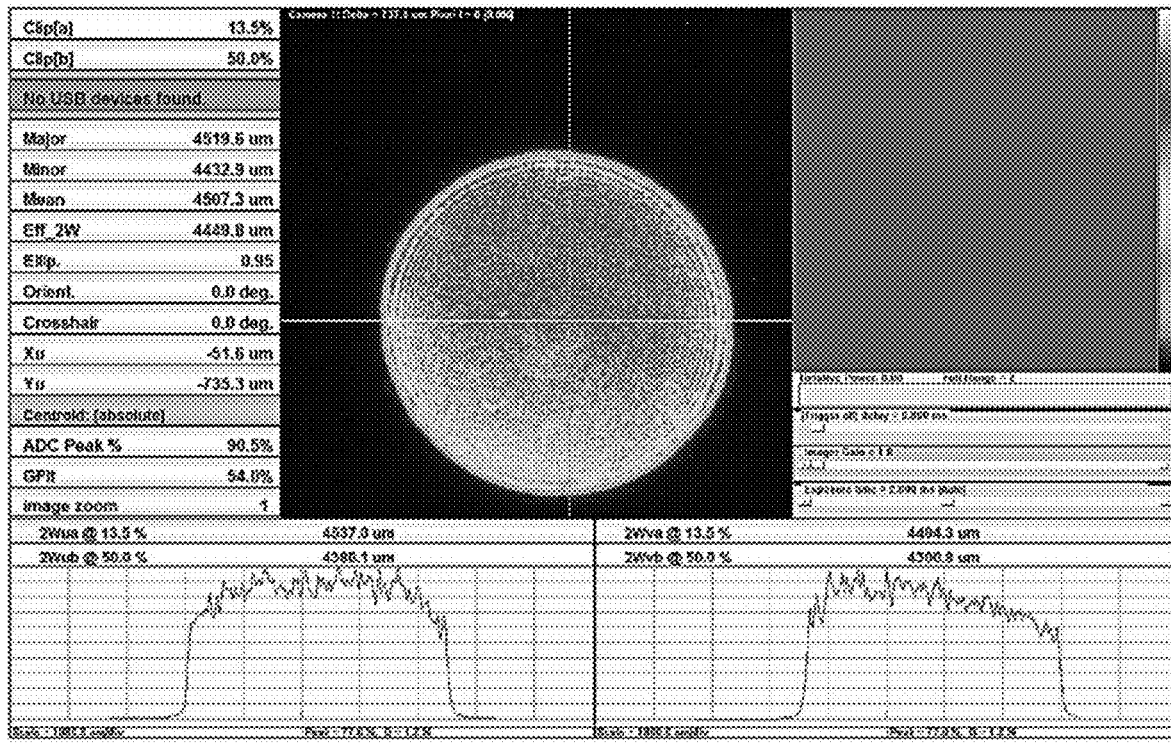
FIG. 16 shows a side-pumped Nd:YAG laser spatial beam profile.

In addition to high pumping efficiency, another advantage of diffuse pump chambers is uniform pumping. The spatial beam profile of the Nd:YAG laser operating at 1 J is shown in FIG. 16 where the excellent spatial homogeneity will prevent formation of hot spots during operation as a Q-switched cavity dumped sub-nanosecond laser. Diode-pumped Alexandrite lasers have been previously demonstrated (see Scheps et al., "Alexandrite Laser Pumped by Semiconductor Lasers," Appl. Phys. Lett. 56(23), 2288-2290 (1990) hereby incorporated by reference in its entirety), but the lack of a high peak-power pump source limited the output power. The GaInP/AlGaInP material system used to produce diode laser bars in the 650-680 nm range has been used to pump Alexandrite lasers.

As discussed above, the required array peak power is on the order of 10 kW, which requires twenty-five 400 W bars. For an Alexandrite laser, a polarized pump source is used to counter asymmetric pump absorption along the crystalline axes. According to certain aspects, bars may be provided that provide greater than 300 W peak power.

Figure 17:
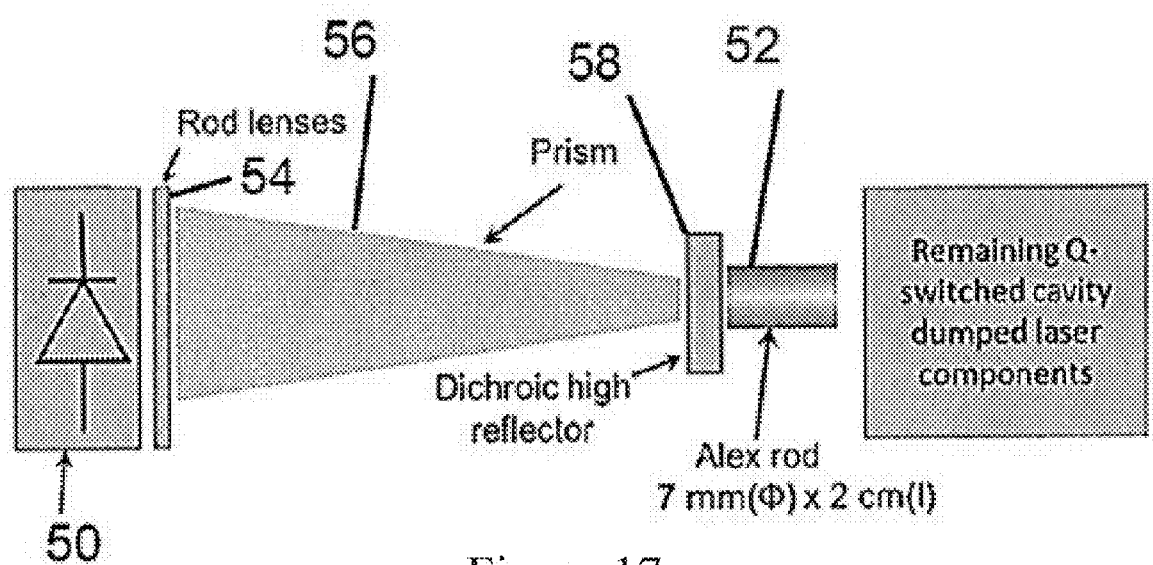
FIG. 17 shows an end-pumped Alexandrite laser.

According to one aspect, an end-pumping configuration depicted in FIG. 17 is provided that requires additional optics (when compared to side pumping discussed above) in order to couple light from a 24 bar array 50 into an Alexandrite crystal 52. In this case, the crystal is cut such that the pump light is polarized parallel to the b axis. For example, for the optimum 7 mm diameter rod identified previously, an exemplary spot size at the crystal is less than 5×5 mm$^2$ to ensure the pump energy is deposited within the rod diameter. To efficiently couple the fast axis light into a 5 mm spot requires collimation of all the diode laser bars 50, which can be accomplished with either one rod lens 54 per bar or one rod lens 54 for every two bars (assuming the two 12 bar stacks are well aligned to each other). Once the fast axis is collimated, a glass prism 56 can be used to create a 5×5 mm² spot at the rod input.

The gain-medium length and doping and pump wavelength are selected such that greater than 80% of the pump light is absorbed. The dichroic mirror 58 transmits at the 650-680 nm pump wavelength range and reflects at the 750 nm Alexandrite laser wavelength. The dichroic mirror 58 has minimal thickness and, if possible, high refractive index (e.g., undoped YAG) and the distance between the dichroic mirror and the Alexandrite rod 52 is less than 0.5 mm in order to minimize the spot size expansion as the pump beam propagates from the prism 56 into the Alexandrite rod 52.

If achieving the required 10 kW peak power in a single 24-bar array is not optimal, it is possible to combine the output of two 5 kW 24 bar arrays that operate at two different wavelengths within the Alexandrite absorption band. For example, if one array emits at 650 nm and the second array emits at 670 nm with the same linear polarization, a dichroic mirror can be used to combine the output of the two arrays into a single beam that (with suitable beam shaping optics) can be used to end pump the Alexandrite rod. It is also possible to combine two arrays emitting at 650 and 670 nm in orthogonal linear polarization states and then use an optical rotator to make the polarization direction of both beams parallel.

Figure 18:
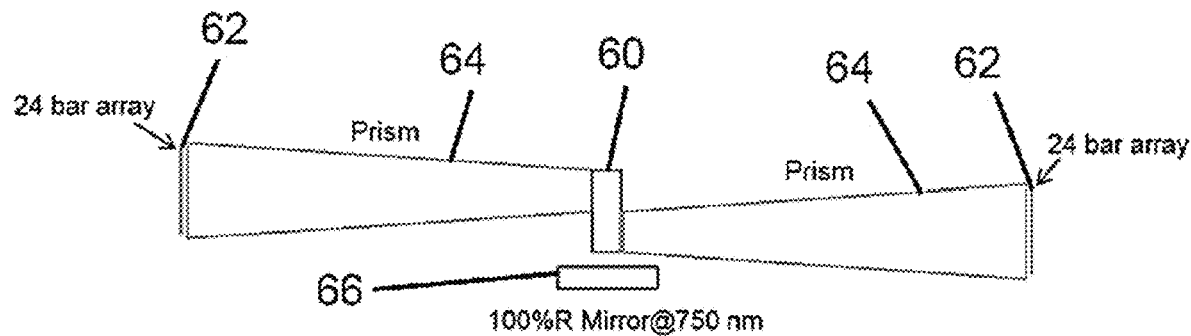
FIG. 18 shows a side-pumped Alexandrite laser.

According to one aspect, a pumping configuration is shown in FIG. 18, which can be used if achieving the required 10 kW in a single 24-bar array is not optimal. In this case, a block or crystal 60 of Alexandrite is side-pumped by two 24-bar 5 kW arrays 62 with lasing occurring straight down the length. The portion of the crystal 60 that faces opposite each array is coated for high reflection at the pump wavelength and high transmission at the lasing wavelength. High transmission at the lasing wavelength reduces the chances of parasitic lasing reducing the available inversion during the hold-off period. Similar to the end-pumped geometry, prisms 64 (or other optical means) can be used to couple pump light from the diode array 62 into the crystal 60. The crystal cross-section and doping level are chosen such that greater than 80% of the pump light is absorbed after double passing the crystal. In this case, the 100% reflectivity mirror 66 shown in FIG. 18 replaces mirror M2 in FIG. 1. The mirror 66 no longer needs to have minimum reflectivity at the pump wavelength. The benefit of eliminating the pump transmission requirement for the laser cavity mirror is significant. Even if the required 400 W bars are available, the side-pumped geometry may still be the optimum choice. In this case, each array consists of twelve bars located at the prism input. In addition, the side-pumped geometry eliminates the need for micro-optics to collimate the fast-axis diode light if the fast-axis divergence is sufficiently low to maintain high transmission through the prism.

Figure 19:
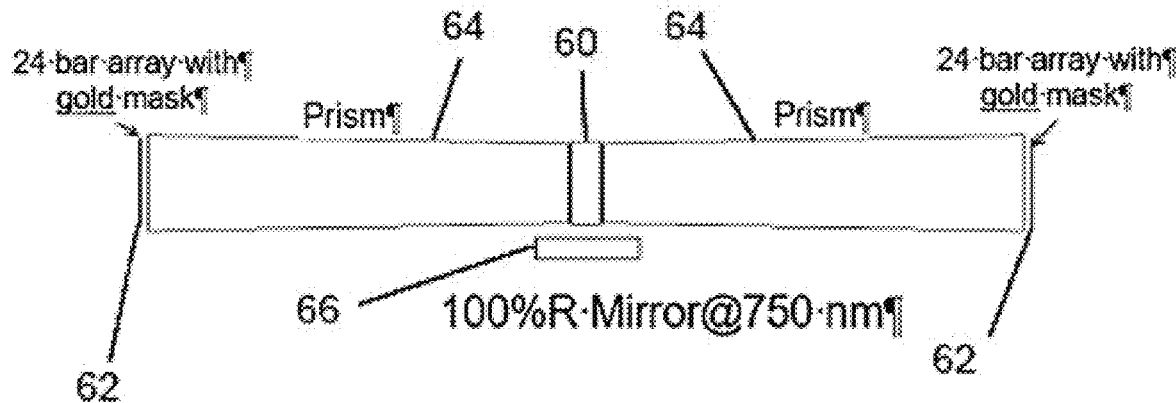
FIG. 19 shows a side-pumped Alexandrite laser in an alternate configuration.

According to one aspect, a side-pumped configuration is shown in FIG. 19. Similar to the pump geometry shown in FIG. 18, the two arrays 62 are configured with either 12 or 24 bars. Since pump light that is not absorbed in a single pass will be incident on the opposing diode array, it is advantageous to place a gold-coated mirror mask over each diode array. The mirror mask has slits that allow the outgoing diode light to propagate toward the crystal 60. By minimizing the area of the slits, the amount of unabsorbed diode light from the opposing array reflected back towards the crystal 60 is maximized. The crystal faces through which the pump passes are anti-reflection coated for the pump wavelength.

Since the pump light (not including light reflected from the mirror mask) is now absorbed in a single pass (as opposed to the geometry shown in FIG. 18), the crystal cross-section and doping level are chosen such that greater than 80% of the pump light is absorbed after a single pass through the crystal. The width of the prism output is chosen so as to nominally match the crystal length. The wide width allows the use of bars with high fast-axis divergence. In addition, referring to the geometry shown in FIG. 18, the requirement for a high reflectivity coating on the crystal face opposite each array is eliminated. The primary disadvantage is the requirement that the pump light be absorbed in a single pass instead of a double pass. High absorption can produce areas of high pump intensity near the pump faces, which can lead to hot spots in the laser beam.

Vertical-cavity surface-emitting lasers (VCSELs) are an alternative to diode laser bars that are typically used to pump solid state lasers. In this case, an array of twenty five 5×5 mm² chips (400 W per chip) is used to produce the required 10 kW peak power pump source. Each chip consists of thousands of emitters, which minimizes the chances of optical damage. VCSELs can be grown on large wafers and then diced into chips with testing performed at the wafer level. Since the divergence of the light from each VCSEL chip is symmetric (unlike diode laser bars), the optical delivery system is simplified. Many different optical systems (e.g., a two-lens system, prisms, parabolic concentrators, etc.) can be used to couple the output of a VCSEL array into an Alexandrite crystal.

Example IV

Transverse Positioning of the Laser Gain Medium to an Excitation or Pump Source

According to one aspect, the sub-nanosecond round trip time of the laser resonator as described herein may be achieved by a longitudinal laser gain medium having a length of 20 mm to 40 mm, depending on the length of the electro-optical, Q-switch and other resonator components. Aspects of the present disclosure are directed to the relative positioning of the laser medium to the excitation or pump source. Exemplary excitation or pump sources are described herein and are known to those of skill in the art and include a flash lamp. Cylindrical shaped flash lamps are known in the art, as are helical shaped flash lamps. It is to be understood that the present disclosure contemplates flash lamps known to those of skill in the art whether unitary in nature or composed of several or a plurality of individual flash lamps or excitation energy sources. The present disclosure contemplates the use of one or more excitation or pump sources. Various geometries of excitation sources known to those of skill are also contemplated.

Aspects of the present disclosure describe the positioning of the excitation or pump source, such as a longitudinal excitation or pump source, parallel to a laser medium (for example, such that the geometric axis of the excitation or pump source is parallel to the optical axis of the laser medium), such as a longitudinal or cylindrical laser medium as is known in the art, so that the excitation energy is directed along the length of the longitudinal or cylindrical laser medium. Many flash lamp pumped lasers are configured such that the gain medium, which may be a crystal having a cylindrical shape, is positioned in parallel with cylindrically shaped flash lamp(s). One or more individual excitation or pump sources may be positioned along the length of the longitudinal or cylindrical laser medium to create a longitudinal source of excitation energy. One or more excitation or pump sources may be positioned along the same side of the longitudinal or cylindrical laser medium or on different sides or along different portions of the length. Excitation or pump sources may be positioned on opposite sides of the longitudinal or cylindrical laser medium or at any position or location around the longitudinal or cylindrical laser medium. Excitation or pump sources may be positioned to surround the longitudinal or cylindrical laser medium. Excitation or pump sources may be positioned at right angles to each other around the longitudinal or cylindrical laser medium, such as four excitation or pump sources positioned directly opposite each other along and around the length of the longitudinal or cylindrical laser medium. The excitation or pump source may be a singular excitation source or pump unit or a plurality or excitation source or pump units. The excitation or pump source may extend beyond the longitudinal or cylindrical laser medium, may be co-terminus with the longitudinal or cylindrical laser medium or may be within the length of the longitudinal or cylindrical laser medium. Flash lamps with a geometric axis parallel to the optical axis of the gain medium can extend beyond the length of the gain medium in the resonator, may be co-terminus with the length of the gain medium, or may be within the length of the gain medium.

Suitable optical elements may be used as described herein and as known in the art for channeling or directing the excitation energy from the excitation or pump source to the laser medium along its length. According to one aspect, the laser head containing the gain medium and the flash lamp(s) may be optimized for optimal coupling of energy from the flash lamps into the gain medium, or rod through its length.

Aspects of the present disclosure also describe the positioning of the excitation or pump source at one end of the longitudinal or cylindrical laser medium such that the excitation energy is directed to and through the end of the longitudinal or cylindrical laser medium, such as along the optical or geometric axis of the longitudinal or cylindrical laser medium. Suitable optical elements may be used as described herein and as known in the art for channeling or directing the excitation energy from the excitation or pump source to the laser medium at its end and to enter the end of the laser gain medium. According to one aspect, the laser head containing the gain medium and the flash lamp(s) may be optimized for optimal coupling of energy from the flash lamps into the gain medium, or rod through its end.

In certain embodiments, the laser gain medium may be positioned transversely with respect to the excitation or pump source which may include one or more, or a pair or a plurality of radiation sources, such as a flash lamp(s). In this manner, a portion of the laser gain medium is directly exposed to the radiation produced by the excitation or pump source. A portion of the laser gain medium is not directly exposed to the radiation produced by the excitation or pump source. According to one aspect, a mid-portion of the laser gain medium is directly exposed to the radiation produced by the excitation or pump source. According to one aspect, an off-center portion of the laser gain medium is directly exposed to the radiation produced by the excitation or pump source. According to this aspect, the excitation or pump source includes at least one flash lamp having an axis (for example a geometric axis) transverse to the optical axis of the lasing medium. According to this aspect, the excitation or pump source includes a pair of flash lamps, with each flash lamp having an axis (for example a geometric axis) transverse to the optical axis of the lasing medium. According to this aspect, the excitation or pump source includes a plurality of flash lamps, with each flash lamp having an axis (for example a geometric axis) transverse to the optical axis of the lasing medium. According to this aspect, the longitudinal laser gain medium is positioned perpendicular to the longitudinal excitation or pump source. One of skill in the art will understand that the perpendicular or transverse positioning need not be exactly a 90 degree offset, but that variations are allowed within suitable tolerances.

According to one aspect, the longitudinal laser gain medium is positioned at an angle relative to the longitudinal excitation or pump source. According to one aspect, the longitudinal laser gain medium has an optical axis that is positioned at an angle relative to the geometric axis of the longitudinal excitation or pump source. According to one aspect, the angle is greater than 0 degrees and less than 90 degrees, with 0 degrees being a parallel arrangement and 90 degrees being a transverse or perpendicular arrangement. According to one aspect, the angle is between 30 degrees and less than 90 degrees. According to one aspect, the angle is between 60 degrees and less than 90 degrees. According to one aspect, the angle is between 30 degrees and 60 degrees. According to one aspect, the angle is between 30 degrees and 75 degrees. According to one aspect, the angle of the laser gain medium (for example the optical axis) is between 30 degrees and 150 degrees relative to the excitation or pump source (for example the geometric axis). One aspect is the proviso that the angle is not 90 degrees. According to one aspect, the angle of the laser gain medium (for example the optical axis) is between 60 degrees and 120 degrees relative to the excitation or pump source (for example the geometric axis). One aspect is the proviso that the angle is not 90 degrees. According to one aspect, the angle of the laser gain medium (for example the optical axis) is between 75 degrees and 105 degrees relative to the excitation or pump source (for example the geometric axis). One aspect is the proviso that the angle is not 90 degrees. One of skill in the art will understand that angling the laser gain medium less than 90 degrees towards zero degrees relative to the longitudinal excitation or pump source (i.e., toward being parallel with the longitudinal excitation or pump source) increases the excitation energy directly impinging the laser gain medium, as the laser gain medium and the excitation source become closer to being parallel.

According to one aspect, transverse or angled positioning of the longitudinal laser gain medium relative to the longitudinal excitation or pump source produces sufficient laser light in a suitable laser head design, even though the coupling efficiency for transverse positioning of the flash lamp(s) as described herein will be lower compared to parallel positioning as described herein.

Figure 20:
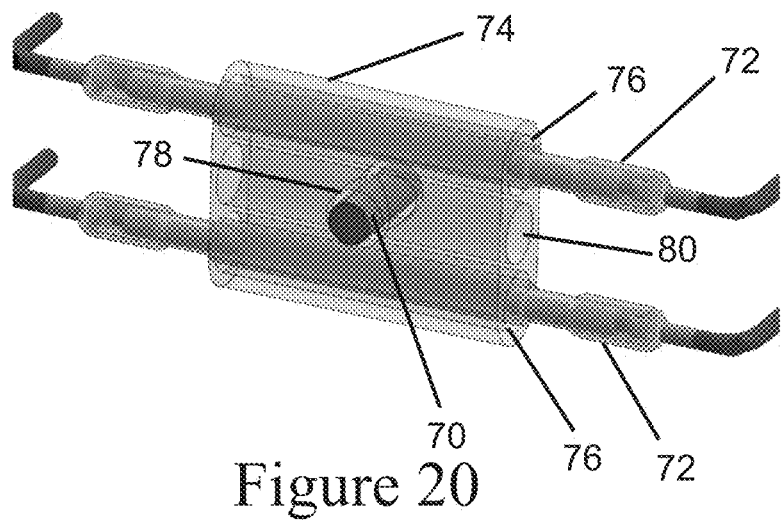
FIG. 20 shows a laser gain medium positioned transversely to flash lamps in a manifold.
Figure 21:
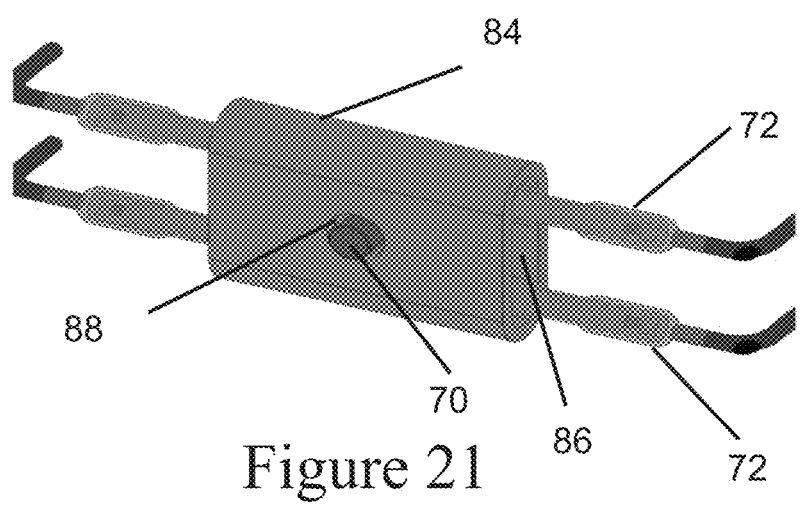
FIG. 21 shows a laser gain medium and flash lamps positioned transversely in a ceramic diffuse reflector.
Figure 22:
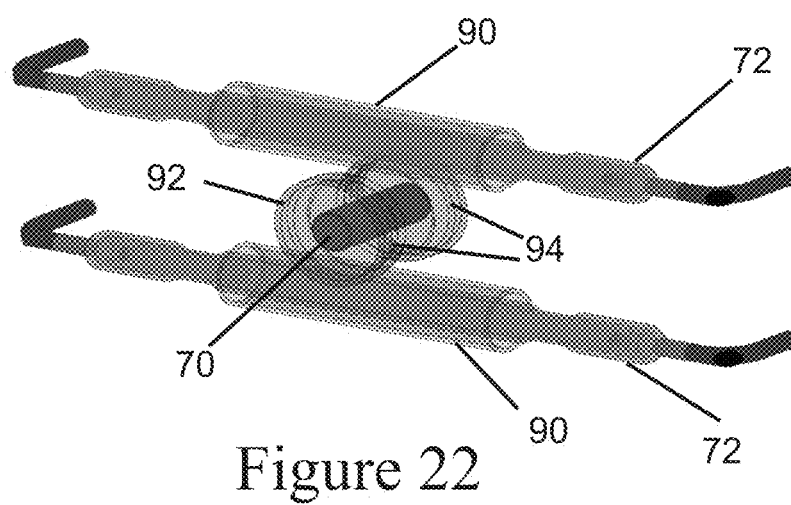
FIG. 22 shows a laser gain medium and flash lamps positioned transversely in separate glass flow tubes.

FIGS. 20, 21 and 22 generally depict two longitudinal flash lamps 72 each having a geometric axis with a longitudinal laser gain medium having an optical axis positioned there between and in a transverse manner. The embodiments differ in the support structure or cooling structure interacting with the flash lamps and the laser gain medium.

According to one particular embodiment of a laser head design as seen in FIG. 20, a longitudinal laser gain medium or lasing medium 70 and two longitudinal flash lamps 72 (an upper flash lamp and a lower flash lamp) may be positioned in a manifold 74 providing water flow for cooling. The laser gain medium and its optical axis is positioned between the two flash lamps and transverse to the geometric axis of the two flash lamps. In certain embodiments, manifold 74 may be formed of glass. Other suitable materials for manifold 74 will become readily apparent to those skilled in the art, given the benefit of this disclosure.

Each flash lamp 72 is positioned within and extends through a flash lamp channel 76 formed in manifold 74. Lasing medium 70 is positioned within and extends through a lasing channel 78 formed in manifold 74, with lasing channel 78 extending transversely with respect to flash lamp channels 76 through a central channel 80 of manifold 74. Water can be supplied to the channels of manifold 74 in known fashion to provided suitable cooling. In this manner of transverse positioning, a portion of the longitudinal laser gain medium is directly exposed to the excitation energy from the two longitudinal excitation or pump sources. In this manner of transverse positioning, a portion of the longitudinal laser gain medium is not directly exposed to the excitation energy from the two longitudinal excitation or pump sources. In this manner of transverse positioning, a portion of the longitudinal laser gain medium extends outside of the manifold and is not directly exposed to the excitation energy from the two longitudinal excitation or pump sources.

According to the embodiment of transverse positioning, a shorter laser gain medium can be used to generate significant laser light compared to an embodiment where excitation or pump sources are positioned parallel to a longer laser gain medium. According to one aspect, a 2-inch flash lamp arc length was used with a 21 mm Alexandrite rod as lasing medium 70 positioned transversely to the flash lamp. The stored energy in the 21 mm Alexandrite rod was approximately 50% of the stored energy of an 80 mm Alexandrite rod where the same flash lamps were positioned parallel to the length of the 80 mm Alexandrite rod. In certain embodiments, a diffuse reflector may be disposed on the external surfaces of manifold 74.

Aspects of the present disclosure are directed to a resonator design that generates a sub-nanosecond round trip time. According to one aspect of the present disclosure, one or more flash lamps or excitation sources that are positioned parallel to the lasing or gain medium or rod can extend beyond the length of the rod and add to the length of the resonator and extend the round trip time of the resonator. Such extended length of the resonator due to additional flash lamp length can affect the ability of the resonator to generate a sub-nanosecond round trip time. As is known in the art, flash lamps include a glass tube enclosing a gas mixture for electrical discharge and two electrodes on both ends. An exemplary design for parallel flash lamps would match the rod length to the electrical discharge length, leaving the two electrodes, which can be around 25 mm in length, extending beyond the rod length. According to one aspect, one or more optical elements can be positioned between the flash lamps to minimize or avoid the additional resonator length due to flash lamps extending beyond the length of the rod. According to this aspect and with reference to FIG. 1, the Polarizer and the M2 mirror may be positioned very close to the rod between the flash lamps. However, such a design adds complexity due to the high voltage power supply, such as between 300 to 900V, that would be connected to the flash lamps, as well as structure for water cooling of the device.

According to an alternate embodiment of a laser head design as seen in FIG. 21, both flash lamps 72 as described in FIG. 20 may extend through a ceramic diffuse reflector 84. Flash lamps 72 may extend in parallel through a single flash lamp channel 86 formed in the ceramic diffuse reflector 84. Lasing medium 70 as described in FIG. 20 may extend through a lasing medium channel 88 formed in the ceramic diffuse reflector 84, with the lasing medium channel 88 extending transversely with respect to flash lamp channel 86. In the case where lasing medium 70 is formed of Alexandrite, the ceramic material may be selected for high reflectivity in the Alexandrite pumping bands so as to provide an acceptable lifetime.

According to an alternate embodiment of a laser head design as seen in FIG. 22, flash lamps 72 as described in FIG. 20 extend through separate glass flash lamp flow tubes 90. Lasing medium 70 as described in FIG. 20 is seated in a glass lasing medium flow tube 92, with lasing medium 70 and lasing flow tube 92 extending transversely with respect to flash lamps 72 and flash lamp flow tubes 90. It is to be appreciated that flow tubes 90 and 92 can be shaped as desired. In the illustrated embodiment, flash lamp flow tubes 90 are cylindrical tubes, while lasing flow tube 92 has an hourglass shape to allow for compact positioning of lasing medium 70 and the transverse flash lamps 72 and flash lamp flow tubes 90. Lasing flow tube 92 may also include peripheral channels 94 at opposed ends thereof in order to receive O-rings, to prevent leakage when water is provided to lasing flow tube 92. It is to be appreciated that flash lamp flow tubes 90 and lasing medium flow tube 92 are supported with the laser head design and may each have different shapes, and other suitable shapes will become readily apparent to those skilled in the art, given the benefit of this disclosure.

Example V

Uses

A laser apparatus as described herein is used to generate pulsed laser energy having a pulse duration of 100 to 900 ps with 200 to 800 mJ/pulse. The laser apparatus includes a resonator with two substantially totally reflective mirrors at opposite ends of its optical axis. An Alexandrite crystal lasing medium, a polarizer, and a Pockels cell are positioned along this optical axis. An optical flash lamp is also included for pumping the Alexandrite lasing medium, which generates laser energy having a wavelength in the range of 700 to 800 nm.

The pulsed laser energy described above is generated by pumping the lasing medium within a laser resonator having a sub-nanosecond round trip time and Q-switching and cavity dumping the laser energy to produce an output pulse having a sub-nanosecond pulse duration.

Laser energy having the pulse duration and energy as described above is applied to a patient undergoing treatment for the removal of a tattoo. This laser energy is applied over the course of a 30-minute treatment session to all areas of the skin having undesired tattoo pigment particles. Photomechanical disruption of these particles is effected using the short pulse duration (similar to the transit time of a sound wave through the targeted tattoo pigment particles), together with a fluence in the range of 2 to 4 J/cm$^2$. This fluence is achieved with a laser energy spot diameter of about 5 mm.

Most if not all of the undesired tattoo pigment particles are effectively photomechanically disrupted, destabilized, and/or broken apart using one or two treatments. As a result, the disrupted particles are cleared from the body via normal physiological processes, such as the immune response. The tattoo is thus eventually cleared from the skin with no remaining visible signs. In this manner, various methods described herein are considered methods for treating or removing pigmented particles such as tattoo particles.

Example V

Embodiments

Aspects of the present disclosure are directed to a laser oscillator for generating laser energy having a pulse duration of less than 1 nanosecond. The laser oscillator includes (a) a first mirror and a second mirror within a housing, with the first mirror and the second mirror providing a sub-nanosecond round trip time for laser radiation along an axis between the first mirror and the second mirror; (b) an electro-optic device, a polarizer and a lasing medium positioned between the first mirror and the second mirror along the axis; (c) a pump source operatively coupled to the lasing medium; and (d) wherein the laser oscillator is capable of proceeding through at least three consecutive states comprising hold-off, buildup and cavity dumping. According to one aspect, the cavity dumping state has a range of acceptable transient times that are greater than the ideal step function transient time. According to one aspect, the cavity dumping state has a range of acceptable transient times that are greater than the ideal step function transient time, wherein a range of acceptable transient times includes from 0.5 round trip times to 5 round trip times which generates output pulse durations that range from 1 round trip time to 2.5 round trip times, the round trip time being sub-nanosecond. According to one aspect, the first mirror and the second mirror are fixed within the housing to define a static resonator chamber having a sub-nanosecond round trip time. According to one aspect, the lasing medium includes Alexandrite, Ti:S, Nd:YAG, Nd:YAP, Nd:YAlO$_3$, Nd:YLF, yttrium-aluminum garnet doped with a rare earth or a transition metal ion dopant, yttrium-aluminum perovskite doped with a rare earth or a transition metal ion dopant, yttrium aluminum oxide doped with a rare earth or a transition metal ion dopant, a vanadate crystal, YVO$_4$, fluoride glasses, ZBLN, silica glasses, minerals, ruby, crystals or glass media hosts. According to one aspect, the electro-optical device is a Pockels cell. According to one aspect, the sub-nanosecond round trip time is between 500 and 900 ps. According to one aspect, the sub-nanosecond round trip time is between 700 and 800 ps. According to one aspect, the pump source operatively coupled to the lasing medium provides pumping radiation along a longitudinal side of the lasing medium. According to one aspect, the pump source operatively coupled to the lasing medium provides pumping radiation along a longitudinal side of the lasing medium via an optical element. According to one aspect, the pump source operatively coupled to the lasing medium provides pumping radiation along a longitudinal side of the lasing medium via a prism. According to one aspect, the pump source includes at least one flash lamp having an axis transverse to the optical axis of the lasing medium. According to one aspect, the pump source includes a pair of flash lamps, each flash lamp having an axis transverse to the optical axis of the lasing medium. According to one aspect, the pump source includes a plurality of flash lamps, each flash lamp having an axis transverse to the optical axis of the lasing medium. According to one aspect, the pump source operatively coupled to the lasing medium includes two pump sources providing pumping radiation along opposite longitudinal sides of the lasing medium via an optical element. According to one aspect, the pump source operatively coupled to the lasing medium provides pumping radiation along an end of the lasing medium via an optical element. According to one aspect, the pump source operatively coupled to the lasing medium provides pumping radiation along an end of the lasing medium via a prism.

Aspects of the present disclosure are directed to a method of generating sub-nanosecond pulsed laser energy. The method includes (a) providing a resonator having a first mirror at one end, a second mirror at the opposite end, a lasing medium, a polarizer, and an electro-optic device disposed therebetween, and wherein the resonator has a cavity round trip time of less than 1 nanosecond, and wherein the lasing medium is pumped by a pump source operatively connected to the lasing medium; (b) applying a first voltage to the electro-optic device to hold off laser oscillation in the resonator while pumping energy into the lasing medium; (c) applying a second voltage to the electro-optic device to build up laser energy within the resonator; and (d) applying a third voltage to the electro-optic device to cavity dump a portion of the laser energy from the resonator. According to one aspect, the third voltage applied to the electro-optic device is a quarter wave voltage $V_{\lambda/4}$. According to one aspect, the transient time between the second applied voltage and the third applied voltage is greater than the ideal step function transient time. According to one aspect, the transient time between the second applied voltage and the third applied voltage is greater than the ideal step function transient time and wherein a range of acceptable transient times includes from 0.5 round trip times to 5 round trip times which generates output pulse durations that range from 1 round trip time to 2.5 round trip times, the round trip time being sub-nanosecond. According to one aspect, the pulsed laser energy has a pulse duration of between 100 ps and 900 ps. According to one aspect, the pulsed laser energy has a pulse duration of between 200 ps and 800 ps. According to one aspect, the pulsed laser energy has a pulse duration of between 600 ps and 800 ps. According to one aspect, the pulsed laser energy has at least 100 mJ/pulse. According to one aspect, the pulsed laser energy has from 200 to 800 m J/pulse. According to one aspect, the first mirror and the second mirror are fixed within the housing to define a static resonator chamber having a sub-nanosecond round trip time. According to one aspect, the lasing medium comprises Alexandrite, Ti:S, Nd:YAG, Nd:YAP, Nd:YAlO$_3$, Nd:YLF, yttrium-aluminum garnet doped with a rare earth or a transition metal ion dopant, yttrium-aluminum perovskite doped with a rare earth or a transition metal ion dopant, yttrium aluminum oxide doped with a rare earth or a transition metal ion dopant, a vanadate crystal, YVO$_4$, fluoride glasses, ZBLN, silica glasses, minerals, ruby, crystals or glass media hosts. According to one aspect, the electro-optic device is a Pockels cell. According to one aspect, the sub-nanosecond round trip time is between 500 and 900 ps. According to one aspect, the sub-nanosecond round trip time is between 700 and 800 ps. According to one aspect, the pump source operatively coupled to the lasing medium provides pumping radiation along a longitudinal side of the lasing medium. According to one aspect, the pump source operatively coupled to the lasing medium provides pumping radiation along a longitudinal side of the lasing medium via an optical element. According to one aspect, the pump source operatively coupled to the lasing medium provides pumping radiation along a longitudinal side of the lasing medium via a prism. According to one aspect, the pump source includes at least one flash lamp having an axis transverse to the optical axis of the lasing medium. According to one aspect, the pump source includes a pair of flash lamps, each flash lamp having an axis transverse to the optical axis of the lasing medium. According to one aspect, the pump source includes a plurality of flash lamps, each flash lamp having an axis transverse to the optical axis of the lasing medium. According to one aspect, the pump source operatively coupled to the lasing medium includes two pump sources providing pumping radiation along opposite longitudinal sides of the lasing medium via an optical element. According to one aspect, the pump source operatively coupled to the lasing medium provides pumping radiation along an end of the lasing medium via an optical element. According to one aspect, the pump source operatively coupled to the lasing medium provides pumping radiation along an end of the lasing medium via a prism.

Aspects of the present disclosure include a method of generating sub-nanosecond pulsed laser energy and treating pigmented skin. The method includes (a) providing a resonator having a first mirror at one end, a second mirror at the opposite end, a lasing medium, a polarizer, and an electro-optic device are disposed there between, and wherein the resonator has a cavity round trip time of less than 1 nanosecond, and wherein the lasing medium is pumped by a pump source operatively connected to the lasing medium; (b) applying a first voltage to the electro-optic device to hold off laser oscillation in the resonator while pumping energy into the lasing medium; (c) applying a second voltage to the electro-optic device to build up laser energy within the resonator; and (d) applying a third voltage to the electro-optic device to cavity dump a portion of the laser energy from the resonator; and (e) exposing pigmented skin of a patient to the laser energy with pulses having a duration of at most 990 ps and an energy of at least 10 mJ/pulse.

Aspects of the present disclosure includes a method for treating a skin pigmentation including (a) reflecting laser energy generated by a lasing medium between a first mirror at one end of a resonator and a second mirror at the opposite end of said resonator and through a polarizer and an electro-optical device within the resonator and wherein the resonator has a cavity round trip time of less than 1 nanosecond, and wherein the lasing medium is pumped by a pump source operatively connected to the lasing medium; (b) amplifying laser energy within the resonator by applying to the electro-optical device a first constant voltage; (c) Q-switching the resonator; and (d) then cavity dumping the amplified laser energy from the resonator by applying to the electro-optical device a quarter wave voltage $V_{\lambda/4}$; and exposing pigmented skin of a patient to the pulsed laser energy with pulses having a duration of at most 990 ps and an energy of at least 10 mJ/pulse.

In view of the above, it will be seen that several advantages may be achieved and other advantageous results may be obtained. Various changes could be made in the above apparatuses and methods without departing from the scope of the present disclosure. It is intended that all matter contained in this application, including all theoretical mechanisms and/or modes of interaction described above, shall be interpreted as illustrative only and not limiting in any way the scope of the appended claims.

Throughout this disclosure, various aspects are presented in a range format. The description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 5, from 3 to 6 etc., as well as individual whole and fractional numbers within that range, for example, 1, 2, 2.6, 3, 4, 5, and 6. This applies regardless of the breadth of the range.

Thus, while there have been shown, described, and pointed out fundamental novel features of various embodiments, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps which perform substantially the same function, in substantially the same way, to achieve the same results are within the scope of the invention. Substitutions of elements from one described embodiment to another are also fully intended and contemplated. It is the intention, therefore, to be limited only as indicated by the scope of the claims appended hereto.

What is claimed is:

1. A method of generating sub-nanosecond pulsed laser energy comprising:
   (a) providing a resonator having a first mirror at one end, a second mirror at the opposite end, a lasing medium, a polarizer, and an electro-optic device disposed therebetween, and wherein the resonator has a cavity round trip time of less than 1 nanosecond, and wherein the lasing medium is pumped by a pump source operatively connected to the lasing medium;
   (b) applying a first voltage to the electro-optic device to hold off laser oscillation in the resonator while pumping energy into the lasing medium;
   (c) applying a second voltage to the electro-optic device to build up laser energy within the resonator; and
   (d) applying a third voltage to the electro-optic device to cavity dump a portion of the laser energy from the resonator.

2. The method of claim 1 wherein the third voltage applied to the electro-optic device is a quarter wave voltage $V_{\lambda/4}$.

3. The method of claim 1 wherein the transient time between the second applied voltage and the third applied voltage is greater than the ideal step function transient time.

4. The method of claim 1 wherein the transient time between the second applied voltage and the third applied voltage is greater than the ideal step function transient time and wherein a range of acceptable transient times includes from 0.5 round trip times to 5 round trip times which generates output pulse durations that range from 1 round trip time to 2.5 round trip times, the round trip time being sub-nanosecond.

5. The method of claim 1 wherein the pulsed laser energy has a pulse duration of between 100 ps and 900 ps.

6. The method of claim 1 wherein the pulsed laser energy has a pulse duration of between 200 ps and 800 ps.

7. The method of claim 1 wherein the pulsed laser energy has a pulse duration of between 600 ps and 800 ps.

8. The method of claim 1, wherein said pulsed laser energy has at least 100 mJ/pulse.

9. The method of claim 1, wherein said pulsed laser energy has from 200 to 800 mJ/pulse.

10. The method of claim 1, wherein the first mirror and the second mirror are fixed within the housing to define a static resonator chamber having a sub-nanosecond round trip time.

11. The method of claim 1, wherein the lasing medium comprises Alexandrite, Ti:S, Nd:YAG, Nd:YAP, Nd:YAlO$_3$, Nd:YLF, yttrium-aluminum garnet doped with a rare earth or a transition metal ion dopant, yttrium-aluminum perovskite doped with a rare earth or a transition metal ion dopant, yttrium aluminum oxide doped with a rare earth or a transition metal ion dopant, a vanadate crystal, YVO$_4$, fluoride glasses, ZBLN, silica glasses, minerals, ruby, crystals or glass media hosts.

12. The method of claim 1, wherein the electro-optic device is a Pockels cell.

13. The method of claim 1, wherein the sub-nanosecond round trip time is between 500 and 900 ps.

14. The method of claim 1, wherein the sub-nanosecond round trip time is between 700 and 800 ps.

15. The method of claim 1, wherein the pump source operatively coupled to the lasing medium provides pumping radiation along a longitudinal side of the lasing medium.

16. The method of claim 1, wherein the pump source operatively coupled to the lasing medium provides pumping radiation along a longitudinal side of the lasing medium via an optical element.

17. The method of claim 1, wherein the pump source operatively coupled to the lasing medium provides pumping radiation along a longitudinal side of the lasing medium via a prism.

18. The method of claim 1, wherein the pump source operatively coupled to the lasing medium includes two pump sources providing pumping radiation along opposite longitudinal sides of the lasing medium via an optical element.

19. The method of claim 1, wherein the pump source operatively coupled to the lasing medium provides pumping radiation along an end of the lasing medium via an optical element.

20. The method of claim 1, wherein the pump source operatively coupled to the lasing medium provides pumping radiation along an end of the lasing medium via a prism.

21. The method of claim 1 wherein the pump source includes at least one flash lamp having an axis transverse to the optical axis of the lasing medium.

22. The method of claim 1 wherein the pump source includes a pair of flash lamps, each flash lamp having an axis transverse to the optical axis of the lasing medium.

23. The method of claim 1 wherein the pump source includes a plurality of flash lamps, each flash lamp having an axis transverse to the optical axis of the lasing medium.

24. The method of claim 1, wherein the pump source includes a manifold and a pair of flash lamps, each flash lamp extends through a flash lamp channel in the manifold, the lasing medium extends through a lasing channel in the manifold, and the lasing medium and lasing channel extend transversely with respect to the flash lamps and flash lamp channel.

25. The method of claim 1, wherein the pump source includes a ceramic diffuse reflector and a pair of flash lamps, the flash lamps extends through a flash lamp channel in the ceramic diffuse reflector, the lasing medium extends through a lasing channel in the ceramic diffuse reflector, and the lasing medium and lasing channel extend transversely with respect to the flash lamps and flash lamp channel.

26. The method of claim 1, wherein the pump source includes a pair of flash lamps, each flash lamp extends a flash lamp flow tube, the lasing medium extends through a lasing flow tube, and the lasing medium and lasing flow tube extend transversely with respect to the flash lamps and flash lamp flow tubes.

27. The method of claim 26, wherein the lasing flow tube has an hourglass shape and includes peripheral channels at opposed ends thereof.

28. A method of generating sub-nanosecond pulsed laser energy and treating pigmented skin comprising:
  (a) providing a resonator having a first mirror at one end, a second mirror at the opposite end, a lasing medium, a polarizer, and an electro-optic device are disposed there between, and wherein the resonator has a cavity round trip time of less than 1 nanosecond, and wherein the lasing medium is pumped by a pump source operatively connected to the lasing medium;
  (b) applying a first voltage to the electro-optic device to hold off laser oscillation in the resonator while pumping energy into the lasing medium;
  (c) applying a second voltage to the electro-optic device to build up laser energy within the resonator;
  (d) applying a third voltage to the electro-optic device to cavity dump a portion of the laser energy from the resonator; and
  (e) exposing pigmented skin of a patient to the laser energy with pulses having a duration of at most 990 ps and an energy of at least 10 mJ/pulse.

29. A method for treating a skin pigmentation comprising generating pulsed laser energy by:
  (a) reflecting laser energy generated by a lasing medium between a first mirror at one end of a resonator and a second mirror at the opposite end of said resonator and through a polarizer and an electro-optical device within the resonator and wherein the resonator has a cavity round trip time of less than 1 nanosecond, and wherein the lasing medium is pumped by a pump source operatively connected to the lasing medium;
  (b) amplifying laser energy within the resonator by applying to the electro-optical device a first constant voltage;
  (c) Q-switching the resonator;
  (d) then cavity dumping the amplified laser energy from the resonator by applying to the electro-optical device a quarter wave voltage $V_{\lambda/4}$; and
  (e) exposing pigmented skin of a patient to the pulsed laser energy with pulses having a duration of at most 990 ps and an energy of at least 10 mJ/pulse.

* * * * *